(12) United States Patent
Biden et al.

(10) Patent No.: US 8,598,146 B2
(45) Date of Patent: Dec. 3, 2013

(54) METHODS FOR IDENTIFYING MODULATORS OF PROTEIN KINASE C-EPSILON ($PKC_\epsilon$) AND METHOD OF TREATMENT OF ABERRANT GLUCOSE METABOLISM ASSOCIATED THEREWITH

(75) Inventors: Trevor John Biden, Neutral Bay (AU); Carsten Schmitz-Peiffer, Loftus (AU)

(73) Assignee: Garvan Institute of Medical Research, Darlinghurst, New South Wales (AU)

( * ) Notice: Subject to any disclaimer, the term of this patent is extended or adjusted under 35 U.S.C. 154(b) by 1335 days.

(21) Appl. No.: 10/572,110

(22) PCT Filed: Sep. 16, 2004

(86) PCT No.: PCT/AU2004/001255
§ 371 (c)(1),
(2), (4) Date: Dec. 20, 2006

(87) PCT Pub. No.: WO2005/025602
PCT Pub. Date: Mar. 24, 2005

(65) Prior Publication Data
US 2008/0263689 A1    Oct. 23, 2008

(30) Foreign Application Priority Data

Sep. 16, 2003  (AU) ............................... 2003905421
Jul. 22, 2004  (AU) ............................... 2004904077

(51) Int. Cl.
| | | |
|---|---|---|
| A01N 57/00 | (2006.01) | |
| A61K 31/665 | (2006.01) | |
| A61K 38/00 | (2006.01) | |
| A61K 38/28 | (2006.01) | |
| A61P 3/10 | (2006.01) | |
| A61P 7/12 | (2006.01) | |

(52) U.S. Cl.
USPC ........................................ 514/101; 514/6.9

(58) Field of Classification Search
None
See application file for complete search history.

(56) References Cited

U.S. PATENT DOCUMENTS

| | | | |
|---|---|---|---|
| 5,783,405 A | 7/1998 | Mochly-Rosen et al. | |
| 5,959,096 A | 9/1999 | Bennett et al. | |
| 6,339,066 B1 | 1/2002 | Bemmet et al. | |
| 6,521,815 B1 | 2/2003 | Verma et al. | |
| 7,235,526 B2 * | 6/2007 | Mochly-Rosen et al. | 514/17.5 |
| 2003/0134774 A1 | 7/2003 | Steinberg et al. | |

FOREIGN PATENT DOCUMENTS

| | | | | |
|---|---|---|---|---|
| WO | WO 98/17299 | * | 4/1998 | A61K 38/00 |
| WO | WO 00/01415 | | 1/2000 | |
| WO | WO 00/01805 | | 1/2000 | |
| WO | WO 00/29427 | * | 5/2000 | C07K 14/00 |
| WO | WO0238561 | | 5/2002 | |
| WO | WO 02/055664 | | 7/2002 | |
| WO | WO2004038040 | | 5/2004 | |

OTHER PUBLICATIONS

Akita, Protein kinase C-epsilon (PKC-epsilon): its unique structure and function, J Biochem. 132(6):847-52, 2002.*
Idris et al., Protein kinase C activation: isozyme-specific effects on metabolism and cardiovascular complications in diabetes, Diabetologia, 44(6):659-73, 2001.*
Considine et al., Protein kinase C is increased in the liver of humans and rats with non-insulin-dependent diabetes mellitus: an alteration not due to hyperglycemia, J Clin Invest. 95(6):2938-44, 1995.*
Schmitz-Peiffer et al. Alterations in the expression and cellular localization of protein kinase C isozymes epsilon and theta are associated with insulin resistance in skeletal muscle of the high-fat-fed rat., Diabetes, 46(2):169-78, 1997.*
Raulin et al., Lipids and retroviruses, Lipids, 35(2):123-30, 2000.*
Hribal, M. L., et al., The sulfonylurea glimepiride regulates intracellular routing of the insulin-receptor complexes through their interaction with specific protein kinase C isoforms, Molecular Pharmacology, Feb. 2001;59(2):322-330.
Wrede, C. E., et al., Fatty acid and phorbol ester-mediated interference of mitagenic signaling via novel protein kinase C isoforms in pancreatic beta-cells, Journal of Molecular Endocrinoogy, Jun. 2003;30(3):271-286.
Hoy, Marianne, et al., Involvement of protein kinase C-epsilon in inositol hexakisphosphate-induced exocytosis in mouse pancreatic beta-cells, The Journal of Biological Chemistry, Sep. 12, 2003;278(37):35168-35171.
Supplementary European Search Report, Jun. 15, 2009.
Bonini, J. A., et al., Compensatory alterations for insulin signal transduction and glucose transport in insulin-resistant diabetes, Am J Physiol. Oct. 1995;269(4 Pt 1):E759-65.
Asayama, K., et al., Increased peroxisomal fatty acid beta-oxidation and enhanced expression of peroxisome proliferator-activated receptor-alpha in diabetic rat liver, Mol Cell Biochem. Apr. 1999;194(1-2):227-34.
Lan, H., et al, Gene expression profiles of nondiabetic and diabetic obese mice suggest a role of hepatic lipogenic capacity in diabetes susceptibility, Diabetes. Mar. 2003;52(3):688-700.
Meistas, M. T., et al., Hyperinsulinemia of obesity is due to decreased clearance of insulin, Am J Physiol. Aug. 1983;245(2):E155-9.
Poy, M. N., et al., CEACAM1 regulates insulin clearance in liver, Nat Genet. Mar. 2002;30(3):270-6.
Frevert, E. U. and Kahn, B. B., Protein kinase C isoforms epsilon, eta, delta and zeta in murine adipocytes: expression, subcellular localization and tissue-specific regulation in insulin-resistant states, Biochem J. Jun. 15, 1996;316 ( Pt 3):865-71.

(Continued)

*Primary Examiner* — Cecilia J Tsang
*Assistant Examiner* — Zachary J Miknis
(74) *Attorney, Agent, or Firm* — Pepper Hamilton, LLP

(57) ABSTRACT

The present invention provides novel cell-based and animal-based assays for determining antagonists of PKCε and uses of the isolated antagonist compounds for modulating insulin clearance and secretion. The invention also provides novel animals and cells such as animals and cells suitable for use in the assays.

28 Claims, 25 Drawing Sheets

(56) References Cited

OTHER PUBLICATIONS

Yedovitzky, M., et al., Translocation inhibitors define specificity of protein kinase C isoenzymes in pancreatic beta-cells, J Biol Chem. Jan. 17, 1997;272(3):1417-20.

Yaney, G. C., et al., Potentiation of insulin secretion by phorbol esters is mediated by PKC-alpha and nPKC isoforms, Am J Physiol Endocrinol Metab. Nov. 2002;283(5):E880-8.

Sonnenberg, G. E., et al., Splanchnic insulin dynamics and secretion pulsatilities in abdominal obesity, Diabetes. Mar. 1994;43(3):468-77. (Abstract Only).

Ntambi, J. M., et al., Loss of stearoyl-CoA desaturase-1 function protects mice against adiposity, Proc Natl Acad Sci U S A. Aug. 20, 2002;99(17):11482-6.

Warwar, N., et al., Dynamics of Glucose-Induced Localization of PKC Isoenzymes in Pancreatic Beta-Cells, Diabetes, Mar. 2006;55:590-599.

Ikeda, Y. et al., "Cellular Mechanism of Nutritionally Induced Insulin Resistance in *Psammomys obesus*—Overexpression of Protein Kinase Cε in Skeletal Muscle Precedes the Onset of Hyperinsulinemia and Hyperglycemia", Diabetes, 2001, 50:584-589.

Huang, Chuanshu et al., "Potentiation of Insulin-Induced Phosphatidylinositol-3 Kinase Activity by Phorbol Ester is Medicated by Protein Kinase Cε", Cell Signal, 1998, 10(3):185-190.

Raddatz, K., et al., Time-dependent effects of Prkce deletion on glucose homeostasis and hepatic lipid metabolism on dietary lipid oversupply in mice, Diabetologia. Feb. 24, 2011.

Frangioudakis, G., et al., Diverse roles for protein kinase C delta and protein kinase C epsilon in the generation of high-fat-diet-induced glucose intolerance in mice: regulation of lipogenesis by protein kinase C delta, Diabetologia. Dec. 2009;52(12):2616-20.

Cantley, J., et al., Deletion of PKCepsilon selectively enhances the amplifying pathways of glucose-stimulated insulin secretion via increased lipolysis in mouse beta-cells, Diabetes. Aug. 2009;58(8):1826-34.

Schmitz-Peiffer, C. and Biden, T. J., Protein kinase C function in muscle, liver, and beta-cells and its therapeutic implications for type 2 diabetes, Diabetes. Jul. 2008;57(7):1774-83.

Schmitz-Peiffer, C., et al., Inhibition of PKCepsilon improves glucose-stimulated insulin secretion and reduces insulin clearance, Cell Metab. Oct. 2007;6(4):320-8.

Akita "Protein kinase C-epsilon (PKC-epsilon): its unique structure and function," *J Biochem* (Tokyo) (2002) 132(6):847-852.

Avignon et al., "Chronic activation of protein kinase C in soleus muscles and other tissues of insulin-resistant type II diabetic Goto-Kakizaki (GK), obese/aged, and obese/Zucker rats. A mechanism for inhibiting glycogen synthesis," *Diabetes* (1996) 45(10)1396-1404.

Frevert et al., "Protein kinase C isoforms epsilon, eta, delta and zeta in murine adipocytes: expression, subcellular localization and tissue-specific regulation in insulin-resistant states," *Biochem J* (1996) 316:865-871.

Huang et al., "Potentiation of insulin-induced phosphatidylinositol-3 kinase activity by phorbol ester is mediated by protein kinase C epsilon," *Cell Signal* (1998) 10(3):185-190.

Idris et al., "Insulin action in skeletal muscle: isozyme-specific effects of protein kinase C," *Ann NY Acad Sci* (2002) 967:176-182.

Idris et al., "Protein kinase C activation: isozyme-specific effects on metabolism and cardiovascular complications in diabetes," *Diabetologia* (2001) 44(6):659-673.

Ikeda et al., "Cellular mechanism of nutritionally induced insulin resistance in *Psammomys obesus*: overexpression of protein kinase Cepsilon in skeletal muscle precedes the onset of hyperinsulinemia and hyperglycemia," *Diabetes* (2001) 50(3):584-592.

Ono et al., "The structure, expression, and properties of additional members of the protein kinase C family," *Journal of Biological Chemistry* (1988) 263(14):6927-6932.

Qu et al., "Tissue and isoform-selective activation of protein kinase C in insulin-resistant obese Zucker rats—effects of feeding," *Journal of Endocrinology* (1999) 162:207-214.

Schafir et al., "Nutritionally induced insulin resistance and receptor defect leading to beta-cell failure in animal models," *Annals New York Academy of Sciences* (1999) 892:223-46.

Schmitz-Peiffer et al., "Alterations in the expression and cellular localization of protein kinase C isozymes epsilon and theta are associated with insulin resistance in skeletal muscle of the high-fat-fed rat," *Diabetes* (1997) 46(2):169-178.

Song et al., "Induction of glucose-regulated protein 78 by chronic hypoxia in human gastric tumor cells through a protein kinase C-epsilon/ERK/AP-1 signaling cascade," *Cancer Res* (2001) 61(22):8322-8330.

* cited by examiner

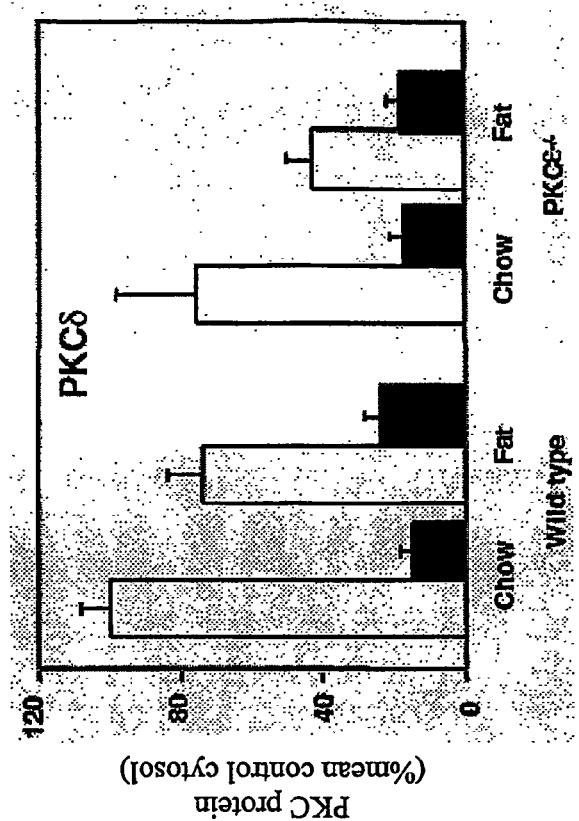
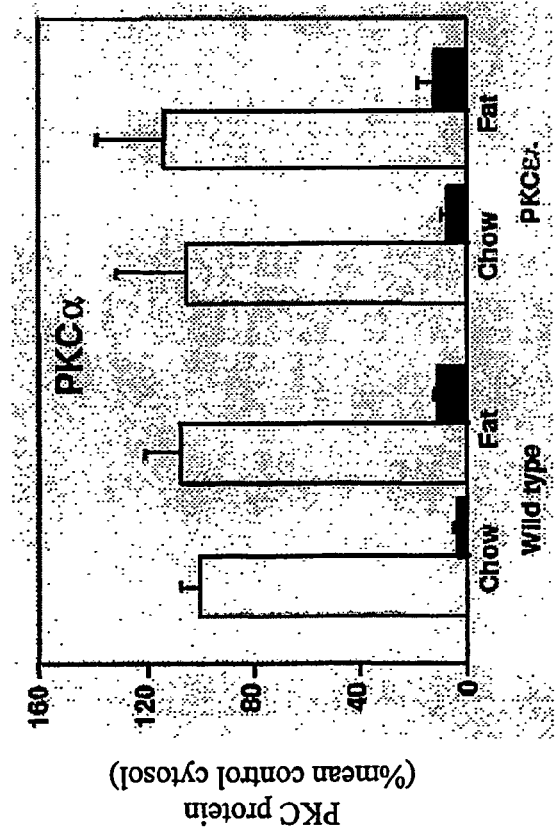
Figure 4d
Figure 4c

METHODS FOR IDENTIFYING MODULATORS OF PROTEIN KINASE C-EPSILON (PKCε) AND METHOD OF TREATMENT OF ABERRANT GLUCOSE METABOLISM ASSOCIATED THEREWITH

CROSS-REFERENCE TO RELATED APPLICATIONS

This application is a national stage application of PCT International Application Serial Number PCT/AU2004/001255 filed Sep. 16, 2004 which claims priority from Australian Provisional Application No. 2003905421 filed Sep. 16, 2003 and Australian Provisional Application No. 2004904077 filed Jul. 22, 2004.

FIELD OF THE INVENTION

This invention pertains to methods for regulating or ameliorating metabolic defects associated with glucose and insulin metabolism disorders, especially those associated with Type II diabetes. More particularly the present invention relates to methods for reducing in a subject, such as a vertebrate animal (including a human), at least one of the following indices of metabolism: insulin secretion, insulin resistance, glucose intolerance, hyperinsulinemia, hyperglycemia, and body fat stores. The method of the invention comprises reducing the level and/or activity of protein kinase C epsilon (PKCε), thereby reducing insulin clearance by the liver and/or enhancing insulin secretion by β-islet cells. Protection of β-islet cells from the adverse effects of a high-fat diet and/or elevated circulating lipid levels and/or a propensity to accumulate lipid in β-islet cells is also conferred. The present invention further provides methods for determining an antagonist compound of protein kinase C epsilon (PKCε) based upon the newly-identified roles of PKCε in the liver and pancreas, wherein the identified compounds are suitable for use in the methods of treatment described herein.

BACKGROUND TO THE INVENTION

1. General

This specification contains nucleotide and amino acid sequence information prepared using Patent In Version 3.1, presented herein after the claims. Each nucleotide sequence is identified in the sequence listing by the numeric indicator <210> followed by the sequence identifier (e.g. <210>1, <210>2, <213> etc). The length and type of sequence (DNA, protein (PRT), etc), and source organism for each nucleotide sequence, are indicated by information provided in the numeric indicator fields <211>, <212> and <213>, respectively. Nucleotide sequences referred to in the specification are defined by the term "SEQ ID NO:", followed by the sequence identifier (e.g. SEQ ID NO: 1 refers to the sequence in the sequence listing designated as <400>1).

The designation of nucleotide residues referred to herein are those recommended by the IUPAC-IUB Biochemical Nomenclature Commission, wherein A represents Adenine, C represents Cytosine, G represents Guanine, T represents thymine, Y represents a pyrimidine residue, R represents a purine residue. M represents Adenine or Cytosine, K represents Guanine or Thymine, S represents Guanine or Cytosine, W represents Adenine or Thymine, H represents a nucleotide other than Guanine, B represents a nucleotide other than Adenine, V represents a nucleotide other than Thymine, D represents a nucleotide other than Cytosine and N represents any nucleotide residue.

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

As used herein, the term "abnormality of glucose metabolism" shall be taken to mean one or more conditions selected from the group consisting of hyperglycemia, glucose intolerance, insulin resistance, hyperinsulinemia and β-islet cell dysfunction.

The term "elevated circulating lipid levels" shall be taken to mean a level of lipid clinically associated with an actual or enhanced risk of islet cell dysfunction or increased tendency to cell death. By "islet cell dysfunction" is meant an impaired ability of the islet cell to secrete insulin e.g., in response to glucose. Accordingly, a level of circulating lipid or amount of lipid in β-islet cells is an amount of lipid sufficient to enhance the risk of islet cell dysfunction or capable of causing actual islet cell dysfunction in a subject.

As used herein, the term "protein kinase C epsilon" or "PKCε" means an enzyme having the known substrate specificity and cofactor requirements of PKCε, and preferably, comprising an amino acid sequence that is at least about 80% identical to a sequence set forth herein as SEQ ID Nos: 2 or 4 or a portion thereof having PKCε activity. For the purposes of nomenclature, the amino acid sequences of the murine and human PKCε polypeptides are exemplified herein, as SEQ ID Nos: 2 and 4, respectively. Preferably, the percentage identity to SEQ ID NO: 2 or 4 is at least about 85%, more preferably at least about 90%, even more preferably at least about 95% and still more preferably at least about 99%. The term "PKCε" shall further be taken to mean a protein that exhibits the known biological activity of PKCε, or the known substrate and cofactor specificity of PKCε e.g., by transfer of phosphate to a substrate peptide comprising the amino acid sequence ERMRPRKRQGSVRRRV (SEQ ID NO: 5) in a calcium-independent manner and/or in response to phorbol ester.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purposes of exemplification only. Functionally equivalent products, compositions and methods are clearly within the scope of the invention, as described herein.

The embodiments of the invention described herein with respect to any single embodiment shall be taken to apply mutatis mutandis to any other embodiment of the invention described herein. In particular, the processes described herein with respect to the treatment of insulin resistance and/or the determination of modulators for the treatment of insulin resistance shall be taken to apply mutatis mutandis to processes for the treatment of glucose intolerance, hyperinsulinemia, and hyperglycaemia and/or to methods for the determination of modulatory compounds for the treatment of such conditions, particularly in obese subjects or subjects on a high-fat diet or showing elevated circulating lipid levels of having a propensity to accumulate lipid in β-islet cells or subjects suffering from NIDDM.

The present invention is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in the following texts that are incorporated herein by reference:

Sambrook, Fritsch & Maniatis, Molecular Cloning: A Laboratory Manual, Cold Spring Harbor Laboratories, New York, Second Edition (1989), whole of Vols I, II, and III;
DNA Cloning: A Practical Approach, Vols. I and II (D. N. Glover, ed., 1985), IRL Press, Oxford, whole of text;
Oligonucleotide Synthesis: A Practical Approach (M. J. Gait, ed., 1984) IRL Press, Oxford, whole of text, and particularly the papers therein by Gait, pp 1-22; Atkinson et al, pp 35-81; Sproat et al., pp 83-115; and Wu et al., pp 135-151;
Nucleic Acid Hybridization: A Practical Approach (B. D. Hames & S. J. Higgins, eds., 1985) IRL Press, Oxford, whole of text;
Animal Cell Culture: Practical Approach, Third Edition (John R. W. Masters, ed., 2000), ISBN 0199637970, whole of text;
Immobilized Cells and Enzymes: A Practical Approach (1986) IRL Press, Oxford, whole of text;
Perbal, B., A Practical Guide to Molecular Cloning (1984);
Methods In Enzymology (S. Colowick and N. Kaplan, eds., Academic Press, Inc.), whole of series;
J. F. Ramalho Ortigão, "The Chemistry of Peptide Synthesis" In: Knowledge database of Access to Virtual Laboratory website (Interactiva, Germany);
Sakakibara, D., Teichman, J., Lien, E. Land Fenichel, R. L. (1976). Biochem. Biophys. Res. Commun. 73 336-342
Merrifield, R. B. (1963). J. Am. Chem. Soc. 85, 2149-2154.
Barany, G. and Merrifield, R. B. (1979) in The Peptides (Gross, E. and Meienhofer, J. eds.), vol. 2, pp. 1-284, Academic Press, New York.
Wünsch, E., ed. (1974) Synthese von Peptiden in Houben-Weyls Metoden der Organischen Chemie (Müler, E., ed.), vol. 15, 4th edn., Parts 1 and 2, Thieme, Stuttgart
Bodanszky, M. (1984) Principles of Peptide Synthesis, Springer-Verlag, Heidelberg.
Bodanszky, M. & Bodanszky, A. (1984) The Practice of Peptide Synthesis, Springer-Verlag, Heidelberg.
Bodanszky, M. (1985) Int. J. Peptide Protein Res. 25, 449-474.
Handbook of Experimental Immunology, Vols. I-IV (D. M. Weir and C. C. Blackwell, eds., 1986, Blackwell Scientific Publications).

2. Description of the Related Art

Noninsulin-dependent diabetes mellitus (NIDDM or Type II diabetes) is a serious health concern, particularly in more developed societies that ingest foodstuffs high in sugars and/or fats. The disease is associated with blindness, heart disease, stroke, kidney disease, hearing loss, gangrene and impotence. Type II diabetes and its complications are leading causes of premature death in the Western world.

Generally, NIDDM adversely affects the way the body converts ingested sugars and starches into glucose. In muscle, adipose (fat) and connective tissues, insulin facilitates the entry of glucose into the cells by an action on the cell membranes. In the liver, the ingested glucose is normally converted to carbon dioxide and water (50%), glycogen (5%), and fat (30-40%). The fat is stored as fat deposits. Fatty acids from the adipose tissues are circulated, returned to the liver for re-synthesis of triacylglycerol and metabolized to ketone bodies for utilization by the peripheral tissues. The fatty acids are also metabolized by other organs.

NIDDM can be viewed as a failure of pancreatic β-cells to secrete sufficient insulin to overcome insulin resistance at the level of liver and skeletal muscle (De Fronzo Diabetes 37, 667-687, 1987; Polonsky et al, N. Engl. J. Med. 334, 777-783, 1996). Although the functional defects obviously differ, there is increasing evidence that an inappropriate accumulation of lipid in each of these tissues, as a result of either oversupply or altered cellular metabolism, might be a common etiological factor in the progression of the disease (Boden et al., Proc. Assoc. Am. Phys. 111, 241-248, 1999; McGarry Diabetes 51, 7-18, 2002; Bergman et al. Trends Endocrinol Metab. 11, 351-356, 2000; Lewis et al, Endocr, Rev. 23, 201-209, 2002). In most NIDDM subjects, the metabolic entry of glucose into various "peripheral" tissues is reduced and there is increased liberation of glucose into the circulation from the liver. Thus, there is an excess of extracellular glucose and a deficiency of intracellular glucose. Elevated blood lipids and lipoproteins are a further common complication of diabetes. The cumulative effect of these diabetes-associated abnormalities is severe damage to blood vessels and nerves. Although the pancreas retains the ability to produce insulin, and in fact may produce higher man normal amounts of insulin (hyperinsulinemia), in diabetic subjects this insulin is insufficient to overcome the cellular resistance to insulin that occurs in obese subjects (i.e. "insulin resistance.

Insulin resistance can be defined as a state in which a normal amount of insulin produces a suboptimal metabolic response compared to the metabolic response of a normal or healthy subject. Insulin resistance is therefore a failure of target tissues to increase whole body glucose disposal in response to insulin. In insulin-treated patients suffering from Type II diabetes, insulin resistance is considered to be present whenever the therapeutic dose of insulin exceeds the rate of secretion of insulin of a normal or healthy subject.

Insulin resistance is commonly observed in obese subjects. It is a major determinant of Type 2 diabetes which occurs in those subjects whose β-cells fail to compensate for insulin resistance by enhanced insulin secretion.

Insulin resistance is also associated with hyperglycemia (i.e. the subject has an elevated level of blood glucose associated with elevated levels of plasma insulin), or glucose intolerance. Those skilled in the art are aware that the term "glucose intolerance" refers to a pathological state in which there is a reduced ability to metabolise glucose, as determined by a low fasting plasma glucose level (e.g., less than about 140 mg per deciliter for a human subject) and a sustained elevated plasma glucose level in a standard glucose tolerance test. For most glucose intolerant human subjects, the plasma glucose concentration following a glucose tolerance test would generally exceed about 200 mg per deciliter for a period of at least about 30 minutes or at least about 60 minutes or at least about 90 minutes following ingestion of an amount of glucose in a standard glucose tolerance test. Glucose intolerance is seen frequently in NIDDM but also occurs with other diseases and during pregnancy. Given the role of insulin in promoting the metabolism of glucose, glucose intolerance is an end-result of insulin resistance in an NIDDM subject.

Aberrant activities of protein kinase C (PKC) isoenzymes the liver and skeletal muscle (the major regulators of glucose disposal) have been correlated to insulin resistance in humans and animal models. The PKC family consists of at least 11 isoforms, grouped into the classical PKCs (PKCα, PKCβ$_I$, PKCβ$_{II}$, PKCγ), novel PKCs (PKCδ, PKCε, PKCη, PKCθ, PKCμ), and atypical PKCs (PKCζ, PKCκ/λ), which exhibit different substrate and cofactor requirements, and differences in their tissue localization.

Intracellular lipid accumulation has also implicated in β-islet cell dysfunction, in particular loss of secretory responsiveness to glucose, and reduced β-islet cell mass due to apoptosis.

Notwithstanding the correlations between PKC activity and lipid-induced insulin resistance, the specific PKC isoenzyme(s) involved in causing insulin resistance or glucose intolerance, and the tissue-specificity of any PKC in producing such effects in the peripheral tissues, are not known. The precise mechanisms of glucose intolerance or insulin resistance remain to be elucidated for effective and highly-specific treatment regimes to be developed.

There remains a need for effective treatments of insulin resistance and/or glucose intolerance and/or hyperglycaemia, particularly in NIDDM subjects.

SUMMARY OF THE INVENTION

In work leading up to the present invention, the present inventors sought to determine whether or not PKCε is causally implicated in insulin resistance. The inventors determined the glucose tolerances of PKCε null mutant mice having their PKCε-encoding gene insertionally inactivated, and showed that the PKCε null mutant mice exhibited enhanced glucose tolerance (i.e. a lower peak of blood glucose which returned to basal levels more quickly) compared to wild type mice. This enhanced glucose tolerance was accompanied by increased plasma insulin. Surprisingly, plasma C-peptide levels were not different between wild type and null mutant chow-fed mice throughout the glucose tolerance test, indicating that the increase in insulin was due to reduced insulin clearance by the liver, rather than to enhanced insulin secretion by pancreatic β-cells.

The inventors have also shown that unsaturated fat-fed wild-type and null mutant animals exhibit similar energy intake and intra-abdominal fat accumulation. Surprisingly, in fat-fed animals, in contrast to animals receiving a normal diet, the plasma C-peptide profiles indicated that insulin secretion was enhanced in the null mutant mice, suggesting that enhanced insulin secretion contributed to the protection of the null mutant mice from lipid-induced glucose intolerance. This conclusion was further supported by a comparison of insulin secretion between chow- and fat-fed null mutant mice. In wild-type mice, however, the high fat-diet causes a β-islet cell defect in the pancreas, thereby preventing compensation of lipid-induced glucose intolerance by enhanced insulin secretion. These results therefore indicate that in addition to reduced liver-mediated clearance of insulin, deletion of PKCε also protects pancreatic β-cells from lipid-induced defects in insulin secretion.

The skilled artisan is aware from the foregoing description of the broad applicability of the invention to the treatment of subjects on a high-fat diet or showing elevated circulating lipid levels (hyperlipemia or hyperlipidemia) or having a propensity to accumulate lipid in their β-islet cells. Without being bound by any theory or mode of action, hyperglycaemia may exert a toxic effect on the β-islet cells via PKCε, because glucose can be converted by the β-islet cells into lipid.

Moreover, the present inventors observed no measurable differences in the insulin tolerances of wild-type and null mutant animals fed a high-unsaturated fat diet, and insulin resistance was only detected by more sensitive techniques such as by using glucose tracers (e.g., FIGS. 7c-e and FIG. 8). The present inventors have also shown that animal subjects receiving a diet high in saturated fats, peripheral insulin resistance occurs in both wild-type and PKCε animals. However, in neither case does PKCε inhibition e.g., by deletion of the PKCε gene or other means of reducing PKCε gene expression, appear to enhance or improve insulin action. Rather, inhibition of PKCε e.g., by deletion of the PKCε gene or other means of reducing PKCε gene expression, reduces liver-mediated clearance of insulin and protects pancreatic β-cells from lipid-induced defects in insulin secretion.

In summary, while PKCε null mutant mice do not exhibit enhanced skeletal muscle insulin sensitivity as predicted from conventional wisdom in the art, the deletion of this PKC isoform reduces insulin clearance by the liver and protects animals from fat-induced defects in insulin secretion by the pancreatic β-islet cells, thereby enhancing glucose tolerance in the whole animal.

Accordingly, the present invention provides a method of treatment of an abnormality of glucose metabolism in an animal subject, such as a human in need of treatment thereof e.g., by virtue of suffering from NIDDM, hyperglycaemia, hyperinsulinemia, insulin resistance or glucose intolerance, said method comprising administering to the subject an amount of an antagonist of a protein kinase C epsilon (PKCε) for a time and under conditions sufficient to reduce the level and/or activity of the enzyme in the liver of the subject thereby reducing insulin clearance by the liver.

In a related embodiment, there is provided a method of treatment of an abnormality of glucose metabolism in an animal subject, such as a human in need of treatment thereof e.g., by virtue of suffering from NIDDM, hyperglycaemia, hyperinsulinemia, insulin resistance or glucose intolerance or being on a high fat diet and/or displaying hyperlipidemia and/or a susceptibility to lipid deposition in β-islet cells, said method comprising administering to the subject an amount of an antagonist of a protein kinase C epsilon (PKCε) for a time and under conditions sufficient to enhance insulin secretion by the pancreas.

Also based on the findings by the inventors mat there are differential factors in the development of insulin resistance in peripheral organs such as skeletal muscle compared to internal organs such as liver and pancreas, and that PKCε is involved in insulin resistance in liver and pancreas, the inventors have developed cell-based and animal-based drug screens for identifying new classes of compounds for the treatment of insulin resistance in the liver and/or pancreas.

Accordingly, the present invention provides a method of determining an antagonist of a protein kinase C epsilon (PKCε) for the treatment of abnormal glucose metabolism in a human or animal subject said method comprising:
(i) incubating a hepatocyte in the presence and absence of a candidate compound;
(ii) stimulating the hepatocytes at (i) with insulin or analogue thereof; and
(iii) determining the rate of internalization of the insulin receptor in the insulin-stimulated hepatocytes wherein reduced insulin receptor internalization in the presence of the candidate compound compared to in the absence of the candidate compound indicates that the compound is an antagonist of PKCε.

Preferably, the hepatocyte is from a wild type animal having a functional PKCε enzyme. For example, the hepatocyte is from a non-human animal engineered to express an introduced non-endogenous PKCε gene of humans e.g., a non-human animal is engineered to have reduced or no detectable endogenous PKCε.

The hepatocyte can be a human hepatoma cell line, a primary hepatocyte or immortalized hepatocyte e.g., the hepatoma cell line HepG2 (ATCC Accession No. HB-8065) or Huh7.

For example, insulin receptor internalization can be measured by determining the uptake of labeled insulin or analogue thereof into cells and wherein reduced uptake of said labeled insulin or insulin analogue indicates that the compound is an antagonist of PKCε.

Alternatively, insulin receptor internalization is measured by a process comprising determining a change in signal produced by a pH sensitive tag in the alpha subunit of the insulin receptor relative to the signal produced by a tag in a cytoplasmic domain of the beta subunit of the insulin receptor by virtue of a change in pH of the alpha subunit on internalization. The pH sensitive tag can be pHluorin. For example, the tag in a cytoplasmic domain of the beta subunit of the insulin receptor is selected from the group consisting of FLAG epitope, yellow fluorescent protein, green fluorescent protein and red fluorescent protein e.g., at the C-terminus of the beta subunit of the insulin receptor. The pH sensitive tag is preferably positioned at the N-terminus of the alpha subunit of the insulin receptor. Preferably, the insulin receptor is an in-frame fusion protein with the pH sensitive tag and the tag in a cytoplasmic domain of the beta subunit of the insulin receptor. This embodiment clearly encompasses expressing the in-frame fusion protein in the hepatocyte. Preferably, the method further comprises introducing nucleic acid encoding the in-frame fusion protein into the hepatocyte.

Alternatively, internalization of the insulin receptor can be determined by a process comprising incubating hepatocytes in the presence of insulin, biotinylating surface proteins of the hepatocytes, and determining the total amount of insulin receptor in the hepatocytes.

Insulin receptor internalization can also be determined by labelling the insulin receptor with a fluorescent tag and determining the amount of tag internalized.

Preferably, uptake of insulin is determined as a percentage of total cell-associated insulin or analogue thereof.

The method preferably further comprises incubating the hepatocyte in the presence of a compound that inhibits or reduces the efflux of insulin or analogue thereof e.g., chloroquinone or bafilomycin.

The present invention also provides a method of determining an antagonist of a protein kinase C epsilon (PKCε) for the treatment of abnormal glucose metabolism in a human or animal subject said method comprising:
(i) incubating a pancreatic β-islet cell with an amount of a lipid or free fatty acid (FFA) and/or glucose;
(ii) incubating the cell at (i) in the presence and absence of a candidate compound; and
(iii) determining the level of insulin, secretion by the cell wherein enhanced insulin secretion in the presence of the candidate compound compared to in the absence of the compound indicates that the compound is an antagonist of PKCε.

Preferably, the islet cell is from a wild type animal having a functional PKCε enzyme. The islet cells can also be from a diabetic mouse and the islet cells are incubated in the absence of lipid or FFA. The diabetic mouse can be a db/db mouse. The islet cell can also be from a non-human animal engineered to express an introduced non-endogenous PKCε gene of humans, preferably, a non-human animal engineered to have reduced or no detectable endogenous PKCε. The islet cell can be a cultured murine MIN6 cell, a primary pancreatic islet cell or immortalized pancreatic cell line.

The cells can be pre-treated with FFA for a time and under conditions sufficient to increase in basal insulin secretion and inhibit glucose stimulated insulin secretion. The amount of FFA and/or glucose is sufficient to reduce or ablate glucose-stimulated insulin secretion by the cell in the absence of the compound being tested. The lipid or FFA can be selected from the group consisting of palmitic acid, oleic acid, linoleic acid, myristic acid, lauric acid, pentadecanoic acid, stearic acid, and linolenic acid.

The insulin secretion determined is preferably glucose-stimulated insulin secretion.

Insulin secretion is preferably determined by immunoassay using antibodies against insulin or reverse hemolytic plaque assay. Other methods are also described herein.

The method may further comprise incubating the islet cell in the presence of a compound that potentiates glucose-stimulated insulin secretion, preferably in cells having low PKCε activity, e.g., a muscarinic acid receptor agonist such as acetylcholine, a non-hydrolyzable analog of acetylcholine, arecoline, oxotremorine, pilocarpine or a mixture thereof. A preferred non-hydrolyzable analog of acetylcholine is carbamylcholine. Alternatively, the compound is an inhibitor of PI 3-kinase activity e.g., wortmannin, rosiglitazone, LY294002 or mixtures thereof. Alternatively, the compound is glyburide.

The method preferably further comprises incubating the islet cell in the presence of a compound that potentiates glucose-independent insulin secretion e.g., IBMX or forskolin or mixtures thereof.

Alternatively or in addition, the present invention provides a method of determining an antagonist of a protein kinase C epsilon (PKCε) for the treatment of abnormal glucose metabolism in a human or animal subject said method comprising providing a candidate compound to an animal having normal PKCε expression, providing a diet high in saturated and/or unsaturated fats to the animal and determining the level of one or more indicators of glucose homeostasis for the animal wherein a modified level(s) indicates that the compound is an antagonist or inhibitor of PKCε.

The animal may be a wild-type animal expressing normal endogenous levels of the PKCε enzyme, or an animal that has been engineered to express PKCε of humans (including a PKCε$^{-/-}$ or PKCε$^{+/-}$ mouse engineered to express human PKCε), or a diabetic mouse model e.g., a db/db mouse.

Preferably, a modified level of one or more indicators of glucose homeostasis is determined by comparing the level of one or more indicators of glucose homeostasis to the level of the indicators) in a wild type or PKCε$^{-/-}$ or PKCε$^{+/-}$ control animal maintained on a chow diet or other diet low in fat, wherein a trend toward the level observed for the control animal indicates modified glucose homeostasis. Preferred indicators of glucose homeostatis is selected from the group consisting of blood glucose, serum insulin, serum C peptide and combinations thereof. Preferably, the compound decreases serum glucose and/or increases serum insulin and/or increases serum C-peptide in the animal.

Preferably, an amount of the compound is provided to the animal before placing the animal on a high fat diet or at the same time as placing the animal on a high fat diet or after placing the animal on a high fat diet.

Preferably, the method further comprises determining the ability of the compound to mimic a phenotype of a PKCε$^{-/-}$ or PKCε$^{+/-}$ mouse.

Preferably, the methods described herein further comprise determining the ability of the compound to modulate activation, intracellular translocation, catalytic activity or kinase activity of PKCε.

The methods described herein can be combined in a number of different permutations and in any order, as primary, secondary or tertiary screens. In a preferred embodiment, a primary or secondary screen comprises a hepatocyte-based assay or islet cell-based assay and an animal-based assay is performed as a component of a tertiary screen to validate drug efficacy in vivo.

Accordingly, the present invention also provides a process for determining an antagonist of a protein kinase C epsilon (PKCε) for the treatment of abnormal glucose metabolism in a human or animal subject said process comprising:
(i) identifying a lead compound in a primary screen comprising incubating a hepatocyte in the presence and absence of a candidate compound, stimulating the hepatocytes at with insulin; and determining the rate of internalization of the insulin receptor in the insulin-stimulated hepatocytes wherein reduced insulin receptor internalization in the presence of the candidate compound compared to in the absence of the candidate compound indicates that the compound is a lead compound; and
(ii) incubating a pancreatic β-islet cell with an amount of a lipid or free fatty acid (FFA) such as palmitic acid and/or in the presence of an amount of glucose, incubating the cell in the presence and absence of the lead compound and determining the level of glucose-stimulated insulin secretion by the cell wherein enhanced insulin secretion in the presence of the candidate compound compared to in the absence of the compound indicates that the compound is an antagonist of PKCε.

The present invention also provides a process for determining an antagonist of a protein kinase C epsilon (PKCε) for the treatment of abnormal glucose metabolism in a human or animal subject said process comprising:
(i) identifying a lead compound in a primary screen comprising incubating a hepatocyte in the presence and absence of a candidate compound, stimulating the hepatocytes at with insulin; and determining the rate of internalization of the insulin receptor in the insulin-stimulated hepatocytes wherein reduced insulin receptor internalization in the presence of the candidate compound compared to in the absence of the candidate compound indicates that the compound is a lead compound;
(ii) incubating a pancreatic β-islet cell with an amount of a lipid or free fatty acid (FFA) such as palmitic acid and/or in the presence of an amount of glucose, incubating the cell in the presence and absence of the lead compound and determining the level of glucose-stimulated insulin secretion by the cell wherein enhanced insulin secretion in the presence of the candidate compound compared to in the absence of the compound indicates that the compound is an antagonist of PKCε; and
(iii) providing the antagonist compound identified at (ii) to an animal having normal PKCε expression, providing a diet high in saturated and/or unsaturated fats to the animal and determining the level of one or more indicators of glucose homeostasis for the animal wherein a modified level(s) indicates that the compound is an antagonist or inhibitor of PKCε in vivo.

The present invention also provides a process for determining an antagonist of a protein kinase C epsilon (PKCε) for the treatment of abnormal glucose metabolism in a human or animal subject said process comprising:
(i) identifying a lead compound in a primary screen comprising incubating a pancreatic β-islet cell with an amount of a lipid or free fatty acid (FFA) such as palmitic acid and/or in the presence of an amount of glucose, incubating the cell in the presence and absence of a candidate compound and determining the level of glucose-stimulated insulin secretion by the cell wherein enhanced insulin secretion in the presence of the candidate compound compared to in the absence of the compound indicates that the compound is a lead compound; and
(ii) incubating a hepatocyte in the presence and absence of the lead compound, stimulating the hepatocytes at with insulin; and determining the rate of internalization of the insulin receptor in the insulin-stimulated hepatocytes wherein reduced insulin receptor internalization in the presence of the lead compound compared to in the absence of the lead compound indicates that the compound is an antagonist of PKCε.

The present invention also provides a process for determining an antagonist of a protein kinase C epsilon (PKCε) for the treatment of abnormal glucose metabolism in a human or animal subject said process comprising:
(i) identifying a lead compound in a primary screen comprising incubating a pancreatic β-islet cell with an amount of a lipid or free fatty acid (FFA) such as palmitic acid and/or in the presence of an amount of glucose, incubating the cell in the presence and absence of a candidate compound and determining the level of glucose-stimulated insulin secretion by the cell wherein enhanced insulin secretion in the presence of the candidate compound compared to in the absence of the compound indicates that the compound is a lead compound;
(ii) incubating a hepatocyte in the presence and absence of the lead compound, stimulating the hepatocytes at with insulin; and determining the rate of internalization of the insulin receptor in the insulin-stimulated hepatocytes wherein reduced insulin receptor internalization in the presence of the lead compound compared to in the absence of the lead compound indicates that the compound is an antagonist of PKCε; and
(iii) providing the antagonist compound identified at (ii) to an animal having normal PKCε expression, providing a diet high in saturated and/or unsaturated fats to the animal and determining the level of one or more indicators of glucose homeostasis for the animal wherein a modified level(s) indicates that the compound is an antagonist or inhibitor of PKCε in vivo.

The present invention also provides a method for determining a compound that specifically antagonizes a protein kinase C epsilon (PKCε) in a hepatocyte comprising:
(i) incubating a hepatocyte and an insulin-responsive cell other than a hepatocyte in the presence and absence of a candidate compound;
(ii) stimulating the hepatocyte and the other insulin-responsive cell at (i) with insulin; and
(iii) determining the rate of internalization of the insulin receptor in the insulin-stimulated hepatocytes wherein reduced insulin receptor internalization in the presence of the candidate compound compared to in the absence of the candidate compound in the hepatocyte but not in the other insulin-responsive cell indicates that the compound specifically antagonizes a PKCε in a hepatocyte.

Preferably, the other insulin responsive cell is a muscle cell or an adipocyte.

The methods and processes described herein may further comprise testing the compound for its ability to inhibit the activity of a recombinant PKCε protein or bind to a recombinant PKCε protein in a cell that has been transfected with nucleic acid encoding the PKCε protein.

In performing the methods and/or processes described herein it is preferred for the antagonist of PKCε to mimic a phenotype in the liver and/or pancreas of an animal having reduced PKCε activity by virtue of the endogenous PKCε gene of said animal being deleted or inactivated by mutation.

The present invention also provides for the use of a vector capable of expressing a polypeptide antagonist or oligonucleotide antagonist of a protein kinase C epsilon (PKCε) in a format suitable for introduction into a hepatocyte or pancreatic β-islet cell and expression therein in medicine.

The present invention also provides for the use of an isolated hepatocyte or pancreatic β-islet cell comprising introduced nucleic acid encoding a polypeptide antagonist or oligonucleotide antagonist of PKCε in medicine.

The present invention also provides for the use of a non-human transformed animal having reduced PKCε activity by virtue of the endogenous PKCε gene of said animal being deleted or inactivated by mutation in the determination of glucose homeostasis in the animal.

The present invention also provides for the use of a hepatocyte or pancreatic islet cell from a non-human transformed animal having reduced PKCε activity by virtue of the endogenous PKCε gene of said animal being deleted or inactivated by mutation for the determination of insulin receptor internalization, insulin uptake or glucose-stimulated insulin secretion by the hepatocyte or pancreatic islet cell.

The present invention also provides a non-human transformed animal having reduced endogenous PKCε activity by virtue of the endogenous PKCε gene of said animal being deleted or inactivated by mutation and comprising an introduced PKCε gene of humans. The invention clearly extends to a progeny animal of the non-human transformed animal wherein said progeny animal comprises the introduced PKCε gene of humans. The present invention also encompasses an isolated cell from the non-human transformed animal e.g., a hepatocyte or pancreatic islet cell.

BRIEF DESCRIPTION OF THE DRAWINGS

FIG. 2b is a copy of a photographic representation of western immunoblots, showing the levels of the PKC isoforms PKCα, PKCδ, PKCθ and PKCε, in the cytosolic (C) and solubilised membrane (M) fractions of skeletal muscle from the chow-fed and unsaturated fat-fed mice described in the legend to FIG. 2a.

FIG. 4b is a copy of a photographic representation of western immunoblots, showing the levels of the PKC isoforms PKCα, PKCδ, PKCθ and PKCε, in the cytosolic (C) and solubilised membrane (M) fractions of skeletal muscle from the chow-fed and unsaturated fat-fed mice described in the legend to FIG. 4a.

FIG. 4c is a graphical representation showing the quantification of PKCα in immunoblots in the cytosolic and solubilised membrane fractions of skeletal muscle from the chow-fed and saturated fat-fed mice described in the legend to FIG. 4b. Data are expressed as a percentage of the average level of PKCα in the cytosol of wild-type mice receiving a chow diet. The x-axis shows the genotype of mice and the diet received (i.e., chow or fat). Open bars are cytosolic fraction. Filled bars are solubilised membrane fractions. The means from 5-6 mice per group are shown.

FIG. 4d is a graphical representation showing the quantification of PKCδ in immunoblots in the cytosolic and solubilised membrane fractions of skeletal muscle from the chow-fed and saturated fat-fed mice described in the legend to FIG. 4b. Data are expressed as a percentage of the average level of PKCδ in the cytosol of wild-type mice receiving a chow diet. The x-axis shows the genotype of mice and the diet received (i.e., chow or fat). Open bars are cytosolic fraction. Filled bars are solubilised membrane fractions. The means from 5-6 mice per group are shown.

Figure 10A:
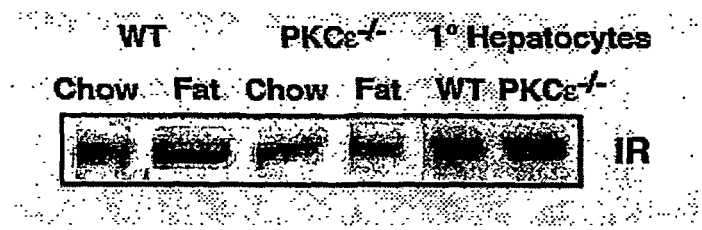
FIG. 10a is a copy of a photographic representation of an immunoblot showing expression of the insulin receptor (IR) in liver extracts from chow-fed and unsaturated diet-fed mice maintained as described in the legend to FIG. 2a (first 4 columns), and in the lysates of isolated primary (1°) hepatocytes from chow-fed mice. Data show no significant differences in IR levels.
Figure 10B:
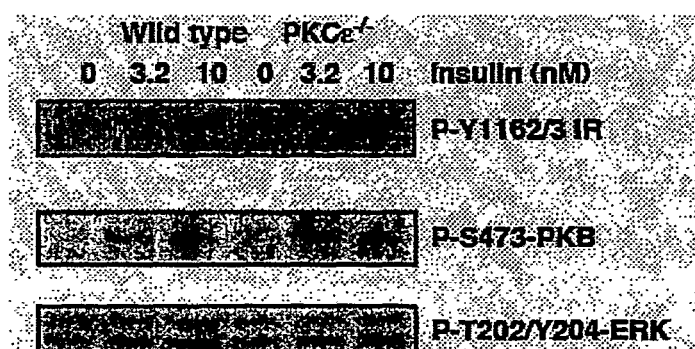
FIG. 10b is a copy of a photographic representation of immunoblots showing similar downstream signalling from the insulin receptor (IR) in primary hepatocytes from wild type and PKCε$^{-/-}$ mice, as determined by measuring the level of (i) tyrosine phosphorylation of the insulin receptor (P-Y1162/3 IR), (ii) serine phosphorylation of protein kinase B (P-S473-PKB) phosphorylation, and (iii) phosphorylation of a MAP kinase (P-T202/Y204-ERK), in the absence of insulin (O), or following incubation in the presence of 3.2 nM insulin or 10 nM insulin. Data show phosphorylation of the IR after 2 min, phosphorylation of PKB and ERK after 10 mins in both wild type and PKCε$^{-/-}$ mice.

Quantification of serine phosphorylation of protein kinase B (P-S473-PKB) in primary hepatocytes from FIG. 10b following insulin stimulation was performed. The immunoblot shown in row 2 of FIG. 10b was subjected to densitometry, and data corrected for total protein loading. Data indicated no differences in phosphorylated PKB between PKCε$^{-/-}$ mice (KO) and wild-type (WT) mice under each condition. ANOVA: P<0.015 for effect of insulin.

Quantification of threonine/tyrosine phosphorylation of the MAP kinase ERK (P-T202/Y204-ERK) in primary hepatocytes from FIG. 10b following insulin stimulation was performed. The immunoblot shown in row 3 of FIG. 10b was subjected to densitometry, and data corrected for total levels of signaling proteins. Data indicated no differences in phosphorylated ERK between PKCε$^{-/-}$ mice (KO) and wild-type (WT) mice under each condition. ANOVA: P<0.0075 for effect of insulin.

Figure 12:
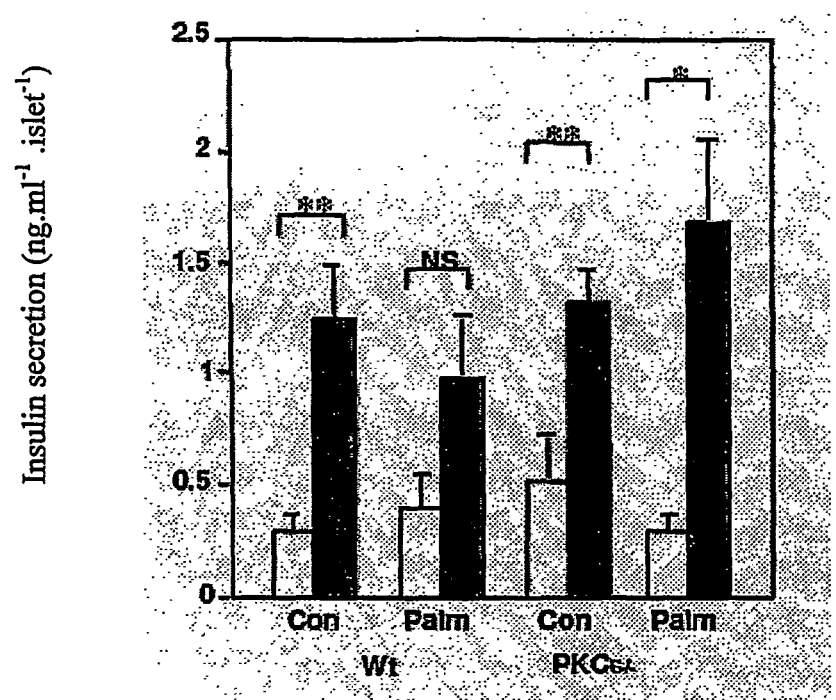

FIG. 12 is a graphical representation showing glucose-stimulated insulin secretion by pancreatic islets pretreated in the absence (Con) or presence (Palm) of palmitate (n=3 per group). Open bars represent islets incubated in 2.8 mM glucose. Filled bars represent islets incubated in the presence of 16.7 mM glucose, t-test, * P<0.05, ** P<0.01, for 16.7 mM glucose versus 2.8 mM glucose. Data indicate that, in the presence of palmitate at 16.7 mM glucose, an inhibitor of PKCε is detectable by virtue of reproducing the effect seen in PKCε$^{-/-}$ mice, whereas a compound that does not inhibit PKCε under those conditions has a reduced level of insulin secretion comparable to that seen in wild-type islets.

Figure 13:
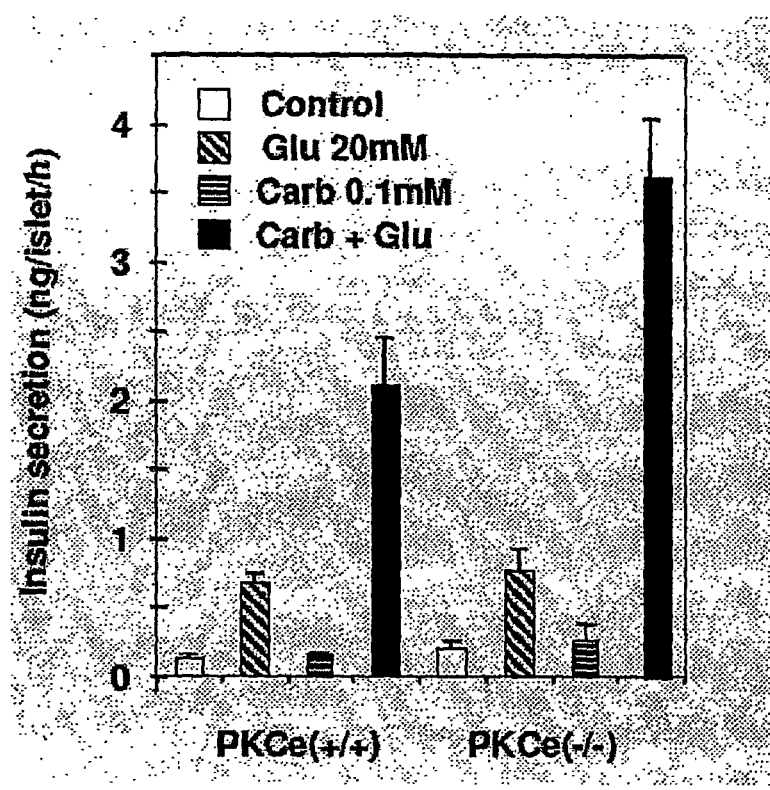

FIG. 13 is a graphical representation showing the potentiation of glucose-stimulated insulin secretion from pancreatic islets by the cholinergic muscarinic receptor agonist carbamylcholine. Insulin secretion by islets isolated from wild type (PKCε$^{+/+}$) and PKCε null mutant (PKCε$^{-/-}$) mice was measured in the absence of glucose (open bars), or in the presence of 20 mM glucose (diagonally hatched bars), 0.1 mM carbamylcholine (horizontally hatched bars), or in the presence of both 20 mM glucose and 0.1 mM carbamylcholine (filled bars). Enhanced insulin secretion from PKCε$^{-/-}$ islets compared to wild type islets indicates that inhibitors of PKCε can be assayed by measuring glucose-stimulated insulin secretion from islet cells incubated in the presence of a muscarinic acid receptor agonist such as, for example, carbamylcholine. PKCε inhibitors identified in such a screen would improve glucose tolerance by augmenting the cephalic phase of insulin secretion mediated by the release of acetylcholine from vagal efferent neurons on pancreatic β-islet cells.

DETAILED DESCRIPTION OF THE INVENTION

Methods for Identifying Antagonists of PKCε
1. Hepatocyte-Based Assays

The present invention provides a method of determining an antagonist of a protein kinase C epsilon (PKCε) for the treatment of abnormal glucose metabolism in a human or animal subject said method comprising:
(i) incubating a hepatocyte in the presence and absence of a candidate compound;
(ii) stimulating the hepatocytes at (i) with insulin or analogue thereof; and
(iii) determining the rate of internalization of the insulin receptor in the insulin-stimulated hepatocytes wherein reduced insulin receptor internalization in the presence of the candidate compound compared to in the absence of the candidate compound indicates that the compound is an antagonist of PKCε.

For the present purpose, any hepatocyte that expresses a functional PKCε enzyme can be used. This can be a naturally-occurring hepatocyte such as, for example, from a wild-type mouse or diabetic or obese mouse (see Example 2), or one produced by transfection of nucleic acid encoding the enzyme. Such transfected hepatocytes are preferably derived from $PKC\epsilon^{-/-}$ or $PKC\epsilon^{+/-}$ animals with an introduced PKCε gene, especially the human gene.

Preferably, the hepatocyte is a human hepatoma cell line such as, for example, HepG2 (ATCC Accession No. HB-8065), Huh7, or a primary hepatocyte such as, for example, a primary murine, rat or human hepatocyte.

Immortalized hepatocytes from wild-type mice or $PKC\epsilon^{-/-}$ mice or from $PKC\epsilon^{-/-}$ mice having an introduced human PKCε gene, are particularly preferred because they are subject to less variation between cells than primary hepatocytes. To produce immortalized cells, primary hepatocytes are obtained from the livers of neonates, and immortalized by transfection with a retroviral vector expressing human telomerase reverse transcriptase (hTERT) essentially as described by Wang and Harris (WO 02/48319 published 20 Jun. 2002). Alternatively, hepatocytes are obtained by transfection with ras-transformed simian virus 40 (SV40) or culturing in the presence of SV40 large T-antigen and selecting for clones that grow in culture.

Insulin receptor internalization can be measured, for example, by determining the uptake of labeled insulin (e.g. fluorescently labelled insulin, biotinylated insulin, or radiolabelled insulin such as $^{125}$I-Insulin or $^{123}$I-insulin) or analogue thereof into cells, preferably as a percentage of total cell-associated insulin or analogue.

Alternatively, internalization is assayed by expressing the insulin receptor in cells as a dual-tagged protein such that a first tag, e.g., FLAG epitope or yellow fluorescent protein (YFP) or green fluorescent protein (GFP) or red fluorescent protein (RFP), is positioned at or near the C-terminal portion of the protein that ultimately resides in the cytosol and a second pH-sensitive tag (e.g., pHluorin) is positioned at or near the N-terminal portion of the protein that ultimately resides in the extracellular space, and determining receptor internalization by measuring the change in signal produced by the second pH sensitive tag relative to the first tag by virtue of the change in pH on internalization. A suitable pH sensitive tag for this purpose is pHluorin, which is known in the art as a pH-sensitive mutant of green fluorescent protein (Miesenbock et al, *Nature* 394, 192-195, 1998, incorporated herein in its entirety).

More particularly, an insulin receptor double fusion protein is expressed ectopically in liver cells (e.g. HepG2, HuH7, primary hepatocytes), by transfecting the cells with nucleic acid encoding the insulin receptor fusion protein using hepadnavirus-mediated or adenovirus-mediated transfection. Those skilled in the art are aware that the insulin receptor (IR) (Ullrich et al., 1985, Nature 313:756-61) is the prototype for a family of receptor protein tyrosine kinases (RPTKs) that are structurally defined as a heterotetrameric species of two alpha and two beta subunits wherein the alpha and beta subunits are produced by processing of a single precursor polypeptide and wherein the beta subunit comprises the transmembrane and intracellular domain(s) and the alpha subunit comprises the extracellular domain. Accordingly, a protein-encoding region of a YFP gene (NCBI Accession No. AY613998) or GFP gene (NCBI Accession No, AY613996) or RFP gene (NCBI Accession No. AY613997) is cloned in-frame into an intracellular domain-encoding portion, e.g., downstream or within to the C-terminal-encoding portion, of nucleic acid encoding the insulin receptor precursor polypeptide (NCBI Accession No, X02160) using standard techniques in the art. Similarly, a protein-encoding region of a pHluorin gene (NCBI Accession No. AY533296 or AF058695 or AF058694) is cloned in-frame into an extracellular domain-encoding portion, e.g., upstream or within the N-terminal-encoding portion, of nucleic acid encoding the insulin receptor precursor polypeptide. The cDNA for this construct is in the form of one gene, which yields both subunits upon post-transcriptional processing. The recombinant nucleic acid construct is introduced to a suitable expression vector and transfected into hepatocytes such that the insulin receptor fusion polypeptide is processed into labelled alpha and labelled beta subunits, wherein the label on the extracellular alpha subunit e.g., at the alpha subunit N-terminus, is the pH-sensitive pHluorin peptide and the label on the intracellular beta subunit is another fluorescent tag such as YFP or RFP or GFP, e.g., at the beta subunit C-terminus. In unstimulated cells, the pHluorin is exposed to the extracellular medium (pH 7.4). Upon insulin binding, the receptor is internalised, and the pHluorin becomes situated in the lumen of an endocytotic vesicle, which then becomes an endosome. Upon acidification (to ≤pH 6) of the endosome (the normal process driven by an $H^+$/ATPase, which promotes insulin dissociation from the receptor and subsequent insulin degradation), the fluorescent signal from the pHluorin is modified, whereas the signal from the YFP or GFP or RFP, which remains exposed to the cytosol, is constant. Thus, the level of fluorescence from the beta subunit C terminal tag provides a measure of total insulin receptor, whereas the level of fluorescence from the alpha subunit N-terminal tag provides a measure of the amount of receptor that is internal. Accordingly, internalization of the receptor is measured in the transfected cells as a change in ratio of the two signals, determined by fluorescence confocal microscopy. To enhance or increase a modified ratio in the signals between samples, insulin efflux is reduced or inhibited by incubating the cells in an amount of chloroquine or bafilomycin sufficient to reduce or inhibit receptor recycling (e.g., Balbis et al., *J. Biol. Chem.* 279, 12777-12785, 2004 which is incorporated herein by reference).

Alternatively, internalization of the insulin receptor is determined by immunoassay and/or labelling the receptor with biotin (e.g., Balbis et ah, *J. Biol. Chem.* 279. Mill-12785, 2004 which is incorporated herein by reference). For example, hepatocytes are incubated in the presence or absence of insulin for different times e.g., time zero and at times up to about 15 min. Thereafter, hepatocytes are washed, and cell surface proteins are biotinylated by incubation with a cross-linking reagent such as Sulfo-NHS-LC-Biotin. Biotinylated and non-biotinylated insulin receptor are immunoprecipitated from total cell lysates and detected in an immunoassay e.g., western blot or ELISA or radioimmunoassay using anti-insulin receptor antibody, to provide a measure of total insulin receptor. A streptavidin-conjugated horseradish peroxidase is also used to detect biotinylated insulin receptor associated with the plasma membrane at each time point. The ratio of biotinylated insulin receptor to the total amount of receptor is determined, as an indication of internalization. To enhance or increase the change in this ratio, insulin efflux is reduced or inhibited by incubating the cells in ah amount of chloroquine or bafilomycin sufficient to reduce or inhibit receptor recycling Such measurements provide a good approximation of insulin receptor internalization, because the receptor internalizes when associated with insulin or an analogue thereof and because free insulin is not taken into the cells.

In performing this assay platform, the rate of insulin or insulin analogue uptake is preferably, determined over a period of time for which uptake in the cell is shown to be linear, and then compared in the presence and absence of the candidate compound, wherein a modified rate of uptake by the cells indicates that the compound has modulatory activity with respect to internalization. It will be apparent that this embodiment applies mutatis mutandis to a method a method of determining an antagonist of a protein kinase C epsilon (PKCε) for the treatment of abnormal glucose metabolism in a human or animal subject said method comprising:
(i) incubating a hepatocyte in the presence and absence of a candidate compound;
(ii) stimulating the hepatocytes at (i) with insulin or analogue thereof; and
(iii) determining the rate of insulin uptake in the insulin-stimulated hepatocytes wherein reduced insulin uptake in the presence of the candidate compound compared to in the absence of the candidate compound indicates that the compound is an antagonist of PKCε.

Insulin receptor internalization can also be measured by labelling the receptor with a fluorescent tag essentially as described by Carpentier et al. Journal of Cell Biology, 122, 1243-1252, 1993, or Hsu et al., Endocrinology, 134, 744-750, 1994.

By "insulin analogue" is meant a variant of insulin or other compound haying the receptor activating function of insulin i.e., it can bind to the insulin receptor and result in internalization of the insulin receptor. A preferred insulin analogue is Insulin lispro (Humalog), which is a polypeptide comprising the amino acid sequence of native insulin wherein the amino acids at positions 28 and 29 on the insulin B-chain are reversed (i.e., Lys(B28), Pro(B29) human insulin analog).

In performing the various embodiments of the invention, the signal:noise ratio of the assay is enhanced, such as, for example, by incubating the hepatocyte in the presence of a compound that reduces potentiates insulin uptake e.g., in wild-type cells. By reducing background the ability to detect enhanced insulin uptake into hepatocytes in the presence of an antagonist of PKCε activity is improved.

It is also within the scope of the present invention to further enhance the total level of insulin or insulin analogue in hepatocytes by inhibiting or reducing efflux of insulin or analogue thereof during the assay. Because the level of uptake in the assay is expressed as a proportion of total insulin or analogue in the cells, including media, insulin efflux may reduce the signal:noise ratio, by virtue of their being more label outside the cells than would be the case if efflux was inhibited. Accordingly, the present invention clearly encompasses further incubating the hepatocytes in the presence of an inhibitor of insulin efflux such as, for example, chloroquinone or bafilomycin.

The present invention clearly encompasses the use of any in silico analytical method and/or industrial process for carrying the hepatocyte-based screening method described herein into a pilot scale production or industrial scale production of an inhibitory compound identified in such screens. This invention also provides for the provision of information for any such production. Accordingly, the screening assays are further modified by:
(i) optionally, determining the structure of the compound; and
(ii) providing the compound or the name or structure of the compound such as, for example, in a paper form, machine-readable form, or computer-readable form.

Naturally, for compounds that are known albeit not previously tested for their function using a screen provided by the present invention, determination of the structure of the compound is implicit. This is because the skilled artisan will be aware of the name and/or structure of the compound at the time of performing the screen.

As used herein, the term "providing the compound" shall be, taken to include any chemical or recombinant synthetic means for producing said compound or alternatively, the provision of a compound that has been previously synthesized by any person or means. This clearly includes isolating the compound.

In a preferred embodiment, the compound or the name or structure of the compound is provided with an indication as to its use e.g., as determined by a screen described herein.

The diagnostic assays can be further modified by:
(i) optionally, determining the structure of the compound;
(ii) optionally, providing the name or structure of the compound such as, for example, in a paper form, machine-readable form, or computer-readable form; and
(iii) providing the compound.

In a preferred embodiment, the synthesized compound or the name or structure of the compound is provided with an indication as to its use e.g., as determined by a screen described herein;

2. Islet Cell-Based Assays

The present invention also provides a method of determining an antagonist of 3 protein kinase C epsilon (PKCε) for the treatment of abnormal glucose metabolism in a human or animal subject said method comprising:
(i) incubating a pancreatic β-islet cell with an amount of a lipid or free fatty acid (FFA) and/or glucose;
(ii) incubating the cell at (i) in the presence and absence of a candidate compound; and
(iii) determining the level of insulin secretion by the cell wherein enhanced insulin secretion in the presence of the candidate compound compared to in the absence of the compound indicates that the compound is an antagonist of PKCε.

For the present purpose, any islet cell that expresses a functional PKCε enzyme can be used. This can be a naturally-occurring islet cell such as, for example, from a wild-type mouse or diabetic or obese mouse (see Example 3), or one produced by transfection of nucleic acid encoding the enzyme. Such transfected islets are preferably derived from $PKC\epsilon^{-/-}$ or $PKC\epsilon^{-/-}$ animals having an introduced PKCε gene, especially the human gene.

Pre-treatment of islet cells (e.g., for about 48 hours in the case of MIN6 cells) in lipid or FFA leads to an increase in basal insulin secretion and an inhibition of glucose stimulated insulin secretion. Preferably, the amount of FFA and/or glucose is sufficient to reduce or ablate glucose-stimulated insulin secretion by the cell in the absence of the compound being tested.

Preferably the lipid or FFA is selected from the group consisting of palmitic acid, oleic acid, linoleic acid, myristic acid, lauric acid, pentadecanoic acid, stearic acid, and linolenic acid.

Preferably, the islet cell is a cultured murine MIN6 cell or an isolated human, rat or murine pancreatic islet cell or an immortalized pancreatic cell line.

Immortalized islet cells from wild-type mice or PKCε$^{-/-}$ mice are particularly preferred because they are subject to less variation between cells than primary islets. To produce immortalized cells, primary islets are obtained from the pancreata of neonates, and immortalized by transfection with a retroviral vector expressing human telomerase reverse transcriptase (hTERT) essentially as described by Wang and Harris (WO 02/48319 published 20 Jun. 2002). Alternatively, islets are obtained by transfection with ras-transformed simian virus 40 (SV40) or culturing in the presence of SV40 large T-antigen and selecting for clones that grow in culture.

Preferably, the insulin secretion is glucose-stimulated insulin secretion. However, the present invention clearly encompasses the use of other means to stimulate insulin secretion in the context of assaying for inhibitors of insulin secretion in islet cells. For example, wild-type islets are also known to be stimulated by KCl in the presence or absence of diazoxide. Diazoxide is a selective inhibitor of the $Ca^{2+}$ arm of glucose-stimulated insulin secretion, KCl can substitute for this arm (in a manner not inhibited by diazoxide). Thus, the combination of glucose plus KCl plus diazoxide unmasks the $K^+$ ATP-channel independent pathway of glucose-stimulated insulin secretion.

Insulin secretion by individual beta cells isolated from mice or from normal rats is also capable of being assayed using, for example, a reverse hemolytic plaque assay. Pancreata are harvested from female Wistar-Furth rats, the pancreatic islets isolated, and dispersed into single cells which are mixed with protein A-coated ox erythrocytes, placed in a Cunningham chamber in the presence of insulin antiserum, and exposed to candidate inhibitors. Hemolytic plaques develop around the insulin-secreting cells in the presence of complement, and the percentage of plaque-forming cells is determined and the plaque areas (reflecting the amount of insulin secreted) are quantitated. Plaque-forming (but not nonplaque-forming) cells are also identified as insulin secreting by an independent immunofluorescent technique. Negative control reactions for which no plaques form in the absence of inhibitor compound can also be established such as, for example, (i) deletion of insulin antiserum from the preparation; (ii) preabsorption of insulin antiserum with insulin; (iii) incubation with non-protein A-coated red blood cells (RBC); and (iv) omission of complement In performing this assay, the percentage of plaque-forming cells and the mean plaque are increased by exposure to glucose (0.75-20 mM) in a concentration-dependent manner over at least about 60 min incubation time.

Secretion can also be measured indirectly as an increase in the islet surface area, due to fusion of granule membrane with the plasma membrane. For example, changes in capacitance as determined by patch clamping methods can be used to determine changes in islet surface area.

The present invention clearly encompasses high throughput assays. For example, reporter assays for measuring secretion that are amenable to high-throughput screening include transfection of islet cells with growth hormone (GH) and monitoring GH release as a surrogate for insulin, by radioimmunoassay (RIA) or ELISA. Alternatively, cells are transfected with fluorescently-tagged protein, such as a transmembrane protein e.g., phogrin, that is targeted to a secretory granule and co-released with insulin, or fused to the plasma membrane during exocytosis. Enhanced fluorescence in medium (or on the plasma membrane) is proportional to secretion. Such assays are modified by using a pH-sensitive fluorescent tag e.g., pHluorin, as described herein above, such that a change in flourescence occurs when the intragranular space (low pH) comes into contact with the extracellular space (neutral pH) during fusion of granules with the plasma membrane during exocytosis.

Preferably, the islet cell is also incubated in the presence of a compound that potentiates glucose-stimulated insulin secretion, especially in cells having low or reduced PKCε expression, e.g., a muscarinic acid receptor agonist such as, for example, acetylcholine, a non-hydrolyzable analog of acetylcholine e.g., carbamylcholine, arecoline, oxotremorine and pilocarpine. Carbamylcholine and other analogues of acetylcholine are particularly useful. Compounds that inhibit PI 3-kinase activity are also useful for potentiating glucose-stimulated insulin secretion by islet cells, such as for example wortmannin, rosiglitazone or LY294002, Glyburide is also capable of being employed for this purpose. Exposure of islet cells to 100 nM glyburide in the presence of 20 mM glucose enhances insulin secretion by an effect directly on pancreatic beta cells.

Glucose-independent insulin secretion is potentiated using IBMX and/or forskolin.

The present invention clearly encompasses the use of any in silico analytical method and/or industrial process for carrying the islet cell-based screening method described herein into a pilot scale production or industrial scale production of an inhibitory compound identified in such screens. This invention also provides for the provision of information for any such production. Accordingly, the screening assays are further modified by:
(i) optionally, determining the structure of the compound; and
(ii) providing the compound or the name of structure of the compound such as, for example, in a paper form, machine-readable form, or computer-readable form.

Naturally, for compounds that are known albeit not previously tested for their function using a screen provided by the present invention, determination of the structure of the compound is implicit. This is because the skilled artisan will be aware of the name and/or structure of the compound at the time of performing the screen.

As used herein, the term "providing the compound" shall be taken to include any chemical or recombinant synthetic means for producing said compound or alternatively, the provision of a compound that has been previously synthesized by any person or means. This clearly includes isolating the compound.

In a preferred embodiment, the compound or the name or structure of the compound is provided with an indication as to its use e.g., as determined by a screen described herein.

The diagnostic assays can be further modified by:
(i) optionally, determining the structure of the compound;
(ii) optionally, providing the name or structure of the compound such as, for example, in a paper form, machine-readable form, or computer-readable form; and
(iii) providing the compound.

In a preferred embodiment, the synthesized compound or the name or structure of the compound is provided with an indication as to its use e.g., as determined by a screen described herein.

3. Animal-Based Assays

The present invention also provides a method of determining an antagonist of a protein kinase C epsilon (PKCε) for the treatment of abnormal glucose metabolism in a human or animal subject said method comprising providing a candidate compound to an animal having normal PKCε expression, providing a diet high in saturated and/or unsaturated fats to the animal and determining the level of one or more indicators of glucose homeostasis for the animal wherein a modified level(s) indicates that the compound is an antagonist or inhibitor of PKCε.

The animal having normal PKCε expression can be any wild type animal with respect to PKCε activity. Alternatively, the animal is a PKCε$^{-/-}$ animal having an introduced PKCε gene, especially the human gene. It will be apparent to the skilled artisan from the disclosure herein that such "humanised" animals provide a means of validating an antagonist identified in the screens of the present invention for its ability to antagonize the activity of the human PKCε enzyme. Such animals also provide a source of "humanized" hepatocytes and islet cells.

A modified level of one or more indicators of glucose homeostatis may be determined, for example, by comparing the level of one or more indicators of glucose homeostasis in a wild type animal to the level of the indicators) in PKCε$^{-/-}$ or PKCε$^{+/-}$ control animal maintained on a chow diet or other diet low in fat, wherein a trend toward the level observed for the control animal indicates modified glucose homeostasis. It is to be understood that the level of the indicator(s) for the control animal may also be intermediate between the level determined for the wild type animal receiving the compound and a wild type animal not receiving the compound and yet be considered to exhibit "a trend toward the level observed for the control animal". Preferred indicators of glucose homeostasis are selected from the group consisting of blood glucose, serum insulin, serum C peptide, decrease fasting insulin and glucose levels, glucose excursions following a glucose tolerance test, and increased insulin and/or c-peptide levels during the glucose tolerance test. Preferably, the compound will enhance or increase serum glucose and/or serum insulin and/or serum C-peptide levels.

In performing this embodiment of the invention, it is preferred to provide an amount of the compound to the animal for a time and under conditions sufficient to protect against the effects of the high fat diet, such as, for example, by commencing the administration of compound before placing the animal on a high fat diet. To assay for the ability of the compound to reduce insulin clearance by the liver, it is preferred to administer the compound at the same time as placing the animal on a high fat diet, or more preferably, after placing the animal on a high fat diet.

Preferably, the effect of the compound on the animal is determined by virtue of its ability to mimic a phenotype of the PKCε$^{-/-}$ or PKCε$^{+/-}$ mouse. For example, PKCε activity or sub-cellular localization of PKCε in the liver and/or pancreas of the animal may be determined. Hepatocytes and/or islet cells may also be obtained from the animal following administration of the compound and assayed in the cell-based assays described herein to determine long term effects of the compound on cellular function.

Based on the data provided herein for the PKCε$^{-/-}$ mouse, the skilled artisan is readily able to conduct such experimentation without the exercise of inventive effort.

It is also within the scope of the present invention to further test for adverse effects of a compound on the test animals.

The present invention clearly encompasses the use of any in silico analytical method and/or industrial process for carrying the animal-based screening method described herein into a pilot scale production or industrial scale production of an inhibitory compound identified in such screens. This invention also provides for the provision of information for any such production. Accordingly, the screening assays are further modified by:
(i) optionally, determining the structure of the compound; and
(ii) providing the compound or the name or structure of the compound such as, for example, in a paper form, machine-readable form, or computer-readable form.

Naturally, for compounds that are known albeit not previously tested for their function using a screen provided by the present invention, determination of the structure of the compound is implicit. This is because the skilled artisan will be aware of the name and/or structure of the compound at the time of performing the screen.

As used herein, the term "providing the compound" shall be taken to include any chemical or recombinant synthetic means for producing said compound or alternatively, the provision of a compound that has been previously synthesized by any person or means. This clearly includes isolating the compound.

In a preferred embodiment, the compound or the name or structure of the compound is provided with an indication as to its use e.g., as determined by a screen described herein.

The diagnostic assays can be further modified by:
(i) optionally, determining the structure of the compound;
(ii) optionally, providing the name or structure of the compound such as, for example, in a paper form, machine-readable form, or computer-readable form; and
(iii) providing the compound.

In a preferred embodiment, the synthesized compound or the name or structure of the compound is provided with an indication as to its use e.g., as determined by a screen described herein.

4. Other Readout Systems for Assaying Inhibition of PKCε

Inhibitors of PKCε can also be identified using assays that measure the activation, intracellular translocation, binding to intracellular receptors (e.g. RACKs) or catalytic activity of PKCε. Traditionally, the kinase activity of PKC family members has been assayed using at least partially purified PKC in a reconstituted phospholipid environment with radioactive ATP as the phosphate donor and a histone protein or a short peptide as the substrate (Kitano et al., Meth. Enzymol. 124, 349-352, 1986; Messing et al., J. Biol. Chem. 266, 23428-23432, 1991). Recent improvements include a rapid, highly sensitive chemiluminescent assay that measures protein kinase activity at physiological concentrations and can be automated and/or used in high-throughput screening (Lehel et al., Anal. Biochem. 244, 340-346, 1997) and an assay using PKC in isolated membranes and a selective peptide substrate that is derived from the MARCKS protein (Chakravarthy et al. Anal. Biochem. 196, 144-150, 1991).

The present invention also encompasses assays wherein modified expression of one or more PKCε-regulated genes is determined.

Inhibitors that affect the intracellular translocation of PKCε are identified by assays in which the intracellular localization of PKCε is determined by fractionation (Messing et al., J. Biol. Chem. 266, 23428-23432, 1991), or by immunohistochemical means (U.S. Pat. No. 5,783,405; U.S. patent application Ser. No. 08/686,796). Monoclonal and polyclonal antibodies useful for such immunohistochemical assays, that bind specifically to human, rat or murine PKCε, are publicly available (e.g., United States Biological, Swampscott, Mass. 01907, USA). For example, PKCε localization can be determined by confocal microscopy. Immunofluorescence is also useful for determining the localization of PKCε in hepatocytes, especially in plasma membrane and early endosomes, which is consistent with a role in insulin receptor (IR) endocytosis. Alternatively, a PKCε-GFP fusion protein can be employed.

5. Validation of PKCε Antagonists

Validation of the activity of any candidate PKCε antagonist is primarily achieved by ensuring efficacy of the compound in isolated hepatocytes and pancreatic islet cells and optionally, in animals, as described herein above.

Additionally, various surrogate assays to validate efficacy of the compounds can be performed. For example, assays can be performed using recombinant PKCε e.g., produced by transfection of nucleic acid encoding wild type PKCε or a constitutively active variant thereof e.g., a kinase-dead PKCε variant, PKCε (A159E) and/or PKCε (K437R), in a baculovirus expression system in insect cells (Hug and Sarre, Biochem. J. 291, 329-343, 1993; Koide et at., Proc. Natl. Acad. Sci. USA 89, 1149-1153, 1992; and Kazanietz et al., Mol. Pharm. 44, 298-307, 1993 which are incorporated by reference herein). To facilitate purification of the recombinant PKCε protein, it is preferred to express the protein as a fusion protein with a detectable ligand such as, for example, a hexahistidine peptide or FLAG epitope.

The selectivity of a PKCε antagonist is generally determined by comparing the effect of the inhibitor on PKCε to its effect on other PKC isozymes similarly expressed in transfected cells.

Alternative surrogate assays may employ hepatocytes or islet cells that overexpress wild type PKCε or a constitutively activated variant thereof or PKCε analogue lacking an active kinase domain (i.e., a "kinase-dead variant"), stimulated with ligands and activators such as insulin, glucagon, norepinephrine and phorbol esters, and combinations thereof, or alternatively, lysates/extracts thereof. For example, specificity of a candidate PKCε antagonist for activity in particular cell type, such as hepatocyte and/or pancreas, but not for a skeletal muscle cell or fibroblast, can be determined. This is achieved by assaying the compound in a range of different cells, and selecting those compounds that selectively modulate PKCε activity in hepatocytes and/or pancreatic β-islet cells.

For example, the present invention also provides a method for determining a compound that specifically antagonizes a protein kinase C epsilon (PKCε) in a hepatocyte comprising:
(i) incubating a hepatocyte and an insulin-responsive cell other than a hepatocyte in the presence and absence of a candidate compound;
(ii) stimulating the hepatocyte and the other insulin-responsive cell at (i) with insulin; and
(iii) determining the rate of internalization of the insulin receptor in the insulin-stimulated hepatocytes and the other insulin-responsive cell line wherein reduced insulin receptor internalization in the presence of the candidate compound compared to in the absence of the candidate compound in the insulin-stimulated hepatocyte but not in the other insulin-responsive cell indicates that the compound specifically antagonizes a PKCε in a hepatocyte.

Preferably, the hepatocyte is a human hepatoma cell line such as, for example, Huh7, or a primary hepatocyte such as, for example, a primary murine, rat or human hepatocyte.

Preferably, the other insulin-responsive cell is a muscle cell (e.g., $C_2C_{12}$ or $L_6$ myoblast or human, rat or murine skeletal muscle cell or cardiac muscle cell), an islet cell (e.g., MIN6 or isolated human, rat or murine pancreatic islet cell), or an adipocyte (e.g., 3T3-L1 adipocyte). Other cells are not to be excluded. Cells mat have been transfected to express an insulin receptor, to make them insulin-responsive can also be used.

In an alternative embodiment, the present invention provides a method of determining a compound that specifically antagonizes a protein kinase C epsilon (PKCε) in a pancreatic β-islet cell comprising:
(i) incubating a pancreatic β-islet cell and an insulin-responsive cell other than a pancreatic β-islet cell with an amount of a lipid or free fatty acid (FFA) and/or glucose;
(ii) incubating the cells at (i) in the presence and absence of a candidate compound; and
(iii) determining the level of glucose-stimulated insulin secretion by the cells wherein enhanced insulin secretion in the presence of the candidate compound compared to in the absence of the compound in the pancreatic β-islet cell but not in the other insulin-responsive cell indicates that the compound that the compound specifically antagonizes a PKCε in a pancreatic β-islet cell.

Preferably the lipid or FFA is selected from the group consisting of palmitic acid, oleic acid, linoleic acid, myristic acid, lauric acid, pentadecanoic acid, stearic acid, and linolenic acid.

Preferably, the islet cell is a cultured murine MIN6 cell or an isolated human, rat or murine pancreatic islet cell. Preferably, the other insulin-responsive cell is a hepatocyte (e.g., a human hepatoma cell line such as, for example, Huh7, or a primary hepatocyte such as, for example, a primary murine, rat or human hepatocyte), a muscle cell (e.g., $C_2C_{12}$ or $L_6$ myoblast or human, rat or murine skeletal muscle cell or cardiac muscle cell), or an adipocyte (e.g., 3T3-L1 adipocyte). Other cells are not to be excluded.

For example, MIN6 cells overexpressing a PKCε protein in the presence or absence of free fatty acid (e.g., oleate or palmitate), are assayed for PKCε activity in the presence of siRNA against PKCε. A growth hormone reporter gene is also employed to allow the effects of overexpression and inhibition or expression to be determined without the confounding issue of transfection efficiency. The PKCε phenotype of the cell is established in vitro. The specificity of the siRNA is determined by analyzing gene expression, or by expressing various other PKCε substitution or deletion mutants in the siRNA-treated MIN6 cells and determining whether or not activity is restored. For such gain of function assays, the wild type, kinase-inactivated and constitutively active mutants of PKCε are useful, as is a short peptide corresponding to the V1-2 region which inhibits translocation of PKCε.

To confirm the ability of an antagonist compound to inhibit PKCε by binding directly to the enzyme, an immunoassay can be performed. Cells expressing recombinant PKCε in vitro can be contacted with the compound, which may be labelled such as using a radioligand or chromophore, under conditions permitting binding of the compound to the PKCε polypeptide and the binding is detected. For example, the compound bound to a recombinant PKCε, preferably expressed as a fusion protein with a detectable tag, is purified from Sf9 cell lysates expressing recombinant PKCε by virtue of the ligand attached to the compound, and the identity of PKCε confirmed by any method known to the skilled artisan. For example, tryptic digestion and microcapillary liquid chromatography electrospray ionisation tandem mass spectrometry (μLC/ESI-MS/MS) can be employed to identify a fragment of PKCε by virtue of its amino acid sequence. Alternatively, an immunoassay such as a radioimmunoassay or ELISA can be employed, using antibodies against PKCε. Alternatively, or in addition, labelled compounds can be detected bound to PKCε by co-immunoprecipitation of compound-PKCε complexes from cell lysates and subsequently identifying the PKCε protein in the labelled fraction by silver-staining and/or trypsin digestion and/or μLC/ESI-MS/MS, or immunoblotting. Co-localization of PKCε with antagonist compounds is also investigated in intact cells.

Antagonists of PKCε and Methods for their Delivery to Cells

In the present context, the term "antagonist" shall be taken to mean a small molecule, nucleic acid, protein, polypeptide, peptide, or antibody capable of inhibiting PKCε selectively or non-selectively, by inhibiting the activity of PKCε and/or by reducing transcription or translation of PKCε-encoding nucleic acid in a cell and preferably in a hepatocyte and/or pancreatic β-islet cell or a cell line derived therefrom. An inhibitor of enzyme activity may be a competitive or non-competitive inhibitor with respect to a known substrate of the PKCε enzyme, or an inhibitor of the translocation of the PKCε, or an inhibitor of the kinase activity of the PKCε such as, for example, by competing with the endogenous PKCε for the ATP substrate.

In one embodiment, the antagonist is a specific antagonist of protein kinase C epsilon (PKCε).

Alternatively, or in addition, the antagonist is a compound that exerts its effect on a protein kinase C epsilon (PKCε) in a tissue other than adipose or skeletal muscle or cardiac muscle, such as, for example, in the liver or pancreas. In accordance with this embodiment, the effect of the antagonist on a protein kinase C epsilon (PKCε) in a tissue other than adipose or skeletal muscle or cardiac muscle may be a consequence of tissue-specificity of the compound per se or alternatively, a consequence of tissue-specific targeting of the compound to a particular tissue or cell of the animal or human subject. Accordingly, the antagonist may not modulate the uptake of glucose by skeletal muscle and/or may not modulate insulin sensitivity of skeletal muscle.

Preferred antagonist compounds modify insulin clearance by the liver and/or insulin secretion by the pancreas in addition to modulating glucose uptake and/or insulin sensitivity of skeletal muscle.

Although any molecule that inhibits PKCε is sufficient to reduce or ameliorate an abnormality in glucose metabolism, molecules that selectively inhibit PKCε are preferred because, as shown by PKCε null mutant mice, elimination of PKCε does not cause major developmental abnormalities or serious side effects. Since molecules that are capable of generally inhibiting PKC isozymes interfere with the various functions performed by those isozymes, such non-selective inhibitors, whilst effective, are likely to have unwanted side effects.

In a preferred embodiment, the antagonist is a polypeptide antagonist or oligonucleotide antagonist of PKCε, such as for example, a peptide comprising a sequence selected from the group consisting of SEQ ID Nos: 6-12, or a dominant negative mutant of PKCε comprising the amino acid sequence of SEQ ID NO: 15 or an oligonucleotide antagonist selected from the group consisting of SEQ ID Nos: 16-27.

For example, U.S. Pat. No. 5,783,405 describes a large number of antagonist peptides that inhibit PKC isozymes. Of these, one or more peptides or polypeptide comprising the amino acid sequence of a peptide selected from the group consisting of epsilon V1-1 (NGLLKIK; SEQ ID NO: 6), epsilon V1-2 (EAVSLKPT; SEQ ID NO: 7), epsilon V1-3 (LAVFHDAPIGY; SEQ ID NO: 8), epsilon V1-4 (DDFVANCTI; SEQ ID NO: 9), epsilon V1-5 (WIDLEPEGRV; SEQ ID NO: 10) and epsilon V1-6 (HAVGPRPQTF; SEQ ID NO: 11) is particularly preferred as selective antagonists of PKCε. A peptide comprising the amino acid sequence set forth in SEQ ID NO: 7 is particularly preferred Another inhibitory peptide that the inventors have employed is that corresponding to pseudo substrate region (149-164) of PKCε comprising the amino acid sequence ERMRPRKRQGAVRRRV (SEQ ID NO: 12).

Preferably, a peptide antagonist is myristolylated at the N-terminus to facilitate cell entry. Alternatively, or in addition, the peptide is conjugated to a targeting moiety such as, for example Drosophila penetratin heptapeptide comprising the amino acid sequence RRMKWKK (SEQ ID NO: 13) to form a bioactive derivative.

A preferred polypeptide antagonist is a dominant negative mutant of PKCε, such as, for example, a protein that comprises one or more mutations in one or more domains of the full-length protein thereby producing a catalytically-inactive PKCε polypeptide that competitively inhibits the action of the native or endogenous PKCε enzyme in a cell. A "kinase-dead" PKCε polypeptide which comprises an amino acid sequence of a native PKCε polypeptide wherein the ATP-binding site is inactivated is particularly preferred. As exemplified herein, the amino acid sequence of a "kinase-dead" PKCε polypeptide comprising a substitution of lysine for arginine at position 437 of the human or murine PKCε polypeptide set forth in SEQ ID Nos: 2 or 4 (the "K437R mutant") is set forth in SEQ ID NO: 14 or 15, respectively. The K437R mutant competes with wild-type PKCε for ATP, thereby competitively inhibiting the activity of the endogenous PKCε polypeptide in a cell.

In a particularly preferred embodiment, the antagonist is targeted to the liver or pancreas of the subject.

In one embodiment, liver or pancreas delivery is achieved using a suitable vector. Accordingly, the present invention also provides a vector capable of expressing a polypeptide antagonist (e.g., dominant negative mutant or peptide inhibitor) or oligonucleotide antagonist (e.g., antisense, ribozyme, siRNA or RNAi) of a protein kinase C epsilon (PKCε) in a format suitable for introduction into a hepatocyte or pancreatic β-islet cell and expression therein.

For liver-specific delivery of polypeptide inhibitors, expression vectors designed to interact with specific receptors on liver cell surfaces that mediate receptor-mediated endocytosis can be used. Adenovirus vectors have been shown to efficiently deliver to cultured hepatocytes and to mouse liver cells in vivo (Herz and Gerard, Proc. Natl. Acad. Sci. USA 90, 2812-2816, 1993; Engelhardt et al., Proc. Natl. Acad. Sci. USA 91, 6196-6200, 1994; Raper et al. Hum. Gene Ther. 9, 671-679, 1998).

Preferably, a replication-defective hepadnavirus (hepatotropic DNA virus) vector is used for liver-specific delivery (see, for example, Ganem, D. Fields, B. N., Knipe, D. M., & Howley, P. M., eds. (1996) in *Fields Virology* (Lippincott, Philadelphia). Complementation in trans by a helper virus genome carrying a deletion in the viral packaging signal ε is used in combination with the hepadnavirus (hepatotropic DNA virus) vector. This is a key cis-acting element required for incorporation of the genomic viral RNA into virus particles (Junker-Niepmann et al., EMBO J. 9, 3389-3396, 1990), where it can be reverse-transcribed. The helper, therefore, provides all of the essential replication functions, but cannot itself be propagated as an infectious virus. Co-transfection of the chimeric genome and helper genome into a permissive cultured hepatoma cell results in the release of encapsidated chimeric progeny. These progeny then can be used to infect either primary hepatocytes in vitro or animal hosts in vivo. In a particularly preferred embodiment, the hepadnavirus vector is a replication-deficient human hepatitis B virus (HBV).

Other suitable viral delivery vectors, such as, for example, adeno-associated virus, can also be employed in this context.

For liver-specific expression of the peptides, nucleic acid encoding the peptides is placed operably under the control of a promoter such as, for example, the human phenylalanine hydroxylase gene promoter (Chatterjee et al. Proc. Natl. Acad. Sci. USA 93, 728-733, 1996), transthyretin promoter (Aurisicchio et al., J. Virol., 74, 4816-4823, 2000), serum albumin gene promoter, cytochrome P450 2B gene promoter, apolipoprotein A-1 gene promoter, phosphoenolpyruvate carboxykinase gene promoter, ornithine transcarbamylase gene promoter, UDP-glucuronosyltransferase gene promoter or hepatocyte nuclear factor 4 gene promoter.

For expression in pancreatic β-islet cells, the use of a promoter from a gene encoding insulin (Kulkarni et al., Cell 96, 329-339, 1999) or is preferred. Alternatively, the pdx-1 promoter/enhancer (Gannon et al., Genesis 26, 143-144, 2000) can be used.

By "promoter" in the present context is meant sufficient nucleic acid from a genomic gene fragment to confer expression at least in a β-islet cell and/or a hepatocyte and preferably at an enhanced level in the islet cell and/or hepatocyte. Even more preferably, expression is substantially in the islet cell and/or hepatocyte compared to other cells in the body of the subject.

Placing a nucleic acid molecule encoding the polypeptide antagonist under the regulatory control of, i.e., "in operable connection with", a promoter sequence means positioning said molecule such that expression is controlled by the promoter sequence, generally by positioning the promoter 5' (upstream) of the peptide-encoding sequence.

Means for introducing the nucleic acid or a gene construct comprising same into a cell for expression are well-known to those skilled in the art. The technique used for a given organism depends on the known successful techniques. Means for introducing recombinant DNA into animal cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

Preferred cell lines for testing the expression and/or efficacy of such polypeptide antagonists in hepatocytes include the human hepatoma cell line Huh7, or primary mouse or rat hepatocytes.

For delivery to pancreatic β-islet cells, it is particularly preferred to transfect a cultured pancreatic cultured cell line or embryonic stem cell line capable of differentiating into a pancreatic islet cell with the recombinant gene construct expressing the polypeptide antagonist and then transplant the transfected cell into the kidney capsule or pancreas of a subject in need of treatment.

Small molecule inhibitors of PKC are described in U.S. Pat. Nos. 5,141,957, 5,204,370, 5,216,014, 5,270,310, 5,292,737, 5,344,841, 5,360,818, and 5,432,198. These molecules belong to the following classes: N,N-Bis-(sulfonamido)-2-amino-4-iminonaphthalen-1-ones; N,N-Bis-(amido)-2-amino-4-iminonaphthalen-1-ones; vicinal-substituted carbocyclics; 1,3-dioxane derivatives; 1,4-Bis-(aminohydroxyalkylamino)-anthraquinones; furocoumarinsulfonamides; Bis-(hydroxyalkylamino)-anthraquinones; and N-aminoalkyl amides. A β-adrenergic agonist compound may also be used. Due to their relative ease of administration eg., by transdermal delivery or ingestion, small molecule inhibitors of PKCε are also preferred.

U.S. Pat. No. 6,339,066 incorporated herein by reference describes several antisense oligonucleotides that specifically inhibit the transcription and/or translation of mRNA encoding PKCε. Such oligonucleotides are complementary to, and specifically hybridizable with, nucleic acid encoding PKCε thereby modulating expression of a PKCε-encoding gene. By "nucleic acid encoding PKCε" is meant nucleic acid comprising a nucleotide sequence that is at least about 80% identical to at least about 20 contiguous nucleotides of the sequence of the murine or human PKCε mRNA set forth in SEQ ID NO: 1 or 3 or a genomic gene equivalent thereof. Preferably, the percentage identity of an antisense oligonucleotide to SEQ ID NO: 1 or 3 or to a genomic gene equivalent thereof is at least about 85%, more preferably at least about 90%, even more preferably at least about 95% and still more preferably at least about 99%. Preferred antisense oligonucleotides comprise at least about 50 contiguous nucleotides or at least about 100 or 500 contiguous nucleotides complementary to the target mRNA sequence, and preferably complementary to the 5'-untranslated region and/or 3'-untranslated region and/or coding region, or alternatively, to the entire target mRNA sequence. Such oligonucleotides may be conveniently and desirably presented in a pharmaceutically acceptable carrier to an animal in need of modulation of PKCε expression and/or activity.

Preferred antisense oligonucleotides comprise substantially chirally pure phosphorothioate intersugar linkages. The term "substantially chirally pure" is intended to indicate that the intersugar linkages of the oligonucleotides of the invention are either substantially all Sp, or substantially all Rp, phosphorothioate intersugar linkages. For example, such oligonucleotides have an increased thermodynamic stability, compared to phosphodiester oligonucleotides of identical sequence, in heteroduplexes formed with the target RNA.

In a particularly preferred embodiment, an antisense oligonucleotide against PKCε will comprise a nucleotide sequence selected from the group consisting of:

| | | |
|---|---|---|
| (i) | CATGAGGGCCGATGTGACCT; | (SEQ ID NO: 16) |
| (ii) | TGCCACACAGCCCAGGCGCA; | (SEQ ID NO: 17) |
| (iii) | AAGGAAAGTCTGCGGCCGGG; | (SEQ ID NO: 18) |
| (iv) | TGGCGGCTCCCGTTCTGCAG; | (SEQ ID NO: 19) |
| (v) | GCTTCCTCGGCCGCATGCGT; | (SEQ ID NO: 20) |
| (vi) | TTGACGCTGAACCGCTGGGA; | (SEQ ID NO: 21) |
| (vii) | GCCCGGTGCTCCTCTCCTCG; | (SEQ ID NO: 22) |
| (viii) | GGGCCGATGTGACCTCTGCA; | (SEQ ID NO: 23) |
| (ix) | TGGAGGAACATGAGGGCCGA; | (SEQ ID NO: 24) |
| (x) | CCCCCAGGGCCCACCAGTCC; | (SEQ ID NO: 25) |
| (xi) and | TGCGATGCCACACAGCCCAG; | (SEQ ID NO: 26) |
| (xii) | TGGGCTCTCAGGGCATCAGG. | (SEQ ID NO: 27) |

Nucleic acid antagonists may also comprise ribozymes or small interfering RNA (siRNA).

As used herein, a "ribozyme" is a nucleic acid molecule having nuclease activity for a specific nucleic acid sequence. A ribozyme specific for PKCε-encoding mRNA, for example, binds to and cleaves specific regions of the mRNA, thereby rendering it untranslatable. To achieve specificity, preferred ribozymes will comprise a nucleotide sequence that is complementary to at least about 12-15 contiguous nucleotides of a sequence encoding the amino acid sequence set forth in SEQ ID NO; 1 or 3.

As used herein, the terms "small interfering RNA", and "RNAi" refer to homologous double stranded RNA (dsRNA) that specifically targets a gene product, thereby resulting in a null or hypomorphic phenotype. Specifically, the dsRNA comprises two short nucleotide sequences derived from the target RNA encoding PKCε and having self-complementarity such that they can anneal, and interfere with expression of a target gene, presumably at the post-transcriptional level. RNAi molecules are described by Fire et al., Nature 391, 806-811, 1998, and reviewed by Sharp, Genes & Development, 13, 139-141, 1999).

DNA-containing complexes designed to interact with specific receptors on liver cell surfaces that mediate receptor-mediated endocytosis can be used to target nucleic acid antagonists (e.g., antisense, ribozyme, siRNA, RNAi) to the liver (reviewed by Smith and Wu Semin. Liver Dis., 19, 83-92, 1999). Adenovirus vectors have been shown to efficiently deliver genes to cultured hepatocytes and to mouse liver cells in vivo (Herz and Gerard, Proc. Natl. Acad. Sci. USA 90, 2812-2816, 1993; Engelhardt et al., Proc. Natl, Acad. Sci. USA 91, 6196-6200, 1994; Raper et al., Hum: Gene Ther. 9, 671-679, 1998).

Preferably, a replication-defective hepadnavirus (hepatotropic DNA virus) vector is used for liver-specific gene transfer to deliver the oligonucleotide antagonist (see, for example, Ganem, D. Fields, B. N., Knipe, D. M., & Howley, P. M., eds. (1996) in *Fields Virology* (Lippincott, Philadelphia). Complementation in trans by a helper virus genome carrying a deletion in the viral packaging signal ε is used in combination with the hepadnavirus (hepatotropic DNA virus) vector. This is a key cis-acting element required for incorporation of the genomic viral RNA into virus particles (Junker-Niepmann et al., EMBO J. 9, 3389-3396, 1990), where it can be reverse-transcribed. The helper, therefore, provides all of the essential replication functions, but cannot itself be propagated as an infectious virus. Co-transfection of the chimeric genome and helper genome into a permissive cultured hepatoma cell results in the release of encapsidated chimeric progeny. These progeny then can be used to infect either primary hepatocytes in vitro or animal hosts in vivo. In a particularly preferred embodiment, the hepadnavirus vector is a replication-deficient human hepatitis B virus (HBV).

Other appropriate viral vectors, such as, for example, an adeno-associated vector, can also be employed.

Alternatively, oligonucleotide antagonists are expressed under the control of a liver-specific promoter such as, for example, the human phenylalanine hydroxylase gene promoter (Chatterjee et al., Proc. Natl. Acad. Sci. USA 93, 728-733, 1996), transthyretin promoter (Aurisicchio et al., J. Virol., 74, 4816-4823, 2000), serum albumin gene promoter, cytochrome P450 2B gene promoter, apolipoprotein A-1 gene promoter, phosphoenolpyruvate carboxykinase gene promoter, ornithine transcarbamylase gene promoter, UDP-glucuronosyltransferase gene promoter or hepatocyte nuclear factor 4 gene promoter. Means for placing an oligonucleotide antagonist operably under the control of a liver-specific promoter, and introducing the expression construct into a hepatocyte are described herein above for expression constructs encoding polypeptide antagonists.

For expression in pancreatic β-islet cells, the use of a promoter from a gene encoding insulin (Kulkarni et al., Cell 96, 329-339, 1999) or is preferred. Alternatively, the pdx-1 promoter/enhancer (Gannon et al., Genesis 26, 143-144, 2000) can be used.

For delivery to pancreatic β-islet cells, it is particularly preferred to transfect a cultured pancreatic cultured cell line or embryonic stem cell line capable of differentiating into a pancreatic islet cell with the recombinant gene construct expressing the oligonucleotide antagonist and then transplant the transfected cell into the kidney capsule or pancreas of a subject in need of treatment.

The present invention clearly extends to any isolated hepatocyte or pancreatic β-islet cell comprising introduced nucleic acid encoding a polypeptide antagonist or oligonucleotide antagonist of PKCε.

Administration of PKCε Antagonists

The present invention provides for the use of an antagonist of a protein kinase C epsilon (PKCε) in the preparation of a medicament for the treatment of aberrant glucose metabolism in an animal or human subject.

The present invention also provides for the use of a vector capable of expressing a polypeptide antagonist or oligonucleotide antagonist of a protein kinase C epsilon (PKCε) in a format suitable for introduction into a hepatocyte or pancreatic β-islet cell and expression therein in medicine, and preferably in the preparation of a medicament for the treatment of aberrant glucose metabolism in an animal or human subject.

The present invention also clearly extends to the use of an isolated hepatocyte or pancreatic β-islet cell comprising introduced nucleic acid encoding a polypeptide antagonist or oligonucleotide antagonist of PKCε in medicine, and preferably in the preparation of a medicament for the treatment of aberrant glucose metabolism in an animal or human subject.

Because PKCε is an intracellular protein, preferred embodiments of the invention involve administering pharmaceutically acceptable antagonist formulations capable of permeating the plasma membrane. Small, a polar molecules are often membrane permeable. The membrane permeability of other molecules can be enhanced by a variety of methods known to those of skill in the art, including dissolving them in hypotonic solutions, coupling them to transport proteins, and packaging them in micelles.

PKCε antagonists are administered hourly, several times per day, daily or as often as the subject in need thereof, or the subject's physician sees fit. Preferably, the administration interval will be in the range of 8 to 24 hours. Treatment can continue over the course of several days, one month, several months, one year, several years or the duration of the patient's lifetime.

Inhibitor dosage will vary according to many parameters, including the nature of the inhibitor and the mode of administration. For the epsilon PKC-v1 peptide, a 150 μg/ml intracellular concentration inhibited PKCε translocation and downstream effects of PKCε activation (U.S. Pat. No. 5,783, 405). Daily dosages in the range of 1 μg/kg body weight to about 100 mg/kg of body weight, preferably 1 μg/kg to about 1 mg/kg and most preferably 10 μg/kg to about 1 mg/kg are contemplated for PKCε antagonists that are N,N-Bis-(sulfonamido)-2-amino-4-iminonaphthalen-1-ones or N,N-Bis-(amido)-2-amino-4-iminonaphthalen-1-ones or vicinal-substituted carbocyclics. Daily dosages in the range of 5-400 mg/kg of body weight, preferably 10-200 mg/kg and most preferably 10-50 mg/kg are contemplated for PKCε antagonists that are 1,4-Bis-(amino-hydroxyalkylamino)-anthraquinones, Bis-(hydroxyalkylamino-anthraquinones, or N-aminoalkyl amides. Daily dosages in the range of 0.1-40 mg/kg of body weight, preferably 1-20 mg/kg, are contemplated for PKC inhibitors that are 1,3-dioxane derivatives. Daily dosages in the range of 1-100 mg/kg of body weight are contemplated for PKC inhibitors that are furo-coumarinsulfonamides.

The methods of this invention are useful for treating mammals in general and humans in particular.

A preferred embodiment of the present invention is the administration of a pharmaceutically acceptable formulation of an inhibitor of PKCε. A "pharmaceutically acceptable formulation" comprises one that is suitable for administering the PKCε antagonist in a manner that gives the desired results and does not also produce adverse side effects sufficient to convince a physician that the potential harm to a patient is greater than the potential benefit to that patient. The basic ingredient for an injectable formulation is a water vehicle. The water used will be of a purity meeting USP standards for sterile water for injection. Aqueous vehicles that are useful include sodium chloride (NaCl) solution, Ringer's solution, NaCl/dextrose solution, and the like. Water-miscible vehicles are also useful to effect full solubility of the PKCε inhibitor. Antimicrobial agents, buffers and antioxidants are useful, depending on the need.

In preparing PKCε antagonist compositions for this invention, one can follow the standard recommendations of well known pharmaceutical sources such as Remington: The Science and Practice of Pharmacy, 19.sup.th ed., (Mack Publishing, 1995). In general, the pharmaceutical composition of this invention is powder- or aqueous-based with added excipients that aid in the solubility of the PKCε antagonist, the isotonicity of the composition, the chemical stability and the deterrence of microorganism growth. For oral administration, it is preferable to include substances that protect the PKCε antagonist from degradation by digestive agents.

The present invention additionally provides a genetically modified non-human mammal that lacks a functional endogenous PKC-ε gene and comprises a heterologous PKC-ε gene or a fragment thereof. For example, the non-human mammal comprises and expresses a human PKC-ε gene. Such a mammal is referred to as a "non-human PKC-ε knock-in mammal" or a "PKC-ε knock-in mammal". Accordingly, the invention provides a source of a cell, a tissue, a cellular extract, an organelle or a mammal that comprises or expresses human PKC-ε, preferably at normal levels.

As used herein, the term "normal levels" shall be taken to mean that the heterologous PKC-ε is expressed at a level substantially similar to the level of expression of the endogenous PKC-ε in the non-human mammal. Furthermore, gene expression occurs in the same or similar cells and/or tissues as the endogenous PKC-ε gene. Methods for determining the level of expression of a gene product and/or the site of gene expression are known in the art and described, for example, in Ausubel et al (In: Current Protocols in Molecular Biology. Wiley Interscience, ISBN 047 150338, 1987) and (Sambrook et al (In: Molecular Cloning: Molecular Cloning: A Laboratory Manual, Cold Spring Harbor Laboratories, New York, Third Edition 2001).

Such mammals are useful for screening to determine a compound that inhibits human PKC-ε. Alternatively, or in addition this embodiment of the invention provides a source of a cell, a tissue, a cellular extract, an organelle or a mammal useful for determining a compound that inhibits human PKC-ε.

Any suitable mammal can be used to produce the PKC-ε knock-in mammal described herein. For example, a suitable mammal can be, a mouse, a rat, a rabbit, a pig, a sheep or a cow. Preferably, a mouse is used to produce a PKC-ε knock-in mammal.

As will be apparent to the skilled artisan, to produce a knock-in mammal it is not necessary to replace the entire endogenous PKC-ε gene. For example, only the region of the endogenous PKC-ε gene that encodes a protein is replaced. Clearly, this encompasses replacement of exons that encode a PKC-ε protein and intervening intronic regions. By retaining one or more regions of the endogenous PKC-ε gene, e.g., a promoter region, the expression of the heterologous PKC-ε gene is retained at normal levels.

In one embodiment, the invention provides a knock-in mammal whose genome comprises either a homozygous or heterozygous replacement of the endogenous PKC-ε gene or a region thereof. A knock-in mammal whose genome comprises a homozygous replacement is characterized by somatic and germ cells which contain two copies of the heterologous PKC-ε gene or region thereof while a knock-in mutant whose genome comprises a heterozygous replacement is characterized by somatic and germ cells which contain one endogenous allele and one heterologous allele of the PKC-ε gene.

As used herein, the term "genotype" refers to the genetic makeup of a mammal with respect to the PKC-ε chromosomal locus. More specifically the term genotype refers to the status of the mammal's PKC-ε alleles, which can either be intact (e.g., endogenous or +/+); or replaced in a manner that confers either a heterozygous (e.g., +/h); or homozygous (h/h) knock-in genotype (wherein the symbol "h" refers to a heterologous PKC-ε gene or region thereof).

The present invention also provides a method for producing a non-human PKC-ε knock-in mammal. Methods for producing a "knock-in mammal" are known in the art and described, for example, in Nagy et al eds. *Manipulating the Mouse Embryo*, Cold Spring Harbor Laboratory, 3rd Edition, 2002, ISBN 0879695749 and Tymms and Kola eds *Gene Knockout Protocols*, Humana Press, 2001, ISBN: 0896035727.

In one embodiment, the PKC-ε knock-in mammal is produced using homologous recombination to replace the endogenous PKC-ε gene or region thereof (e.g., a coding region) with a heterologous PKC-ε gene or region thereof. For example, a mouse is produced in which the endogenous PKC-ε gene is replaced with a human PKC-ε gene.

To produce a mutant mouse strain by homologous recombination, two elements are generally used. An embryonic stem (ES) cell line capable of contributing to the germ line of the mammal of interest, and a targeting construct containing target-gene sequences, e.g., a heterologous PKC-ε gene or region thereof. ES cell lines are derived from the inner cell mass of a blastocyst-stage embryo. The targeting construct is transfected into cultured ES cells. Homologous recombination occurs in a number of the transfected cells, resulting in introduction of the PKC-ε gene or region thereof present in the targeting construct into the target gene. Once identified, mutant ES cell clones are microinjected into a normal blastocyst and the blastocyst introduced into a female (e.g., a pseudopregnant female) to produce a chimeric mammal, e.g. a chimeric mouse. As ES cell lines retain the ability has cells and/or tissues, including the germ line cells, with contribution from both the normal blastocyst and the mutant ES cells. Breeding germ-line chimeras yields mammals that are heterozygous for the mutation introduced into the ES cell, and that can be interbred to produce homozygous mutant mice.

Production of a Knock-In (Gene-Targeting) Construct

A replacement construct is generally used to produce a knock-in mammal. Such a replacement construct usually contains two regions of homology to the target gene located on either side of a heterologous nucleic acid (for example, encoding a heterologous PKC-ε protein or region thereof and, optionally, one or more reporter genes for selection of a cell carrying the construct (e.g. enhanced green fluorescent protein), β-galactosidase, an antibiotic resistance protein (e.g. neomycin resistance or zeocin resistance) or a fusion protein (e.g. the; β-galactosidase-neomycin resistance protein, β-geo). Homologous recombination proceeds by a double cross-over event that replaces the target-gene sequences with the replacement-construct sequences (i.e. a region of the gene that occurs between the regions of homology with regions of the targeting construct are replaced with the heterologous nucleic acid).

Should a reporter gene be used it is preferably flanked by recombination sites to thereby facilitate its removal from the genomic DNA of a cell or mammal. For example, the reporter gene is flanked by LoxP sites (which are recognition sites of the P1 recombination enzyme Cre) or fit sites (which are recognition sites of the yeast recombinase flp). Methods for using such recombinase sites for the production of a targeting vector and of the production of a knock-in mammal are known in the art and described, for example, in Fiering et al., Genes Dev.; 9:2203-2213, 1995; Vooijs et al., Oncogene. 17, 1-12 1998.

For example, If there are two loxP sites in the same orientation near each other in a nucleic acid, Cre removes the sequence between the two sites, leaving a single loxP site in the original DNA and a second loxP in a circular piece of DNA containing the intervening sequence. Accordingly, loxP sites or fit sites that are inserted flanking a reporter gene are useful for the removal of the intervening sequence.

The present invention provides a vector construct (e.g., a PKC-ε targeting vector or PKCε targeting construct) designed to replace an endogenous mammalian PKC-ε gene with a heterologous PKC-ε gene. In general terms, an effective PKC-ε targeting vector comprises a nucleic acid comprising a nucleotide sequence that is effective for homologous recombination with the endogenous PKC-ε gene. For example, a replacement targeting vector comprises a nucleic acid encoding a heterologous PKC-ε gene or region thereof and optionally a selectable marker gene flanked by regions of nucleic acid homologous to or substantially identical to a genomic sequence of the endogenous PKC-ε gene or a region thereof. For example, the nucleic acid encoding a heterologous PKC-ε gene or region thereof and optionally a selectable marker gene is flanked by a region homologous to or substantially identical to a region of the endogenous PKC-ε genomic DNA 5' to the first coding exon of the endogenous PKC-ε gene and another region homologous to or substantially identical to a region of the endogenous PKC-ε genomic DNA 3' to the last coding exon of the endogenous PKC-ε gene.

Alternatively, the entire endogenous PKC-ε genomic gene is replaced with a heterologous PKC-ε genomic gene. For example, the promoter region, 5' untranslated region, exons, introns and 3' untranslated regions of the endogenous PKC-ε genomic gene is replaced with the same regions of the heterologous PKC-ε gene. Alternatively, the endogenous PKC-ε gene is replaced with a region of the heterologous PKC-ε gene or a minigene (e.g., a cDNA operably under control of a promoter) encoding a heterologous PKC-ε.

One of skill in the art will recognize that any PKC-ε genomic nucleic acid of appropriate length and composition to facilitate homologous recombination at a specific site that has been preselected for disruption can be employed to construct a PKC-ε targeting vector. Guidelines for the selection and use of sequences are described for example in Deng and Cappecchi, Mol. Cell. Biol, 12:3365-3371, 1992 and Bollag, et al., Annu. Rev. Genet., 23:199-225, 1989.

Suitable targeting constructs of the invention are prepared using standard molecular biology techniques known to those of skill in the art. For example, techniques useful for the preparation of suitable vectors are described by Maniatis, et al., Molecular Cloning: A Laboratory Manual, Cold Spring Harbor Laboratory, Cold Spring Harbor, N.Y.

One of skill in the art will readily recognize that any of a number of appropriate vectors known in the art can be used as the basis of a suitable targeting vector. In practice, any vector that is capable of accommodating the recombinant nucleic acid required for homologous recombination and the heterologous PKC-ε gene or region thereof is suitable. For example, pBR322, pACY164, pKK223-3, pUC8, pKG, pUC19, pLG339, pR290, pKC101 or other plasmid vectors are useful. Alternatively, a viral vector such as the lambda gt11 vector system is useful in the production of a targeting construct. As a further alternative a bacterial artificial chromosome (BAC) or a yeast artificial chromosome (YAC) is used as a targeting vector, for example, for replacing an entire endogenous PKC-ε gene.

Production of a PKC-ε Knock-In Cell

Following production of a suitable gene construct comprising nucleic acid encoding a functional PKCε protein e.g., human PKCε, the construct is introduced into a relevant cell. Methods for introducing the gene construct into a cell are known to those skilled in the art and are described for example, in Ausubel et al (In: Current Protocols in Molecular Biology. Wiley Interscience, ISBN 047 150338, 1987) and (Sambrook et al (In: Molecular Cloning: Molecular Cloning: A Laboratory Manual, Cold Spring Harbor Laboratories, New York, Third Edition 2001). Means for introducing recombinant DNA into a cell include, but are not limited to electroporation, microinjection, transfection mediated by DEAE-dextran, transfection mediated by calcium phosphate, transfection mediated by liposomes such as by using Lipofectamine (Invitrogen) and/or cellfectin (Invitrogen), transduction by Adenoviruses, Herpesviruses, Togaviruses or Retroviruses and microparticle bombardment such as by using DNA-coated tungsten or gold particles (Agacetus Inc., WI, USA). For example, a cell is electroporated with a targeting construct of the invention.

A suitable cell for the production of a knock-in mammal is, for example, an embryonic stem cell. Those of skill in the art will recognize that various stem cells and stem cell lines are known in the art, such as, for example, AB-1, HM-1, D3. CC1.2, E-14T62a, RW4 or JI (Teratomacarcinoma and Embryonic Stem Cells: A Practical Approach, E. J. Roberston, ed., IRL Press). Clearly, a suitable stem cell or stem cell line will depend upon the type of knock-in mammal to be produced. For example, should a knock-in mouse be desired a mouse ES cell line is used. Furthermore, should an inbred strain of knock-in mice be preferred, an ES cell line derived from the same strain of mouse that is to be used is preferred.

Following transfection cells are maintained under conditions sufficient for homologous recombination to occur while maintaining the pluripotency of the ES cell.

In an example of the invention, an ES cell is selected that has homologously recombined to introduce the targeting vector into it's genome (as opposed to random integration). A method used for eliminating cells in which the construct integrated into the genome randomly, thus further enriching for homologous recombinants, is known as positive-negative selection. Such methods are described, for example, in U.S. Pat. No. 5,464,764. Briefly, a construct useful for positive-negative selection comprise a negative selectable marker (e.g., herpes simplex virus thymidine kinase, HSV-TK) outside the region of homology to the target gene (i.e. in a region that will not be incorporated into the genome of a cell following homologous recombination). In the presence of the TK gene, the cells are sensitive to acyclovir and/or an analog thereof (e.g., gancyclovir, GANC). The HSV-TK enzyme activates these drugs, resulting in their incorporation into growing DNA, causing chain termination and cell death. During homologous recombination, sequences outside the regions of homology to the target gene are lost due to crossing over. In contrast, during random integration substantially all of the sequences in the construct are retained as recombination usually occurs at the ends of the construct. The presence of the TK gene is selected against by growing the cells in gancyclovir, the homologous recombinants are gancyclovir-resistant, whereas clones in which the construct integrated randomly are gancyclovir-sensitive. Other markers that are lethal to cells have also been used instead of TK and gancyclovir (e.g., diphtheria toxin; Yagi et al., *Proc Natl Acad Sci USA*. 57:9918-9922, 1990).

Alternatively, or in addition, a cell is screened using, for example, PCR or Southern blotting to determine a targeting construct that has integrated into the correct region of the genome rather than randomly integrated. Methods for such screening are known in the art, and described, for example, in Nagy et al eds. *Manipulating the Mouse Embryo*, Cold Spring Harbor Laboratory, 3rd Edition, 2002, ISBN 0879695749 and Tymms, Kola eds *Gene Knockout Protocols*, Humana Press, 2001, ISBN: 0896035727, Ausubel et al (In: Current Protocols in Molecular Biology. Wiley Interscience, ISBN 047 150338, 1987) and (Sambrook et al (In: Molecular Cloning: Molecular Cloning: A Laboratory Manual, Cold Spring Harbor Laboratories, New York, Third Edition 2001).

At this stage the reporter gene can be removed, if used, by expression or introduction of the relevant recombinase into the cell comprising the targeting vector. Alternatively, the reporter gene is removed by expressing the recombinase in a mouse carrying the targeting construct by production of a transgenic mouse or crossing the mouse with another mouse carrying a transgene expressing the recombinase.

Production of a PKC-ε Knock-In Mammal

Following production of an ES cell in which at least one copy of the PKC-ε gene has incorporated the targeting construct the cell is preferably grown to form an ES cell colony using methods known in the art. One or more cells from the colony are then used to produce a chimeric mammal.

An example of a method used to generate chimeras involves the injection of the genetically modified ES cells into the blastocoel cavity of a developing embryo. For example, should the targeted ES cell be of mouse origin, an ES cell is injected into the blastocoel cavity of a 3.5-day-old mouse embryo. The injected embryo is surgically implanted into the uterus of a foster mother, for example, a pseudopregnant female. A resultant offspring is a chimera as its tissues are produced from cells from both the host embryo and from the ES cell. Should the ES cell populate the germ line, the chimera can pass an altered gene to offspring, resulting in a new mouse strain in which all cells contain an altered gene.

By breeding a mouse of the new mouse strain with a wild-type mouse offspring that are heterozygous for the mutation are produced, i.e., PKC-ε$^{+/h}$. However, breeding two heterozygous mice, or two homozygous mice or a heterozygous mouse and a homozygous mouse produces at least one offspring that are homozygous for the mutation, i.e., PKCε$^{b/h}$ The present invention clearly contemplates both heterozygous and homozygous knock-in non-human mammals.

It is to be understood that a PKC-ε knock-in mammal described herein can be produced by methods other than the embryonic stem cell method described above, for example by the pronuclear injection of a gene construct into the pronucleus of a one-cell embryo or other gene targeting methods which do not rely on the use of a transfected ES cell, and that the exemplification of the single method outlined above is not intended to limit the scope of the invention to mammals produced solely by this protocol.

Production of a Transgenic PKC-ε Knockout Mammal

In another embodiment of the invention, a PKC-ε knockout mammal is produced and said mammal is additionally genetically modified to express a heterologous PKC-ε gene.

Methods for producing a knock-out mammal are known in the art and described, for example, in Nagy et al eds. *Manipulating the Mouse Embryo*, Cold Spring Harbor Laboratory, 3rd Edition, 2002, ISBN 0879695749 and Tymms and Kola eds *Gene Knockout Protocols*, Humana Press, 2001, ISBN: 0896035727.

For example, a replacement vector described supra is used, however, rather than replacing the endogenous PKC-ε gene with a heterologous PKC-ε gene it is replaced with, for example, a reporter gene. Preferably, the expression of the endogenous PKC-ε gene is partially or completely inhibited. Alternatively, or in addition, a region of the PKC-ε gene required for a biological activity of interest is removed or replaced thereby producing an inactive PKC-ε.

Methods for producing a PKC-ε knockout mouse are known in the art and described, for example, in Khasar et al., *Neuron* 24:253-260, 1999. Such a PKC-ε knockout mouse (B6.129S4-Prkce$^{tm1Msg}$/J) is also commercially available from Jackson Laboratories, Maine, USA.

Following producing or obtaining a PKC-ε knockout mammal a transgene expressing a heterologous PKC-ε is introduced into the knockout mammal. Such introduction is facilitated, for example, by crossing the knockout mammal with a mammal carrying a PKC-ε transgene or by producing a PKC-ε transgenic mammal using the knockout mammal.

Means of producing a transgenic mammal are known in the art and described, for example, in Hogan et al (In: Manipulating the Mouse Embryo. A Laboratory Manual, 2$^{nd}$ Edition. Cold Spring Harbour Laboratory. ISBN: 0879693843, 1994). For example, a gene construct comprising a human PKC-ε cDNA or genomic gene is produced using a method described herein and microinjected into the pronucleus of a fertilised mammalian oocyte. The oocyte is then microinjected into a uterus of a pseudopregnant recipient female mammal. Offspring that are screened for presence of the transgene in their genome using, for example, PCR screening or Southern hybridisation using methods known in the art. Those mice that comprise the transgene are bred, and their offspring assayed for transgene expression, using, for example, Northern blotting, RT-PCR and/or Western blotting. Such mice are then useful for the screening assay of the present invention.

Transgenic mammals are also produced by nuclear transfer technology as described in Schnieke, A. E. et al., 1997, Science, 278: 2130 and Cibelli, J. B. et al., 1998, Science, 280: 1256. Using this method, cells, e.g. fibroblasts, from donor mammals are stably transfected with a gene construct incorporating the coding sequences for a form of a PKC-ε polypeptide. Stable transfectants are then fused to enucleated oocytes, cultured and transferred into female recipients.

By using a tissue specific promoter, a mammal expressing a heterologous PKC-ε in a specific tissue or tissues or a particular cell type/s is produced.

By selecting or breeding for a mammal that is homozygous for the knockout of endogenous PKC-ε and heterozygous or heterozygous for the heterologous PKC-ε transgene a mouse expressing only the heterologous PKC-ε is obtained. The present invention clearly encompasses a mouse with a genotype selected from the group consisting of PKC-ε$^{-/-}$tg$^{+/-}$, PKC-ε$^{-/-}$tg$^{+/+}$, PKC-ε$^{+/-}$tg$^{+/-}$ and PKC-ε$^{+/-}$tg$^{+/+}$. In this context the symbol "tg" shall be taken to refer to a transgene; the symbol "−/−" shall be taken to refer to a knockout mammal; the symbol "+/−" shall be taken to refer to a mammal that comprises a heterozygous form of a gene; and the symbol "+/+" shall be taken to refer to a mammal that contains two copies of a gene, e.g., a transgene.

As will be apparent from the preceding discussion, the present invention contemplates a non-human mammal (e.g. a mouse) that has been genetically modified to express a heterologous PKC-ε (e.g., human PKC-ε) in place of endogenous PKC-ε.

The present invention additionally contemplates a cell, a cell line, a cell culture, a primary tissue, a cellular extract or a cell organelle isolated from a PKC-ε knock-in mammal of the present invention. For example, a cell culture, or cell line or cell is derived from any desired tissue or cell-type from a PKC-ε knock-in mouse. In one embodiment, a cell culture, or cell line or cell is derived a tissue or cell-type that express high levels of PKC-ε in nature.

In another embodiment, a PKC-ε knock-in mammal produced in accordance with the present invention is utilized as a source of cells for the establishment of cultures or cell lines (e.g., primary, immortalized) useful for determining a PKC-ε inhibitory compound.

In another embodiment, the present invention encompasses the use of a mouse expressing a heterologous PKC-ε, for example, a PKC-ε knock-in mouse or a cell or tissue derived therefrom in a screening method of the present invention.

The present invention is further described with reference to the following non-limiting examples.

Example 1

PKCε Null (PKCε$^{-/-}$) Mice

Figure 1A:
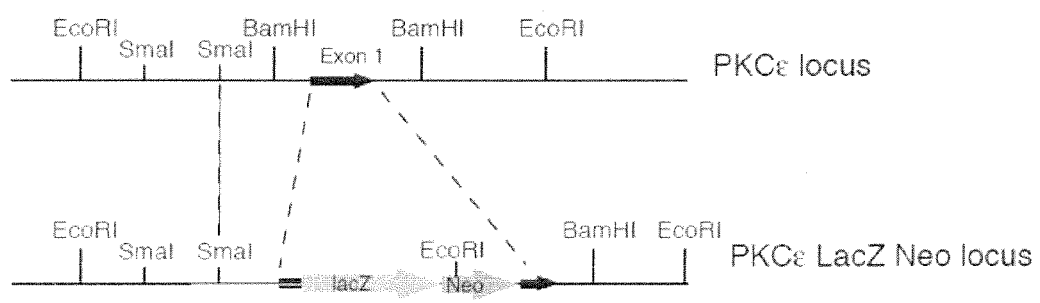
FIG. 1a is a schematic representation of the murine PKCε locus in wild type mice (top line) and PKCε null mice (lower line). The position of exon 1 of the PKCε gene is indicated by the arrow. In the PKCε null mouse, a targeting vector comprising a neomycin (Neo) gene operably under the control of a lacZ promoter (lacZ-Neo; light shaded arrows) flanked by PKCε exon 1 sequences (black arrows) has been inserted into the exon 1 sequences by homologous recombination. Restriction enzyme sites for the locus in both wild type and mutant genomes are as follows: B, BamHI; E, EcoRI; S, SmaI.

In order to address whether activation of PKCε was causally implicated in insulin resistance the inventors have made use of PKCε null mice developed by targeted disruption of the PKCε gene, by insertion of a neomycin and LacZ cassette in exon 1 of the mouse gene (FIG. 1a). As a consequence of the insertion, transcription is abolished and leads to a null allele.

Figure 1B:
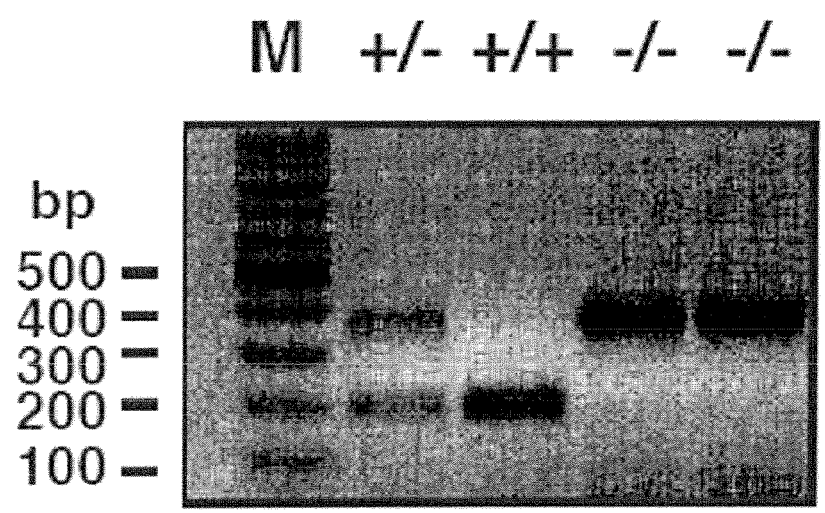
FIG. 1b is a copy of a photographic representation showing PCR amplification products of DNA derived from littermates of a PKCε$^{+/-}$ heterozygote intercross. M, marker DNA; +/-, PKCε$^{+/-}$ heterozygote; +/+, wild-type; -/-, PKCε$^{-/-}$ homozygous null.

For initial genotyping of adult mice with a background of 129/SVxOla, Southern blot analysis of EcoRI digested genomic DNA was performed. DNA was extracted from adult tail tissue and hybridised with an endogenous 5-probe distinguishing wild type, heterozygote mutant, and homozygote mutant alleles. The 5-probe corresponded to a 0.8-kb SmaI fragment hybridising to a 9 kb band in the wild type and a 6 kb band in the successfully mutated allele (not shown). Routine genotyping was carried out by PCR analysis of tail tip DNA, using a forward primer corresponding to a 5'-untranslated region of the PKCε locus and reverse primers corresponding to sequences in either exon 1 (wild type) or the Lac-Neo insert (mutant). The wild type allele gave rise to a 207 kb PCR product while the mutated allele gave rise to a 400 kb product (FIG. 1b).

Mice were maintained on a hybrid 129/SV C57BL/6 background, while experiments involving high-fat feeding were also performed on mice backcrossed at least 6 tunes on the C57BL/6 background, giving similar results. Ethical approval for mouse studies was granted by the Garvan Institute Animal Experimentation Ethics Committee, Sydney, Australia.

The PKCε null mouse is crossed into each of the following genetic backgrounds that produce suitable diabetic models in mice, thereby producing double mutants:
(i) yellow obese mouse (A$^{y/a}$), a dominant mutation causes the ectopic, ubiquitous expression of the agouti protein, resulting in a condition similar to adult-onset obesity and non-insulin-dependent diabetes mellitus (Michaud et al., Proc Natl Acad Sci USA 91: 2562-2566, 1994);
(ii) Obese (ob/ob) (Zhang et al., Nature 372: 425-432, 1994) which are leptin-deficient;
(iii) diabetes (db/db) (Tartaglia et al., Cell 83: 1263-1271, 1995) which are deficient in active leptin receptor;
(iv) adipose (cpe/cpe) (Naggert et al., Nat. Genet. 10: 135-142, 1995) which are deficient in carboxypeptidase E; and
(v) tubby (tub/tub) (Kleyn et al., Cell 85: 281-290, 1996; Noben-Trauth et al., Nature 380: 534-548, 1996).

Obese mice exhibit hyperglycemia, glucose intolerance, and elevated plasma insulin, which develops after the onset of obesity. In db/db mice, elevation of plasma insulin occurs at 2 weeks of age, preceding the onset of obesity at 3-4 weeks and elevation of blood glucose levels at 4-8 weeks. Adipose mice have hyperinsulinemia throughout life in association with hypertrophy and hyperplasia of the islets of Langerhans, with transient hyperglycemia. Tubby mice have normal blood glucose, however plasma insulin is elevated prior to obvious signs of obesity, and the islets of Langerhans are enlarged.

The glucose metabolism phenotype of each double mutant is determined to establish the effect(s) of the reduced PKCε expression on the diabetic model.

In addition to performing such crosses into a diabetic mouse background, pancreatic islets are isolated from the diabetic mouse models, maintained in culture for various periods in the presence or absence of one or more PKCε inhibitors, or kinase-dead constructs, siRNAs etc for a time and under conditions sufficient for the secretory defects of the islet cells, which are maintained for at least 1-2 days ex vivo, to be reversed.

Example 2

Conditional Knockout of PKCε Expression in the Liver

A conditional PKCε liver-null mouse on a Cre+ background is produced using a floxed PKCε allele, PKCε(fl/fl), and Cre recombinase under control of the albumin promoter (AlbCre) essentially as described by Matsusue et al., J Clin Invest. 111 (5), 737-747, 2003. The PKCε allele for producing the knockout was the same as that used previously. The liver of PKCε(fl/fl)AlbCre+ mice is shown to have a deletion of exon 1 and a corresponding loss of full-length PKCε mRNA and protein. The PKCε-deficient mice are shown to have the same phenotype on a chow diet as non-conditional knockout mice.

The same conditional knockouts of PKCε expression in the liver are produced by crossing or recombinant means in each of the following genetic backgrounds:
(i) yellow obese mouse (A$^{y/a}$), a dominant mutation causes the ectopic, ubiquitous expression of the agouti protein, resulting in a condition similar to adult-onset obesity and non-insulin-dependent diabetes mellitus (Michaud et al., Proc Natl Acad Sci USA 91: 2562-2566, 1994);
(ii) Obese (ob/ob) (Zhang et al Nature 372: 425-432, 1994) which are leptin-deficient;
(iii) diabetes (db/db) (Tartaglia et al., Cell 83: 1263-1271, 1995) which are deficient in active leptin receptor;
(iv) adipose (cpe/cpe) (Naggert et al., Nat. Genet. 10: 135-142, 1995) which are deficient in carboxypeptidase E; and
(v) tubby (tub/tub) (Kleyn et al., Cell 85: 281-290, 1996; Noben-Trauth et al., Nature 380: 534-548, 1996).

The glucose metabolism phenotype of each mutant is determined to establish the effect(s) of the reduced PKCε expression on the diabetic model.

Example 3

Conditional Knockout of PKCε Expression in the Pancreatic β-Islet Cells

A conditional PKCε β-islet cell-null mouse on a Cre+ background is produced using a floxed PKCε allele, PKCε (fl/fl), and Cre recombinase under control of the pdx-1 promoter (Pdx1Cre) essentially as described by Matsusue et al., J Clin Invest. 111, 737-747, 2003 for production of a liver-specific knockout. The PKCε allele for producing the knockout is the same as that used previously. The liver of PKCε(fl/fl)AlbCTe+ mice is shown to have a deletion of exon 1 and a corresponding loss of full-length PKCε mRNA and protein. The PKCε-deficient mice are shown to have the same phenotype on a chow diet as non-conditional knockout mice.

The same conditional knockouts of PKCε expression in the β-islet cells are produced by crossing or recombinant means in each of the following genetic backgrounds:
(i) yellow obese mouse (A$^{y/a}$), a dominant mutation causes the ectopic, ubiquitous expression of the agouti protein, resulting in a condition similar to adult-onset obesity and non-insulin-dependent diabetes mellitus (Michaud et al., Proc Natl Acad Sci USA 91: 2562-2566, 1994);
(ii) Obese (ob/ob) (Zhang et al., Nature 372: 425-432, 1994) which are leptin-deficient;
(iii) diabetes (db/db) (Tartaglia et al. Cell 83: 1263-1271, 1995) which are deficient in active leptin receptor;
(iv) adipose (cpe/cpe) (Naggert et al., Nat. Genet. 10: 135-142, 1995) which are deficient in carboxypeptidase E; and
(v) tubby (tub/tub) (Kleyn et al., Cell 85: 281-290, 1996; Npben-Trauth et al., Nature 380: 534-548, 1996).

The glucose, metabolism phenotype of each mutant is determined to establish the effect(s) of the reduced PKCε expression on the diabetic model.

Example 4

Conditional Knockout of PKCε Expression in the Liver and Pancreatic β-Islet Cells The conditional PKCε liver-null mouse and PKCε β-islet cell-null mouse are crossed and double null mutants isolated and tested for glucose metabolism on a variety of diets.

The double null conditional knockout is also crossed into each of the following genetic backgrounds that produce suitable diabetic models in mice:
(i) yellow obese mouse ($A^{y/a}$), a dominant mutation causes the ectopic, ubiquitous expression of the agouti protein, resulting in a condition similar to adult-onset obesity and non-insulin-dependent diabetes mellitus (Michaud et al., Proc Natl Acad Sci USA 91: 2562-2566, 1994);
(ii) Obese (ob/ob) (Zhang et al., Nature 372: 425-432, 1994) which are leptin-deficient;
(iii) diabetes (db/db) (Tartaglia et al. Cell 83: 1263-1271, 1995) which are deficient in active leptin receptor;
(iv) adipose (cpe/cpe) (Naggert et al., Nat. Genet. 10: 135-142, 1995) which are deficient in carboxypeptidase E; and
(v) tubby (tub/tub) (Kleyn et al., Cell 85: 281-290, 1996; Noben-Trauth et al., Nature 380: 534-548, 1996).

The glucose metabolism phenotype of each mutant is determined to establish the effect(s) of the reduced PKCε expression on the diabetic model.

Example 5

Glucose Homeostasis in Chow-Fed and Fat-Fed Mice

Materials and Methods
Animals

Wild type and PKCε−/− mutant mice (example 1) were used in all experiments referred to in this Example.

To induce insulin resistance in whole animals, 7-week-old mice were fed either a safflower oil-based high-fat diet for 3 weeks, or a coconut fat/sucrose-based high-fat diet, adapted from Research Diets Inc. Diet D12451, for 16 weeks.
Antibodies The commercial antibodies the inventors used were PKCα, PKCδ, PKCθ and IR (Transduction Labs.), PKCε (Santa Cruz), protein kinase B (PKB), phospho-PKB (P-S473), p42/44 mitogen activated protein kinase (MAPK) and phospho-p42/44 MAPK (P-T202/Y204) (Cell Signaling Technology) and phospho-IR (pYH62, pY1163) (Biosource).
Analysis of PKC Translocation.

The inventors fractionated quadriceps muscle from chow- and fat-fed mice and determined the distribution of PKC isoforms in cytosolic and solubilised-membrane compartments by immunoblotting and densitometry as described previously.

Glucose and Insulin Tolerance Tests.

For glucose tolerance tests, the inventors fasted mice overnight and injected them intraperitoneally with glucose (2 g/kg). The inventors obtained blood samples from the tail tip, and measured glucose concentrations using an Accu-chek Advantage II glucometer (Roche). The inventors measured serum insulin by ELISA (Mercodia AB), and serum C-peptide by RIA (Linco). For insulin tolerance tests, the inventors injected Actrapid insulin (NovoNordisk Pty Ltd) intraperitoneally (0.75 U/kg unless otherwise stated) into overnight fasted mice and collected blood samples from the tail for glucose determination.
Determination of Islet Area.

A quantitative evaluation of islet area was performed from pancreas sections stained with hematoxylin and eosin, using a digitizing tablet and BioQuant software (BIOQUANT; R&M Biometrics, Nashville, Tenn.). Results of cross-sectional islet area are expressed as percentage of the total pancreas area.
Analysis of Glucose Uptake by Isolated Muscle Strips.

The inventors killed mice by cervical dislocation and removed soleus muscles immediately. The inventors preincubated muscles in the presence or absence of insulin, and glucose transport activity was assayed as described previously.
Assessment of Insulin Action In Vivo The inventors injected tracer amounts of [U-$^{14}$C]glucose and [3-$^{3}$H]2-deoxyglucose (10 µCi per mouse), with glucose (2 g/kg), intraperitoneally into overnight fasted mice. Alternatively, the inventors injected [1-$^{14}$C]2-deoxyglucose (10 µCi per mouse) with insulin (0.5 U/kg). During these radiolabeled glucose and insulin tolerance tests, the inventors collected blood from tail rips and determined blood radioactivity to calculate the areas under the curves. The inventors determined uptake of [3-$^{3}$H]2-deoxyglucose or [1-$^{14}$C]2-deoxyglucose, and incorporation of [U-$^{14}$C]glucose into glycogen or lipid, in samples of muscle, liver and adipose tissue as described previously, and made correction for the area under the curve for radioactive glucose and for the weight of the tissue sample used.
Statistical Analysis.

Figure 2B:
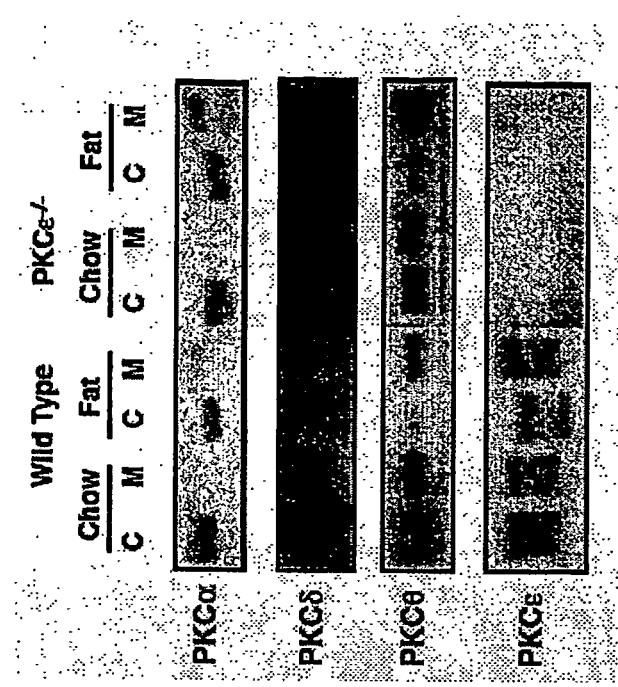
Figure 2A:
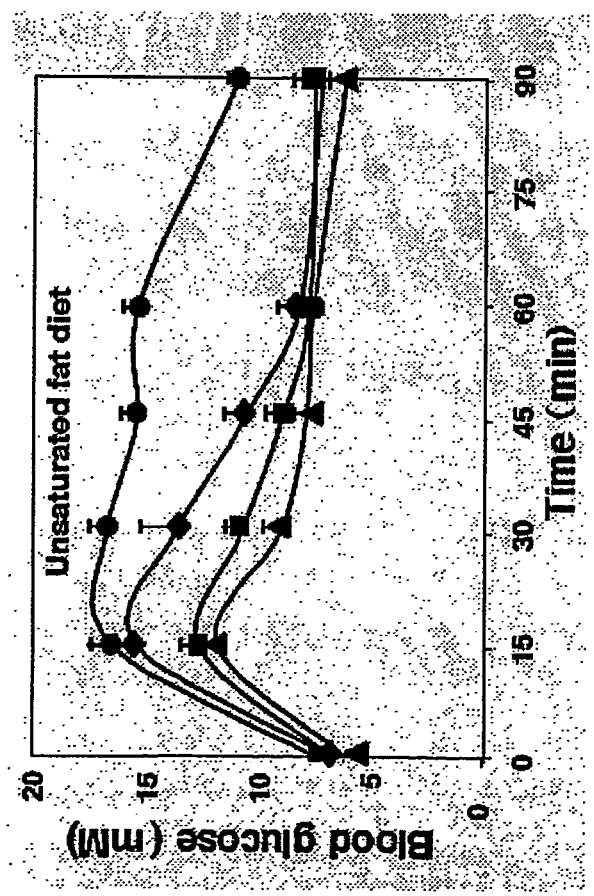
FIG. 2a is a graphical representation showing the effects of an unsaturated fat diet on blood glucose levels in PKCε$^{-/-}$ mice compared to wild type animals, during an intraperitoneal glucose tolerance test. Wild type (n=17) (●) and PKCε$^{-/-}$ (n=15) (■) mice were fed an unsaturated fat diet, and in a control experiment, age-matched wild type (n=12) (♦) and PKCε$^{-/-}$ (n=9) (▲) mice fed a standard chow diet. ANOVA: P<0.001 for diet effect in wild type mice; P<0.001 for genotype effect in fat-fed mice.
Figure 2C:
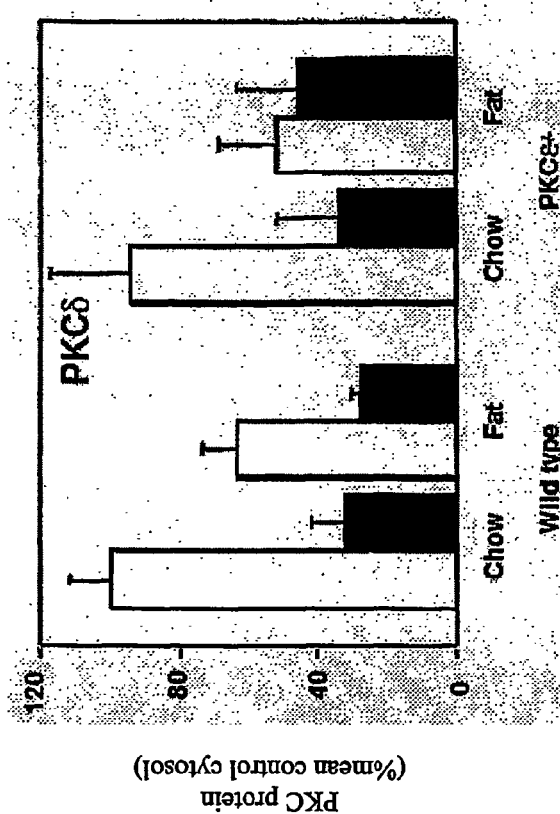
FIG. 2c is a graphical representation showing the quantification of PKCα in immunoblots in the cytosolic and solubilised membrane fractions of skeletal muscle from the chow-fed and unsaturated fat-fed mice described in the legend to FIG. 2b. Data are expressed as a percentage of the average level of PKCα in the cytosol of wild-type mice receiving a chow diet. The x-axis shows the genotype of mice and the diet received (i.e., chow or fat). Open bars are cytosolic fraction. Filled bars are solubilised membrane fractions. The means from 5-6 mice per group are shown.
Figure 2D:
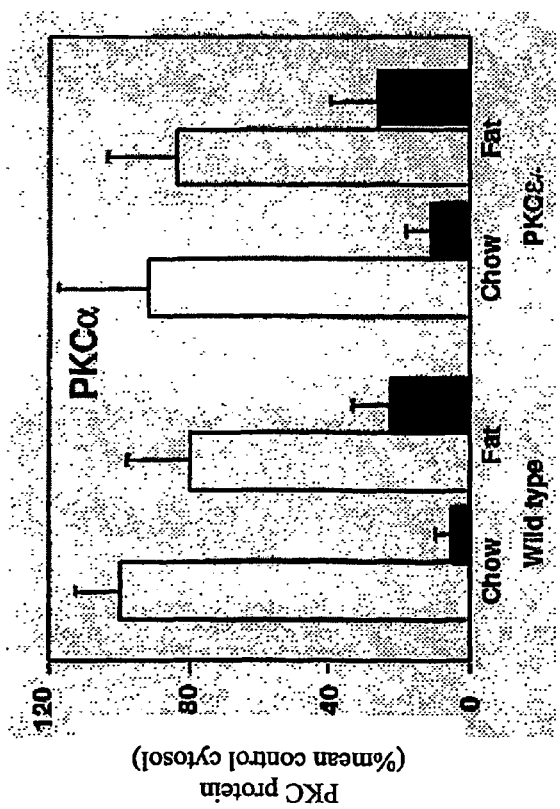
FIG. 2d is a graphical representation showing the quantification of PKCδ in immunoblots in the cytosolic and solubilised membrane fractions of skeletal muscle from the chow-fed and unsaturated fat-fed mice described in the legend to FIG. 2b. Data are expressed as a percentage of the average level of PKCδ in the cytosol of wild-type mice receiving a chow diet. The x-axis shows the genotype of mice and the diet received (i.e., chow or fat). Open bars are cytosolic fraction. Filled bars are solubilised membrane fractions. The means from 5-6 mice per group are shown.
Figure 2F:
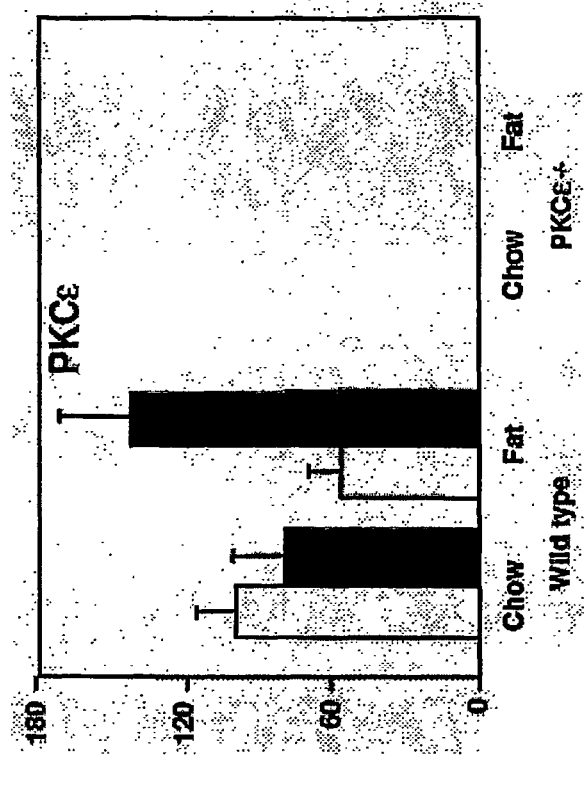
FIG. 2f is a graphical representation showing the quantification of PKCε in immunoblots in the cytosolic and solubilised membrane fractions of skeletal muscle from the chow-fed and unsaturated fat-fed mice described in the legend to FIG. 2b. Data are expressed as a percentage of the average level of PKCε in the cytosol of wild-type mice receiving a chow diet. The x-axis shows the genotype of mice and the diet received (i.e., chow or fat). Open bars are cytosolic fraction. Filled bars are solubilised membrane fractions. The means from 5-6 mice per group are shown.
Figure 2E:
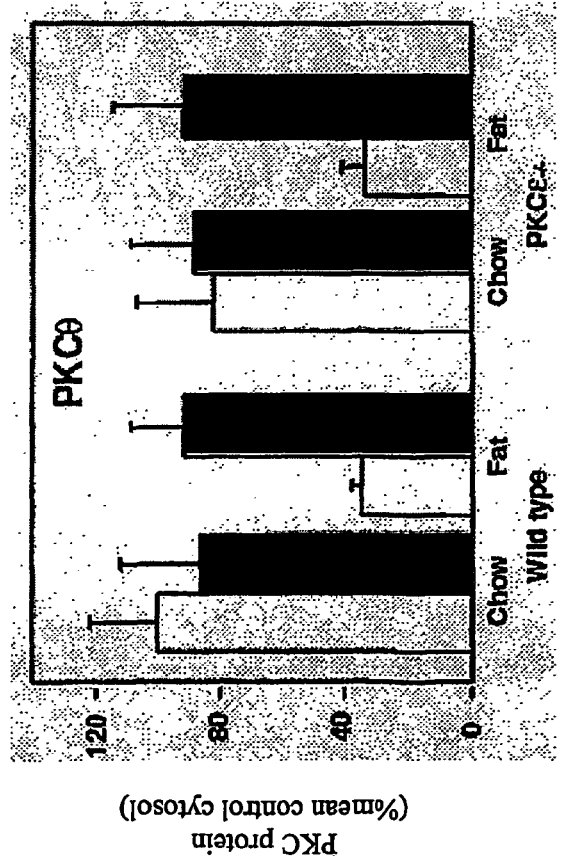
FIG. 2e is a graphical representation showing the quantification of PKCθ in immunoblots in the cytosolic and solubilised membrane fractions of skeletal muscle from the chow-fed and unsaturated fat-fed mice described in the legend to FIG. 2b, Data are expressed as a percentage of the average level of PKCθ in the cytosol of wild-type mice receiving a chow diet. The x-axis shows the genotype of mice and the diet received (i.e., chow or fat). Open bars are cytosolic fraction. Filled bars are solubilised membrane fractions. The means from 5-6 mice per group are shown.
Figure 3A:
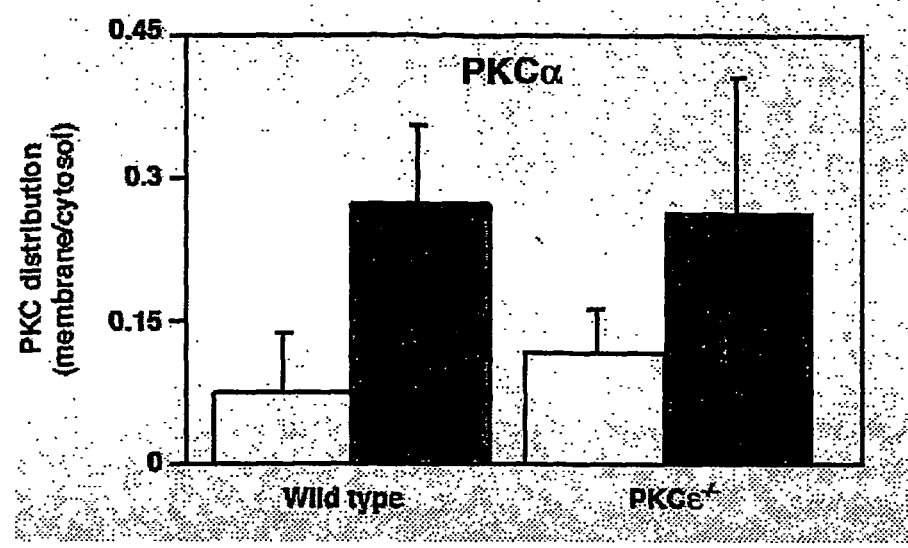
FIG. 3a is a graphical representation showing the ratio of the membrane-associated PKCα to the cytosolic PKCα for chow-fed (open bars) and unsaturated fat-fed (filled bars) mice described in the legend to FIG. 2b. The x-axis shows the genotype of mice. The means from 5-6 mice per group axe shown. ANOVA: * P<0.05;  P<0.02; * P<0.0075 for diet effect; † P<0.05 for genotype effect.
Figure 3B:
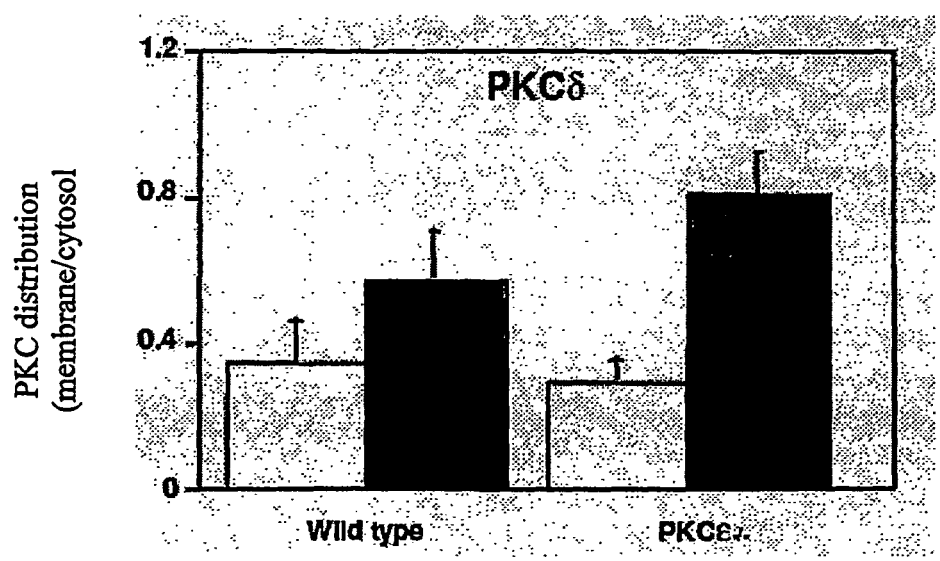
FIG. 3b is a graphical representation showing the ratio of the membrane-associated PKCδ to the cytosolic PKCδ for chow-fed (open bars) and unsaturated fat-fed (filled bars) mice described in the legend to FIG. 2b. The x-axis shows the genotype of mice. The means from 5-6 mice per group are shown. ANOVA: *** P<0.0075 for diet effect.
Figure 3C:
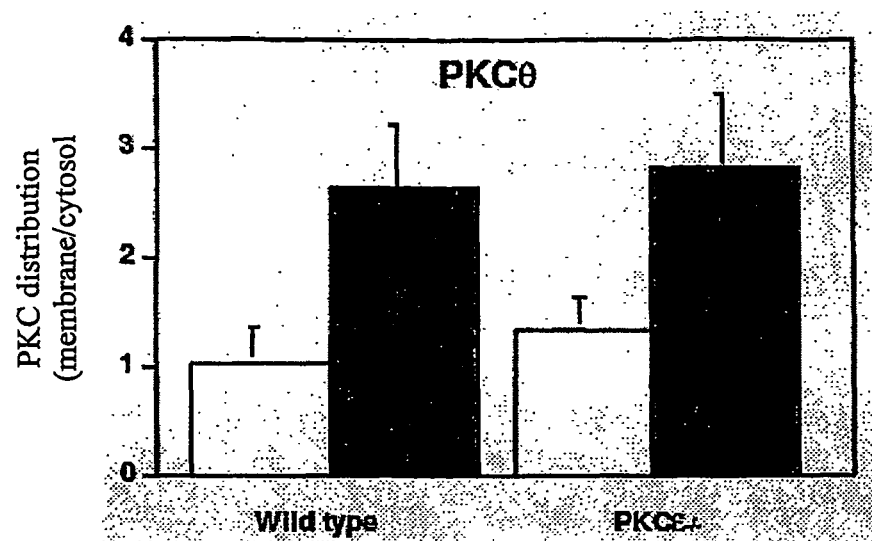
FIG. 3c is a graphical representation showing the ratio of the membrane-associated PKCθ to the cytosolic PKCθ for chow-fed (open bars) and unsaturated fat-fed (filled bars) mice described in the legend to FIG. 2b. The x-axis shows the genotype of mice. The means from 5-6 mice per group are shown. ANOVA: *** P<0.0075 for diet effect.
Figure 3D:
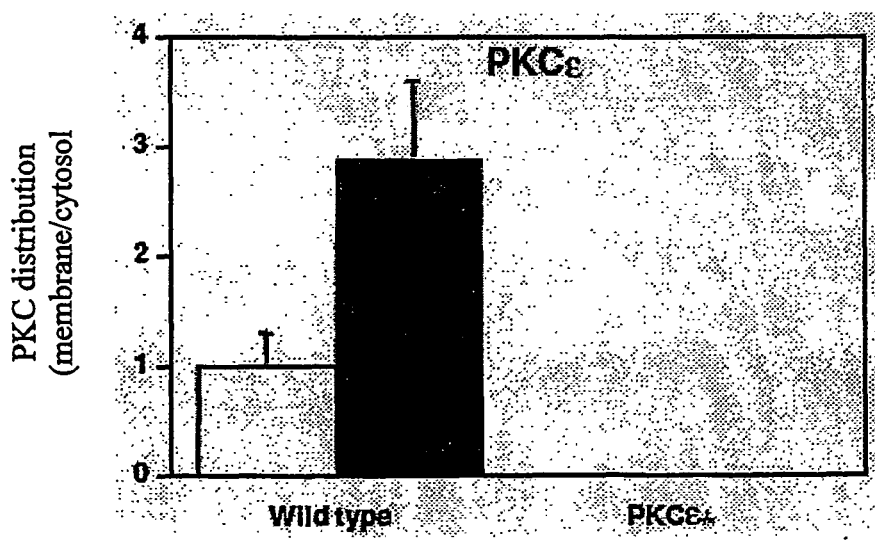
FIG. 3d is a graphical representation showing the ratio of the membrane-associated PKCε to the cytosolic PKCε for chow-fed (open bars) and unsaturated fat-fed (filled bars) mice described in the legend to FIG. 2b. The x-axis shows the genotype of mice. The means from 5-6 mice per group are shown. ANOVA: * P<0.05 for diet effect.

The inventors analysed results by Student's t-test or ANOVA using Statview 4.5 for Macintosh (Abacus Concepts). Results are expressed ±standard error, and differences were considered to be statistically significant at $P<0.05$.
Results
Effect of High-Saturated and -Unsaturated Fat Diets on Glucose Homeostasis in Wild Type and PRCε$^{-/-}$ Mice Fat-feeding is a well-documented protocol for inducing obesity and insulin resistance in rodents. The inventors firstly employed a diet predominantly enriched in the unsaturated fatty acid linoleate (59% of calories derived from safflower oil) which promotes skeletal muscle and liver insulin resistance in the absence of gross hyperglycemia and hyperinsulinemia. As expected, wild type mice fed this diet for 3 weeks were unable to restore blood glucose levels as efficiently as chow-fed control animals when subjected to a glucose tolerance test (FIG. 2a). In contrast, PKCε$^{-/-}$ mice were profoundly protected from the effect of the fat diet, and were significantly more glucose tolerant than even chow-fed wild type mice (FIG. 2a). This protection could not be explained by differences between fat-fed wild type and PKCε$^{-/-}$ mice in energy intake, adipose tissue accumulation or liver and muscle triglyceride content (Table 1), suggesting a specific requirement for PKCε in the development of fat-induced insulin resistance.

TABLE 1

Effect of unsaturated fat diet on wild type and PKCε$^{-/-}$ mice

| | Wild type | | PKCε$^{-/-}$ | |
|---|---|---|---|---|
| | Chow (n = 12) | Fat (n = 17) | Chow (n = 9) | Fat (n = 15) |
| Body weight (g) | 27.1 ± 0.7 | 27.9 ± 0.6 | 26.2 ± 1.0 | 24.8 ± 0.8§ |
| Energy Intake | 2.3 ± 0.1 | 2.6 ± 0.1 | 2.3 ± 0.1 | 2.4 ± 0.2 |
| Fasting blood glucose | 6.2 ± 0.8 | 7.4 ± 0.7 | 5.9 ± 0.4 | 7.2 ± 0.6 |
| Energy intake¶¶ | 3.1 ± 0.2 | 2.6 ± 0.1 | 3.1 ± 0.2 | 2.4 ± 0.2 |
| Epidydimal fat† | 14.1 ± 1.7 | 23.7 ± 3.0* | 16.1 ± 2.3 | 28.0 ± 4.1‡ |
| Retroperirenal fat† | 3.9 ± 0.8 | 8.0 ± 1.5* | 3.0 ± 0.4 | 8.2 ± 1.7‡ |
| Brown adipose tissue† | 2.9 ± 0.4 | 3.6 ± 0.2 | 3.7 ± 0.3 | 2.9 ± 0.4 |
| Liver† | 41.1 ± 2.9 | 41.9 ± 3.0 | 44.7 ± 3.9 | 34.6 ± 2.8‡!! |
| Heart† | 5.9 ± 0.6 | 6.2 ± 0.5 | 6.5 ± 1.3 | 5.8 ± 0.3 |
| Spleen† | 3.0 ± 0.3 | 2.8 ± 0.2 | 2.7 ± 0.6 | 3.4 ± 0.4 |
| Pancreas† | 7.8 ± 1.0 | 8.7 ± 1.1 | 7.1 ± 1.2 | 7.8 ± 1.1 |
| Liver triglycerides†† | 1.5 ± 0.2 | 4.5 ± 0.9* | 1.5 ± 0.1 | 4.0 ± 1.3‡ |
| Muscle triglycerides†† | 1.2 ± 0.1 | 2.0 ± 0.3* | 1.1 ± 0.2 | 1.8 ± 0.4‡ |

¶(mM);
¶¶(kJ · g body wt$^{-1}$ · d$^{-1}$);
†(mg · g body wt.$^{-1}$);
††(μmol · g$^{-1}$).
Significance of comparisons:
*P < 0.05 fat-fed wild type versus chow-fed wild type mice;
§P < 0.01 PKCε$^{-/-}$ versus appropriate wild type control;
‡P < 0.05 fat-fed PKGε$^{-/-}$ versus chow-fed PKCε$^{-/-}$ mice Consistent with this interpretation, and with the inventors earlier studies involving rats, wild type mice fed this diet also showed specific patterns of PKC redistribution in skeletal muscle: minimal effects on PKCα; increased translocation of PKCε from cytosol to membrane (indicating activation) and diminished expression of PKCδ and PKC in cytosol, most likely resulting from translocation to, and subsequent down regulation in membrane fractions (FIGS. 2b-2f; FIG. 3a-3d). The inventors observed essentially similar alterations in skeletal muscle from fat-fed PKCε$^{-/-}$ mice, apart from the absence of PKCε itself, clearly suggesting that the expression or activation of other novel PKCs had not been altered in compensation for the deletion of PKCε (FIGS. 2b-2f; FIG. 3a-3d).

Figure 4B:
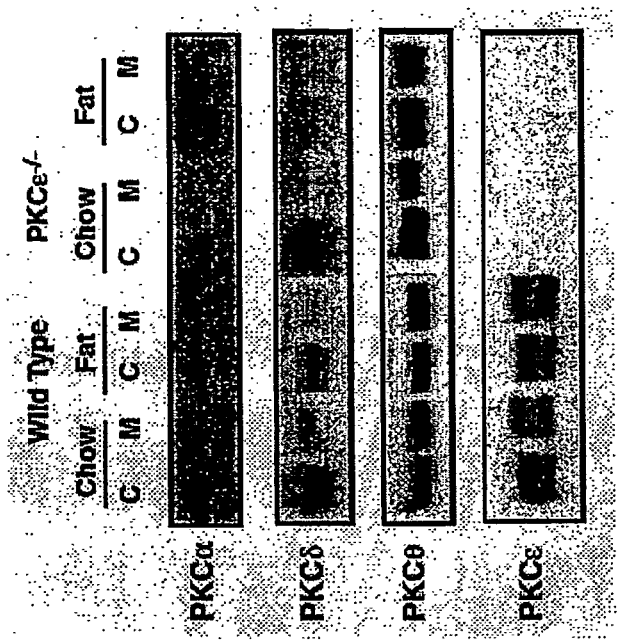
Figure 4A:
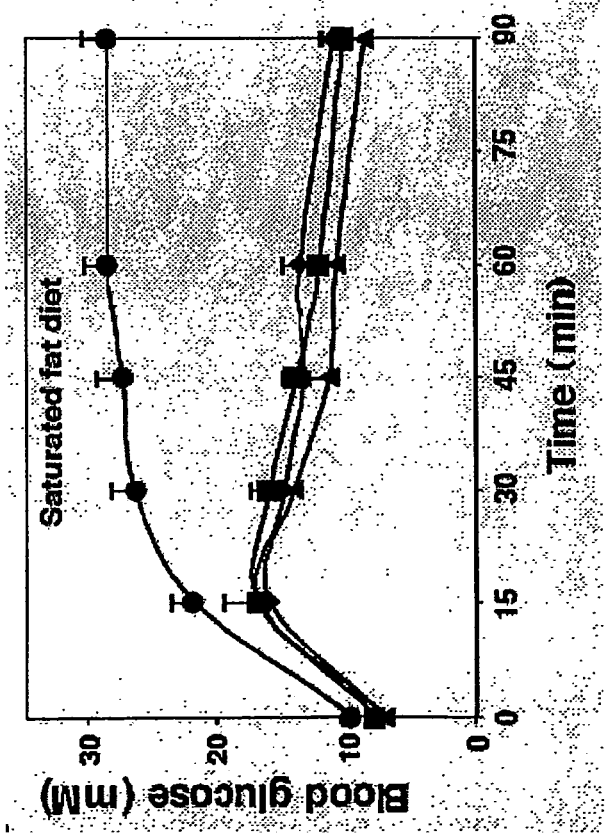
FIG. 4a is a graphical representation showing the effects of a saturated fat diet on blood glucose levels in PKCε$^{-/-}$ mice compared to wild type animals, during an intraperitoneal glucose tolerance test. Wild type (n=9) (●) and PKCε$^{-/-}$ (n=8) (■) mice were fed a saturated fat diet, and in a control experiment, age-matched wild type (n=10) (♦) and PKCε$^{-/-}$ (n=5) (▲) mice fed a standard chow diet. ANOVA: P<0.001 for diet effect in wild type mice; P<0.001 for genotype effect in fat-fed mice.
Figure 4F:
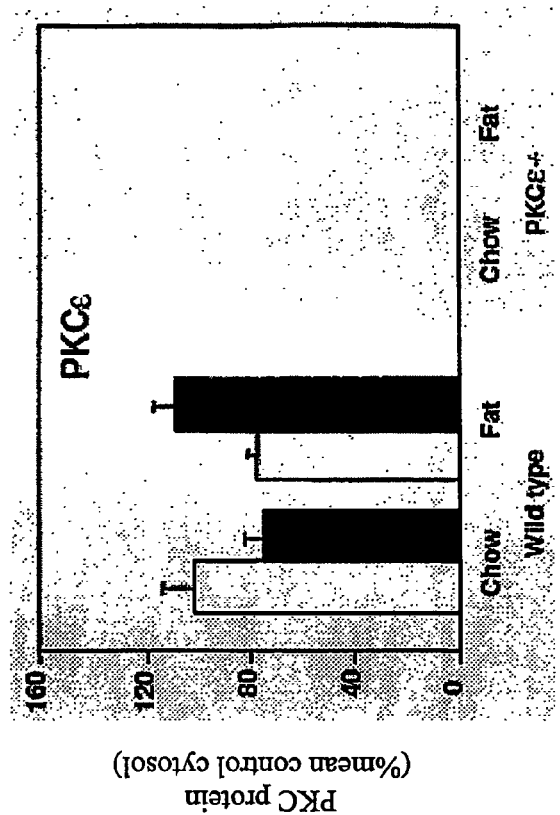
FIG. 4f is a graphical representation showing the quantification of PKCε in immunoblots in the cytosolic and solubilised membrane fractions of skeletal muscle from the chow-fed and saturated fat-fed mice described in the legend to FIG. 4b. Data are expressed as a percentage of the average level of PKCε in the cytosol of wild-type mice receiving a chow diet. The x-axis shows the genotype of mice and the diet received (i.e., chow or fat). Open bars are cytosolic fraction. Filled bars are solubilised membrane fractions. The means from 5-6 mice per group are shown.
Figure 4E:
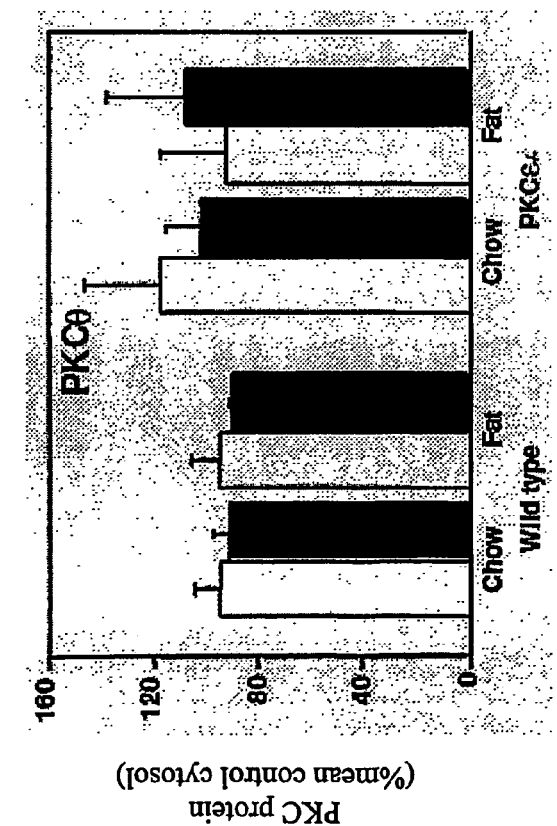
FIG. 4e is a graphical representation showing the quantification of PKCθ in immunoblots in the cytosolic and solubilised membrane fractions of skeletal muscle from the chow-fed and saturated fat-fed mice described in the legend to FIG. 4b. Data are expressed as a percentage of the average level of PKCθ in the cytosol of wild-type mice receiving a chow diet. The x-axis shows the genotype of mice and the diet received (i.e., chow or fat). Open bars are cytosolic fraction. Filled bars are solubilised membrane fractions. The means from 5-6 mice per group are shown.
Figure 5B:
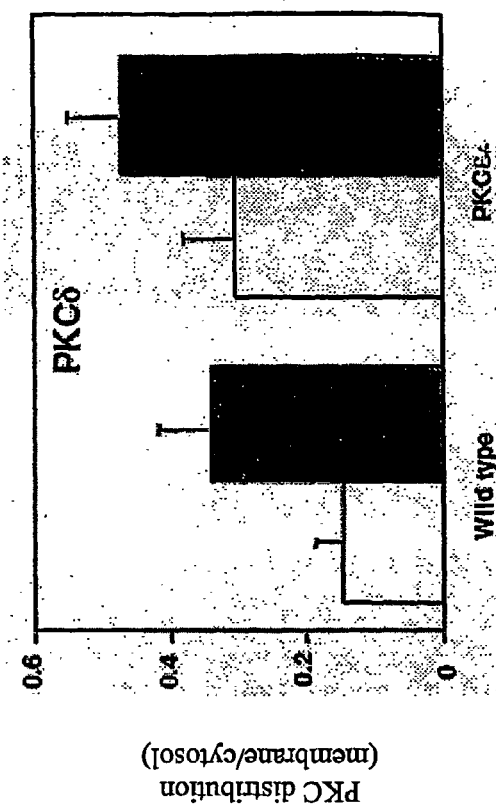
FIG. 5b is a graphical representation showing the ratio of the membrane-associated PKCδ to the cytosolic PKCδ for chow-fed (open bars) and saturated fat-fed (filled bars) mice described in the legend to FIG. 4b. The x-axis shows the genotype of mice. The means from 5-6 mice per group are shown. ANOVA: ** P<0.02 for diet effect; P<0.05 for genotype effect.
Figure 5A:
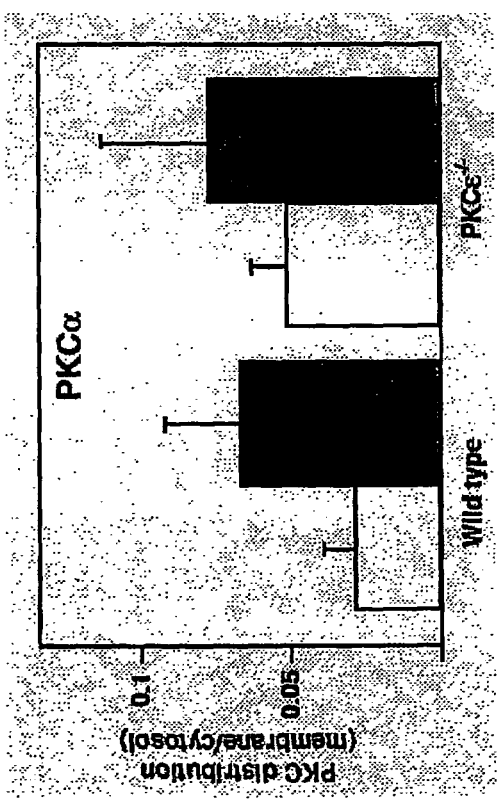
FIG. 5a is a graphical representation showing the ratio of the membrane-associated PKCα to the cytosolic PKCα for chow-fed (open bars) and saturated fat-fed (filled bars) mice described in the legend to FIG. 4b. The x-axis shows the genotype of mice. The means from 5-6 mice per group are shown.
Figure 5D:
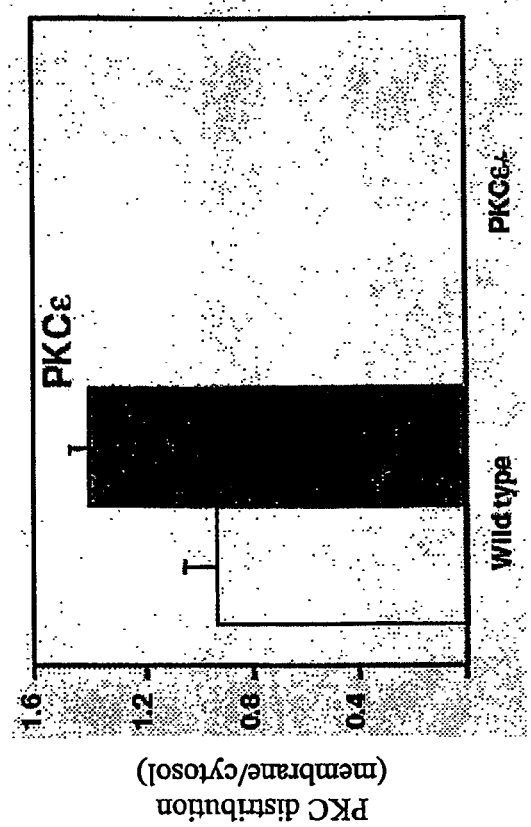
FIG. 5d is a graphical representation showing the ratio of the membrane-associated PKCδ to the cytosolic PKCε for chow-fed (open bars) and saturated fat-fed (filled bars) mice described in the legend to FIG. 4b. The x-axis shows the genotype of mice. The means from 5-6 mice per group are shown. ANOVA: * P<0.05 for diet effect.
Figure 5C:
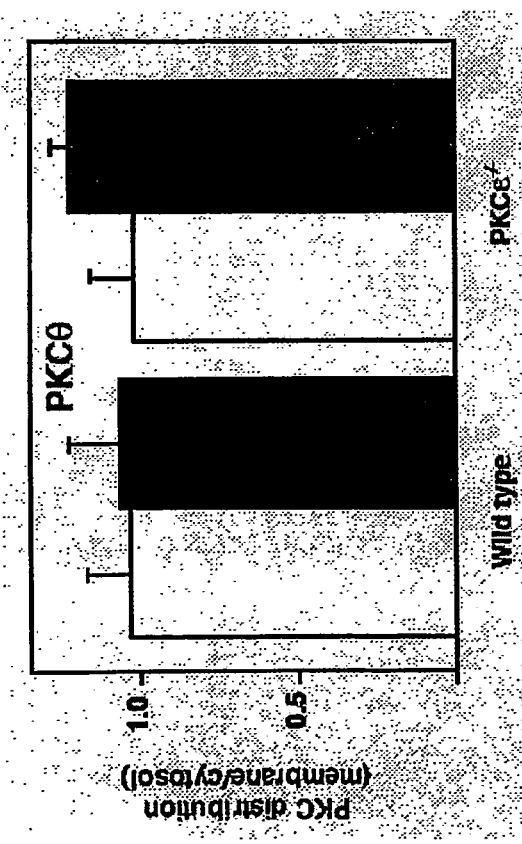
FIG. 5c is a graphical representation showing the ratio of the membrane-associated PKCθ to the cytosolic PKCθ for chow-fed (open bars) and saturated fat-fed (filled bars) mice described in the legend to FIG. 4b. The x-axis shows the genotype of mice. The means from 5-6 mice per group are shown.

The inventors additionally employed a high-saturated fat diet for 16 weeks, in which 45% of calories are derived from fat (principally the saturated free fatty acid palmitate). This regimen significantly increased fasting blood glucose levels in wild type mice (Table 2) and, compared to the unsaturated fat diet, provoked an even greater impairment of glucose disposal during the glucose tolerance test (FIG. 4a).

TABLE 2

Effect of high-saturated fat diet on wild type and PKCε$^{-/-}$ mice

| | Wild type | | PKCε$^{-/-}$ | |
|---|---|---|---|---|
| | Chow (n = 10) | Fat (n = 9) | Chow (n = 5) | Fat (n = 8) |
| Body weight (g) | 32.1 ± 0.7 | 43.4 ± 2.6** | 30.9 ± 1.6 | 42.6 ± 1.8** |
| Fasting blood glucose | 7.0 ± 0.3 | 9.4 ± 0.4‡ | 7.2 ± 0.3 | 8.1 ± 0.3‡‡ |
| Epidydimal fat† | 15.2 ± 1.0 | 46.2 ± 4.6‡ | 17.2 ± 0.9 | 55.7 ± 4.7** |
| Retroperirenal fat† | 6.0 ± 0.7 | 17.6 ± 1.1‡ | 6.4 ± 0.9 | 18.5 ± 1.6** |
| Brown adipose tissue† | 3.3 ± 0.3 | 5.4 ± 0.4‡ | 3.6 ± 0.3 | 6.9 ± 0.8* |
| Liver† | 47.6 ± 1.6 | 39.4 ± 1.7* | 50.9 ± 2.5 | 37.8 ± 3.1* |
| Heart† | 4.6 ± 0.2 | 3.6 ± 0.1** | 4.5 ± 0.4 | 3.8 ± 0.2** |

¶(mM);
¶¶(kJ · g body wt$^{-1}$ · d$^{-1}$);
†(mg · g body wt.$^{-1}$).
Significance of comparisons:
*P < 0.05,
**P < 0.01,
‡P < 0.001 fat-fed wild type or PKCε$^{-/-}$ versus chow-fed wild type;
‡‡P < 0.02 fat-fed PKCε$^{-/-}$ versus fat-fed wild type.

Remarkably, the fasting hyperglycemia was reduced in fat-fed PKCε$^{-/-}$ mice and glucose tolerance was completely normalised. Consistent with an obligatory role for PKCε in mediating insulin resistance, the saturated fat diet also promoted translocation of this PKC isoform in skeletal muscle (FIGS. 4*b*-4*f* and FIGS. 5*a*-5*d*). Expression of the other PKC isoforms was again not different between muscle from wild type and PKCε$^{-/-}$ mice, and cellular redistribution was generally similar to the effects seen with the unsaturated diet. The exception was PKCθ which was unaltered by saturated fat-feeding, suggesting that its activation is not necessary for the pronounced insulin resistance that accompanies this model (FIGS. 4*b*-4*f* and FIGS. 5*a*-5*d*). As above, the protection afforded by deletion of PKCε could not be explained by alterations in tissue or body weight, or energy intake (Table 2).

Taken together these data suggest that an enhancement of insulin sensitivity in skeletal muscle would be the most obvious explanation for the pronounced improvement in glucose tolerance seen in PKCε$^{-/-}$ mice and the protection against the effects of fat-feeding.

Insulin and C-Peptide Levels in Wild Type and PKCε$^{-/-}$ Mice

Alternative explanations, however, were suggested by alterations in the profiles of serum insulin and C-peptide during the glucose tolerance tests. Insulin levels are a combined measure of secretion from β-cells and clearance by the liver, whereas C-peptide is a more direct measure of β-cell responsiveness, because it is co-secreted with insulin but not rapidly cleared by the liver.

Figure 6B:
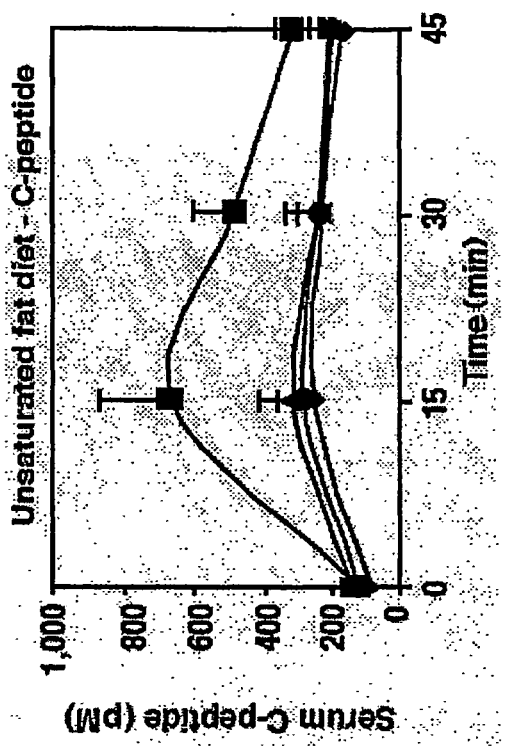
FIG. 6b is a graphical representation showing the effect of PKCε deletion on serum C-peptide levels in wild type (■) and PKCε$^{-/-}$ (●) mice fed an unsaturated fat diet, and age-matched wild type (♦) and PKCε$^{-/-}$ (▲) mice fed a standard chow diet, during the glucose tolerance test as described in the legend to FIG. 2. ANOVA: P<0.005 for genotype effect on fat-fed mice. Results shown are the means±SEM for 4-12 mice per group.
Figure 6A:
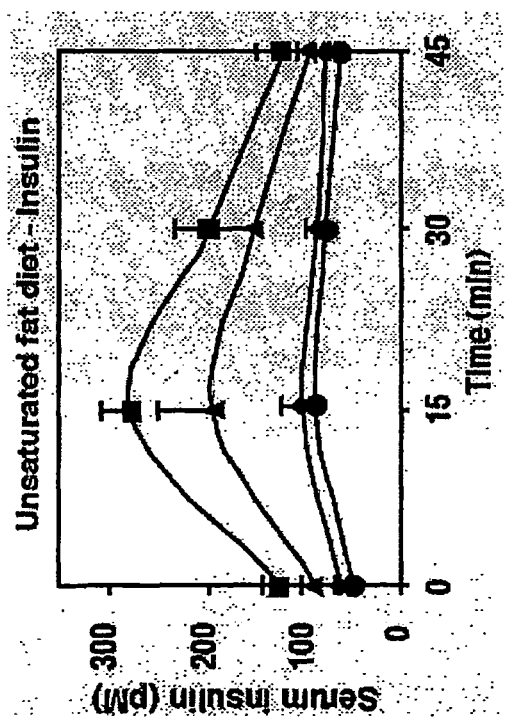
FIG. 6a is a graphical representation showing the effect of PKCε deletion on serum insulin levels in wild type (■) and PKCε$^{-/-}$ (■) mice fed an unsaturated fat diet, and age-matched wild type (♦) and PKCε$^{-/-}$ (▲) mice fed a standard chow diet, during the glucose tolerance test as described in the legend to FIG. 2. ANOVA: P<0.001 for genotype effect; P<0.01 for combined genotype and diet effect. Results shown are the means±SEM for 4-12 mice per group.
Figure 6D:
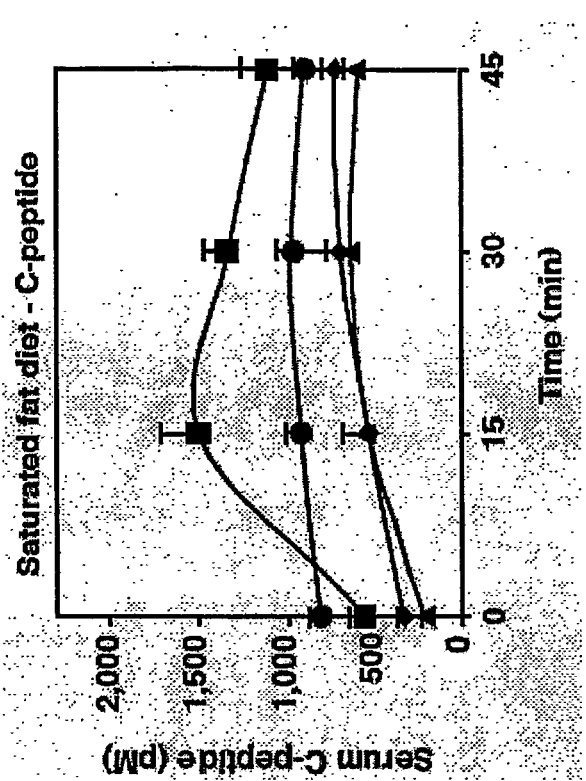
FIG. 6d is a graphical representation showing the effect of PKCε deletion on serum C-peptide levels in wild type (■) and PKCε$^{-/-}$ (●) mice fed a saturated fat diet, and age-matched wild type (♦) and PKCε$^{-/-}$ (▲) mice fed a standard chow diet, during the glucose tolerance test as described in the legend to FIG. 4. ANOVA: P<0.001 for genotype effect. Results shown are the means±SEM for 4-12 mice per group.
Figure 6C:
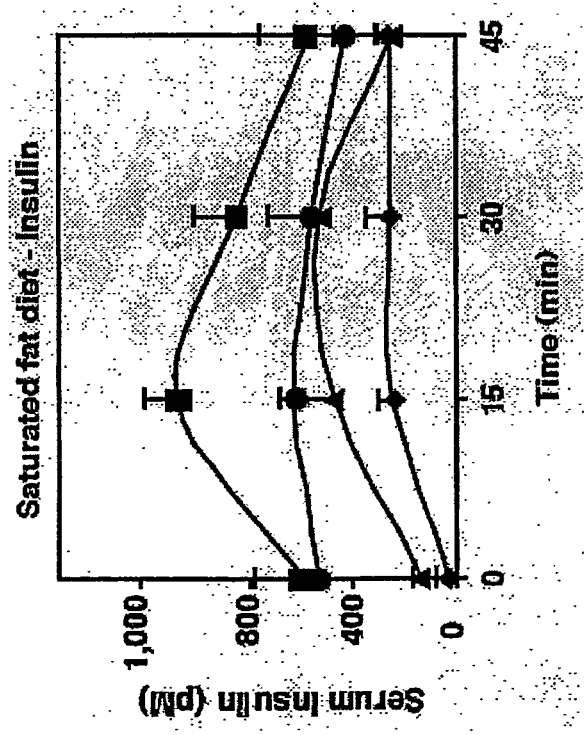
FIG. 6c is a graphical representation showing the effect of PKCε deletion on serum insulin levels in wild type (■) and PKCε$^{-/-}$ (●) mice fed a saturated fat diet, and age-matched wild type (♦) and PKCε$^{-/-}$ (▲) mice fed a standard chow diet, during the glucose tolerance test as described in the legend to FIG. 4. ANOVA: P<0.001 for diet effect; P<0.002 for genotype effect. Results shown are the means±SEM for 4-12 mice per group.

Insulin levels during the glucose tolerance test were similar in wild type mice irrespective of whether they had been maintained on standard chow or an unsaturated fat diet (FIG. 6*a*). Insulin excursions, however, were significantly increased in the PKCε$^{-/-}$ mice, especially those fed the high-fat diet (FIGS. 6*a*, 6*c*).

Comparison with the corresponding C-peptide data indicates that two independent effects contributed to this augmentation in PKCε$^{-/-}$ mice (FIG. 6*b*). Firstly, there was a diminished capacity to clear insulin which was independent of diet, since insulin, but not C-peptide, was increased in chow-fed PKCε$^{-/-}$ mice. Secondly, ablation of PKCs enhanced secretory capacity specifically in the animals maintained on the fat diet, as witnessed by C-peptide levels (FIG. 6*b*). These results were broadly confirmed in animals fed the longer-term saturated fat diet (FIG. 6*d*), although under these conditions wild type mice exhibited both higher insulin and C-peptide levels compared to chow-fed controls at the commencement of the glucose tolerance test, which did not increase further over the ensuing time course (FIGS. 6*c*, 6*d*). In contrast, both plasma insulin (FIG. 6*c*) and C-peptide levels (FIG. 6*d*) were robustly increased following the glucose challenge in fat-fed PKCε$^{-/-}$ mice despite, in the case of C-peptide, starting from a lower baseline (FIG. 6*d*).

Figure 6E:
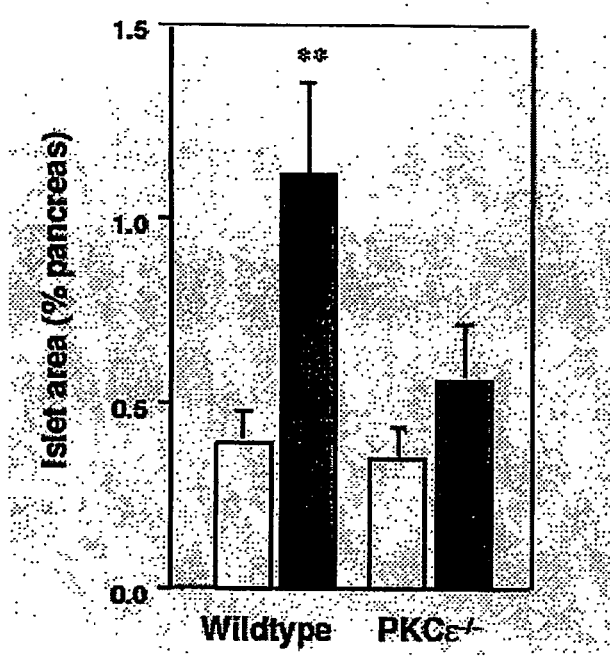
FIG. 6e is a graphical representation showing a comparison of islet area as a percentage of total pancreas from wild type and PKCε$^{-/-}$ mice fed either a chow diet (open bars) or a saturated fat diet (filled bars) t-test ** P<0.01, fat-fed wild type mice versus chow-fed wild type mice.

Enhanced secretory responsiveness was not simply a function of alterations in islet size (FIG. 6*e*). Indeed, fat-fed wild type mice showed islet hyperplasia as previously seen in insulin resistant models, but this was normalised by deletion of PKCε in keeping with the restoration of glucose tolerance. In pancreatic sections from chow-fed mice, islet area was found to be independent of PKC expression.

Taken together, the above experiments demonstrate that deletion of PKCε facilitates a compensatory enhancement of insulin secretion specifically in mice maintained on either of the high-fat diets. Moreover, insulin clearance is diminished in the PKCε$^{-/-}$ mice irrespective of diet.

Effect of Fat Diets on Peripheral Tissue Insulin Action in Wild Type and PKCε$^{-/-}$ Mice While the above data indicate that increased availability of insulin might contribute to the improvement in glucose tolerance observed in PKCε$^{-/-}$ mice, they do not exclude an independent effect on insulin sensitivity. The inventors therefore investigated this more directly using intraperitoneal insulin tolerance tests. Although, as expected, wild type mice maintained on the saturated fat diet were unable to reduce blood glucose levels to the same concentration as chow-fed mice in response to insulin (FIG. 7*a*), PKCε deletion did not overcome this defect.

Figure 7B:
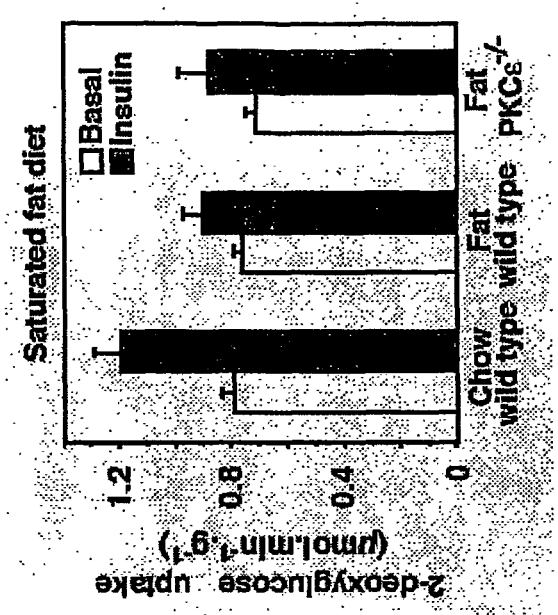
FIG. 7b is a graphical representation showing basal and sub-maximal (300 μU/ml) insulin-stimulated 2-deoxyglucose uptake by isolated soleus muscle from wild-type and PKCε$^{-/-}$ mice fed a high-saturated fat, compared to wild-type mice fed a chow diet (n=8-10). Open bars represent basal uptake. Filled bars represent insulin-stimulated uptake. ANOVA: P<0.005 for diet effect.
Figure 7A:
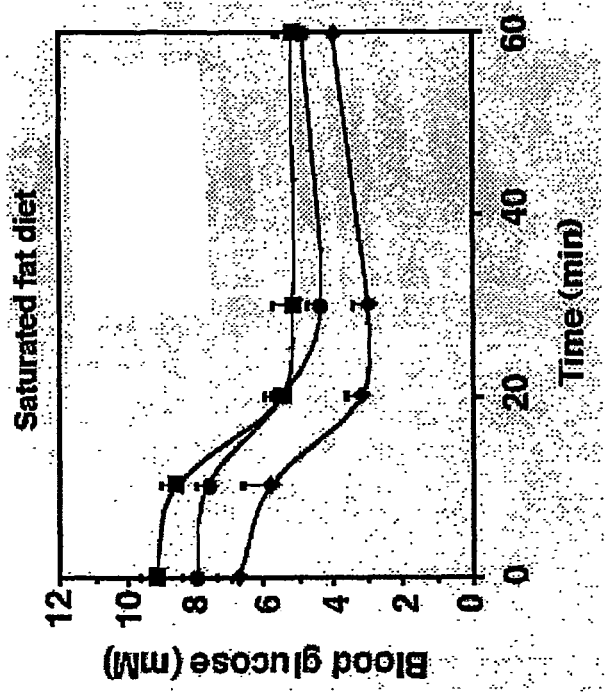
FIG. 7a is a graphical representation showing blood glucose levels during an intraperitoneal insulin tolerance test of wild type and PKCε$^{-/-}$ mice fed a saturated fat diet, and age-matched wild type mice fed a standard chow diet (n=8-10 per group) ♦, wild-type mice on chow diet; ■, wild-type mice on saturated fat diet; ●, PKCε$^{-/-}$ mice on saturated fat diet. ANOVA: P<0.001 for diet effect on wild type mice; P<0.02 for genotype effect on fat-fed mice.

The inventors examined insulin action more closely in skeletal muscle using isolated soleus muscle preparations. The saturated fat diet reduced sub-maximal insulin-stimulated glucose uptake by soleus muscle, but once again this was not reversed by PKCε deletion (FIG. 7*b*).

Figure 7D:
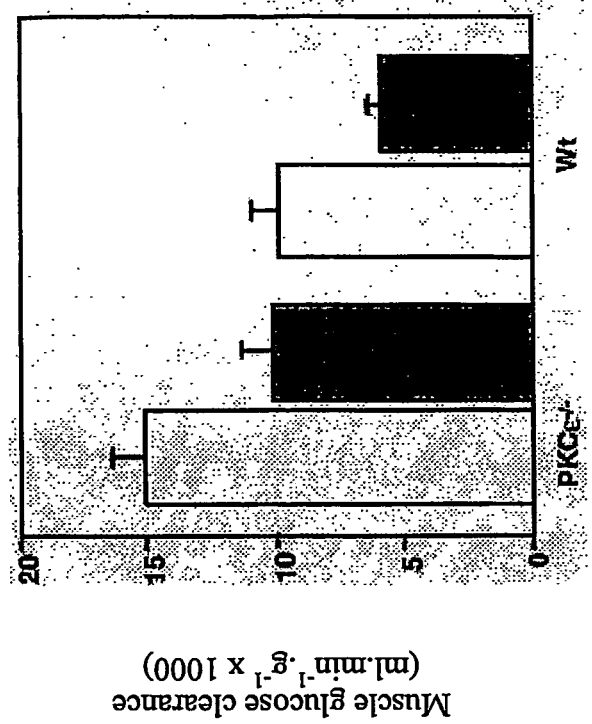
FIG. 7d is a graphical representation showing [3-$^3$H]2-deoxyglucose clearance during an intraperitoneal glucose tolerance test by skeletal muscle from wild type and PKCε$^{-/-}$ mice fed a high-unsaturated fat diet (filled bars), and age-matched wild type and PKCε$^{-/-}$ mice fed a standard chow diet (open bars) (n=6 per group). ANOVA: P<0.0075 for diet effect; P<0.015 for genotype effect.
Figure 7C:
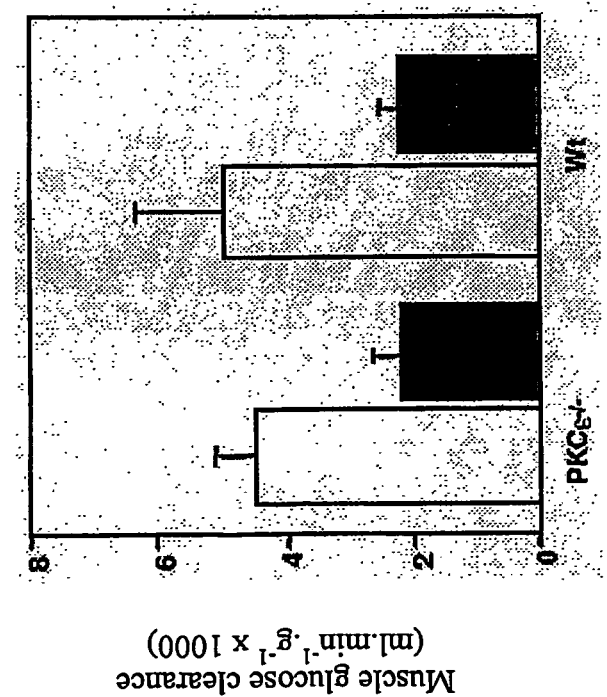
FIG. 7c is a graphical representation showing [$^{14}$C]2-deoxyglucose clearance into skeletal muscle during an intravenous insulin tolerance test of wild type (n=17) and PKCε$^{-/-}$ (n=10) mice fed an unsaturated fat diet (filled bars), and age-matched wild type (n=9) and PKCε$^{-/-}$ (n=8) mice fed a standard chow diet (open bars).
Figure 7E:
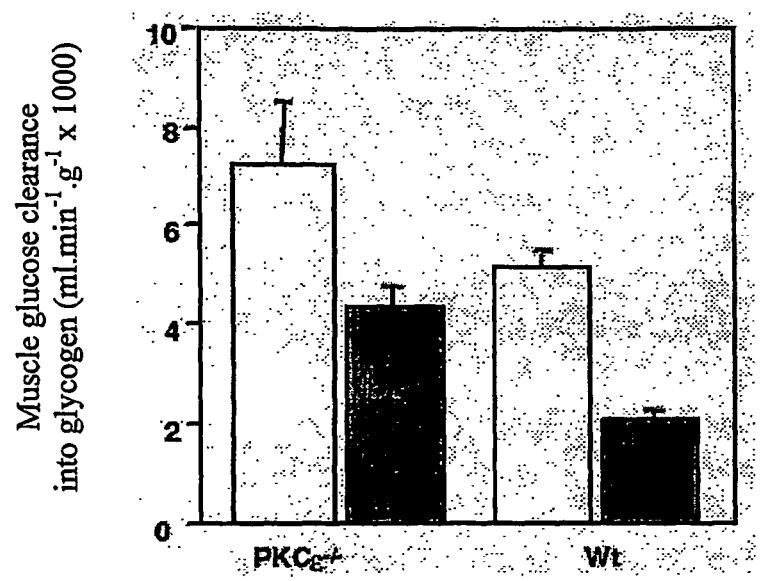
FIG. 7e is a graphical representation showing [$^{14}$C]glucose clearance into glycogen by skeletal muscle from mice treated as described in the legend to FIG. 7d. ANOVA: P<0.02 for diet effect; P<0.002 for genotype effect. Open bars represent mice fed on a chow diet. Filled bars represent mice fed on a high-unsaturated fat diet.
Figure 8B:
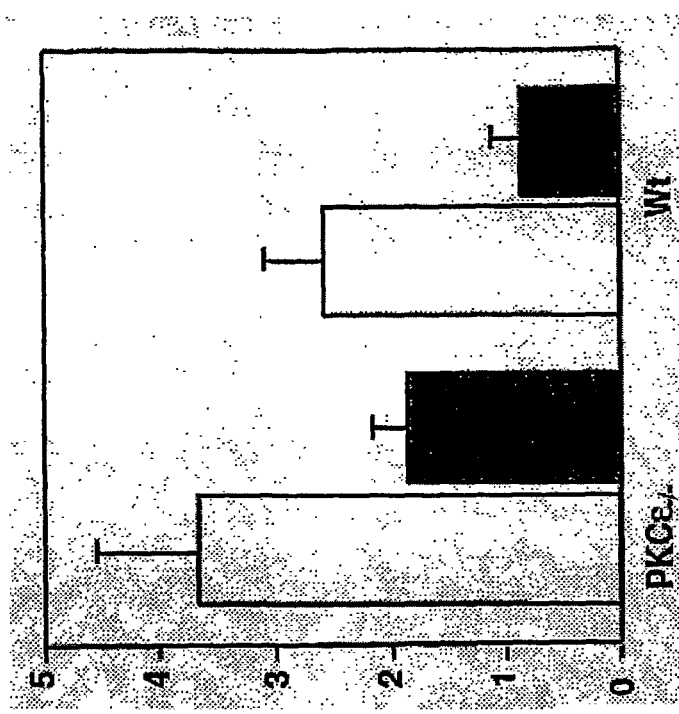
FIG. 8b is a graphical representation showing [14C]glucose clearance into lipid by white adipose tissue from mice treated as described in the legend to FIG. 8a. Filled bars represent mice fed the high-unsaturated fat diet. Open bars represent mice fed the chow diet. Results shown are means±SEM from 6-12 mice per group. ANOVA: P<0.002 for diet effect; P<0.03 for genotype effect.
Figure 8A:
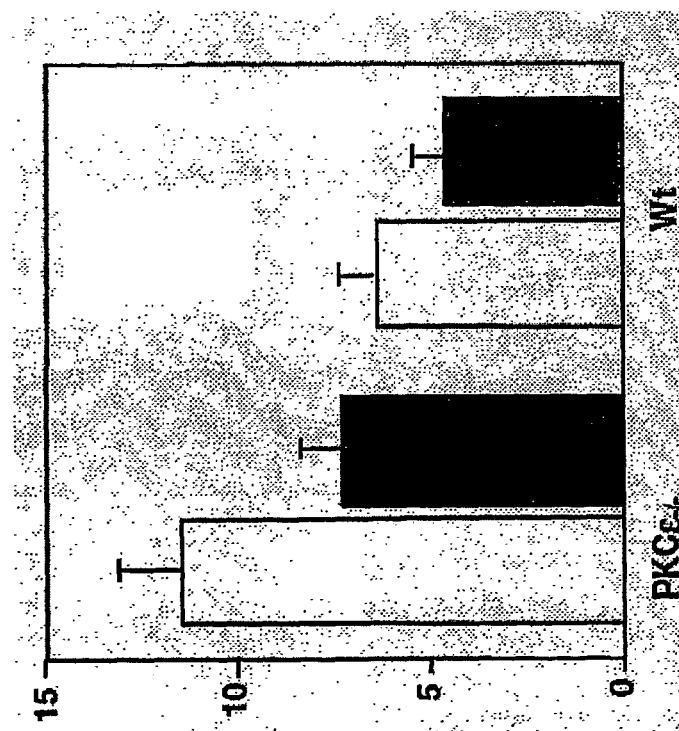
FIG. 8a is a graphical representation showing [3-$^3$H]2-deoxyglucose clearance during an intraperitoneal glucose tolerance test by white adipose tissue from wild type and PKCε$^{-/-}$ mice fed a high-unsaturated fat diet (filled bars), and age-matched wild type and PKCε$^{-/-}$ mice fed a standard chow diet (open bars). Results shown are means±SEM from 6-12 mice per group.
Figure 8D:
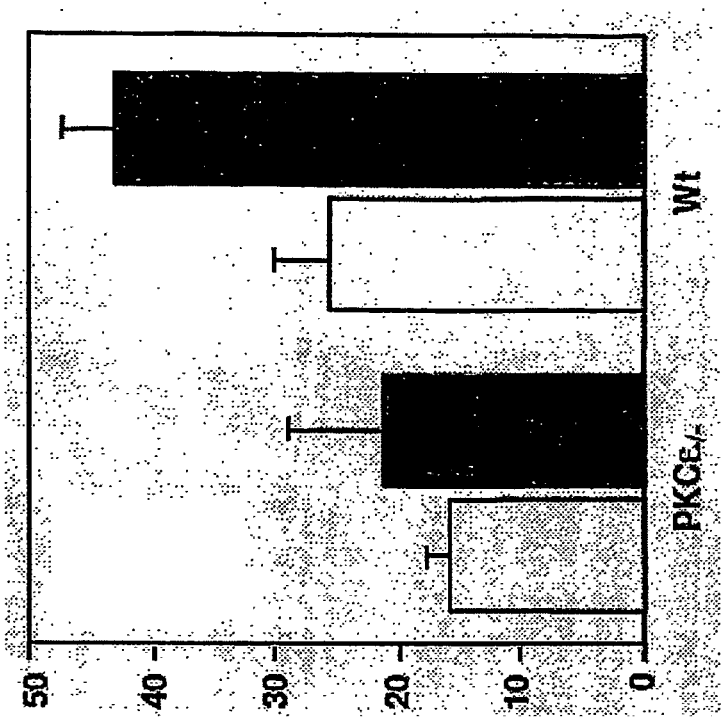
FIG. 8d is a graphical representation showing [14C]glucose clearance into glycogen by liver, from mice treated as described in the legend to FIG. 8a, Filled bars represent mice fed the high-unsaturated fat diet. Open bars represent mice fed the chow diet. Results shown are means±SEM from 6-12 mice per group. ANOVA: P<0.03 for genotype effect. Results shown are means±SEM from 6-12 mice per group.
Figure 8C:
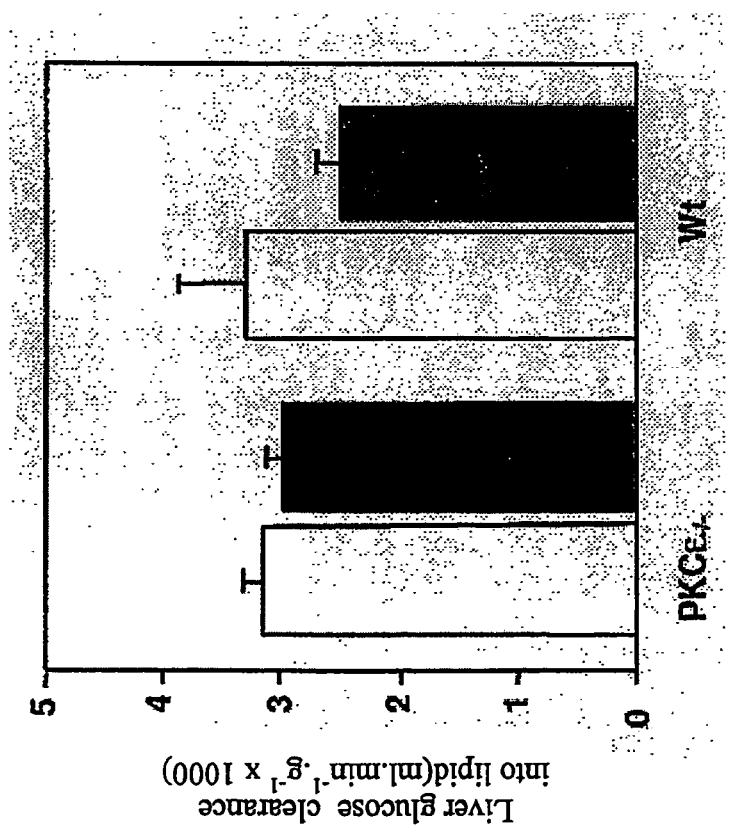
FIG. 8c is a graphical representation showing [14C]glucose clearance into lipid by liver from mice treated as described in the legend to FIG. 8a. Filled bars represent mice fed the high-unsaturated fat diet. Open bars represent mice fed the chow diet. Results shown are means±SEM from 6-12 mice per group. ANOVA: P<0.002 for diet effect; P<0.03 for genotype effect.

To determine whether these negative findings were dependent on the type of fat diet employed, the inventors carried out the same experiments using unsaturated fat-fed mice. This diet, however, did not give rise to significant differences in either whole body insulin tolerance or in sub-maximal insulin-stimulated glucose uptake by isolated soleus muscle (not shown). The inventors therefore re-investigated glucose disposal in these animals using radiolabeled glucose tracers to determine glucose clearance by selected tissues. In this manner the inventors now observed skeletal muscle insulin resistance during an insulin tolerance test in response to unsaturated fat-feeding, but this was again not reversed by PKCε deletion (FIG. 7*c*). In contrast, when the inventors measured glucose clearance by muscle during a glucose tolerance test, the inventors observed improved glucose uptake (FIG. 7*d*) and conversion into glycogen (FIG. 7*e*) by PKCε$^{-/-}$ mice compared to wild type mice, highly consistent with the improved blood glucose profiles observed under these conditions (FIG. 2*a*).

Taken in their entirety these data strongly suggest that the improved glucose tolerance displayed by fat-fed PKCε$^{-/-}$ mice is due to an enhanced availability of insulin in the peripheral circulation, rather than an increase in insulin sensitivity per se.

Consistent with that conclusion the inventors also observed similar effects of diet and genotype on glucose clearance by white adipose tissue but not liver (FIG. 3*a*-8*d*). The contribution of liver to whole body glucose clearance, however, was relatively low when compared to muscle, when the total mass of each tissue was taken into account.

Furthermore, while the inventors do not exclude an effect of PKCε deletion on hepatic glucose production in these animals, the inventors did not observe alterations in liver mRNA levels of the gluconeogenic enzymes phosphoenolpyruvate carboxykinase or fructose-1,6-bisphosphatase, or protein levels of fructose-1,6-bisphosphatase (not shown).

In addition, isolated hepatocytes from PKCε$^{-/-}$ mice, pretreated with unsaturated fatty acids and insulin, did not exhibit diminished glucose or glycogen production from lactate compared to cells from wild type mice (not shown).

Discussion

The inventors compared the effects of two dietary models of insulin resistance on wild type and PKCε$^{-/-}$ mice. This PKC isoform undergoes translocation, but not down regulation, in several models of chronic insulin resistance.

The inventors were unable to demonstrate any attenuation of insulin resistance by deletion of PKCε as determined by whole body tracer studies, measurements of insulin tolerance, or ex vivo analysis of glucose uptake in skeletal muscle. These negative results were explained neither by a failure of the diets to cause muscle insulin resistance or PKCε activation, nor by compensatory increases in expression of other PKC isoforms.

Although chow-fed PKCε$^{-/-}$ mice secrete similar amounts of C-peptide to wild type mice during a glucose tolerance test, they display considerably higher levels of circulating insulin under these conditions. Measurement of insulin uptake by isolated hepatocytes confirmed that PKCε deletion in these cells inhibits insulin internalisation. The approximately 30% inhibition observed in the rate of insulin uptake by PKCε$^{-/-}$ hepatocytes is likely to have a major influence on whole-body insulin clearance because of the direct circulatory link between pancreas and liver. Indeed, approximately 50% of secreted insulin is normally extracted by the liver during the first pass via the hepatic portal vein. The reduced clearance is therefore probably sufficient to explain the higher insulin levels of chow-fed PKCε$^{-/-}$ mice, both when fasted and during the glucose tolerance test.

Very little is known of the molecular mechanisms involved in regulating hepatic insulin clearance, although recent work suggests a role for the cell adhesion protein CAECAM-1 in mediating endocytosis of the IR. Insulin clearance is diminished in L-SACC1 transgenic mice, which overexpress a dominant negative form of CEACAM-1 in liver and L-SACC1 hepatocytes exhibit a greater than 50% reduction in insulin internalisation. However a direct interaction between PKCε and CEACAM-1 is unlikely since the defective insulin clearance of L-SACC1 mice is much more pronounced than that demonstrated here, and probably accounts for the increased body weight, secondary insulin resistance and altered fat metabolism displayed by those animals. Moreover CEACAM-1 appears to play an additional role in the regulation of insulin signaling through IRS-1 and Shc. The inventors did not, however, observe any defect in downstream signaling in hepatocytes from PKCε$^{-/-}$ mice, which is perhaps surprising given evidence that IR internalisation is implicated in the activation of MAPK following insulin binding. Presumably there is sufficient residual internalisation of IRs in PKCε$^{-/-}$ mice to maintain MAPK signaling.

The inventors did not observe PKCε co-precipitation with the IR in hepatocytes from wild type mice (not shown). It is therefore likely that PKCε modulates IR internalisation in the absence of a direct association. Because the inventors observed only partial inhibition of insulin internalisation in PKCε$^{-/-}$ mice, the role of this PKC isoform is most probably indirect, potentially mediated through alterations in cytoskeletal remodelling or vesicular trafficking, processes which are both known to be modulated by PKCε.

The second novel site of PKCε action described here is at the level of insulin secretion. This was most apparent using the saturated fat diet which induced defects in insulin and C-peptide secretion in wild type animals during the glucose tolerance test that were reminiscent of those seen in Type 2 diabetic subjects: an enhanced fasting secretion, which was barely increased in response to the glucose load. Deletion of PKCε lowered fasting C-peptide levels under these conditions, and facilitated a robust secretory response to glucose much greater than that seen in either chow-fed animals, or fat-fed wild type mice. The protection due to PKCε deletion appears to be mediated directly at the level of the β-cell since the analogous secretory defects, generated by chronic exposure of isolated islets to elevated fatty acids, were only observed in islets from wild type but not PKCε$^{-/-}$ mice.

The identification of PKC as a single molecular target in both development of elevated basal secretion, and loss of responsiveness to glucose, is unprecedented. This suggests that PKCε activation is involved at a very early stage in the sequence by which fatty acids exert their pleiotropic effects, and most probably regulates a cohort of genes whose altered expression potentially underlies the onset of secretory dysfunction. Down regulation of global PKC expression has previously been shown to modulate expression of some candidate genes in β-cells exposed to lipid. On the other hand the inventors results do not support a requirement for PKCε during glucose-stimulated secretion, as witnessed by the similar excursions in C-peptide levels seen in chow-fed wild type versus PKCε$^{-/-}$ mice during the glucose tolerance tests, and demonstrated more directly ex vivo using islets isolated from these animals. Although previous studies suggest PKCε may be activated during nutrient-stimulated insulin release, the inventors findings suggest that this activation is not essential for the secretory response. As with skeletal muscle insulin resistance, failure to observe a role for PKCε in glucose-stimulated secretion was not due to a compensatory up-regulation of other PKC isoforms in islets of the PKCε$^{-/-}$ mice (not shown).

The findings presented here have important implications for the treatment of Type 2 diabetes, since development of specific PKC inhibitors may exert beneficial (possibly synergistic) effects at the level of both liver and pancreas. Current therapeutics are targeted principally to separate tissues and act as muscle insulin sensitisers (thiazolidinediones), suppressors of hepatic glucose output (biguanides) or stimulators of insulin secretion (sulfonylureas). In particular the inventors results highlight a rationale for regulating hepatic insulin clearance as a therapy for insulin resistance and diabetes. In this regard it is probably fortuitous that PKCε appears to play a modulatory, rather than essential, role in IR internalisation, and that the 30% decrease in IR uptake that the inventors observed in hepatocytes of PKCε$^{-/-}$ mice is insufficient to alter IR signaling in liver. The inventors results also raise the novel possibility of therapeutic intervention at the level of the β-cell, not simply by directly stimulating insulin release, but by specifically counteracting the two major secretory defects observed in Type 2 diabetic subjects. Moreover, the inventors definition of novel pancreatic and hepatic sites of action of PKCε opens up new avenues for further investigating the contribution of these two tissues to the progression of Type 2 diabetes, and for elucidation of the underlying molecular events.

Example 6

Insulin Uptake and Signaling by Primary Cultured Hepatocytes

Methods
Isolation of Primary Hepatocytes.

The inventors infused livers firstly with 0.5 mM EDTA in Hank's solution (GibcoBRL), then with 80 µg/ml collagenase (Serva) and 4 mM $CaCl_2$ in EMEM (Trace). The inventors debrided livers into 40 µg/ml collagenase in L-15 medium, and digested further for 3-8 min. The inventors filtered the cells and washed 3 times with L-15 medium. Cells were finally resuspended in RPMI1640 medium (Gibco) containing 10% FCS (Trace Biosciences) and 50 µM 2-mercaptoethanol. The inventors seeded cells at $3 \times 10^5$ cells/well of a six-well tissue culture plate (Falcon).

Insulin Internalisation Assay.

Insulin was prepared by radiolabeling insulin (Roche) with $Na^{125}I$ by the Iodogen method (Pierce). The inventors cultured primary hepatocytes for 20 h after seeding, prior to insulin binding (30 pM) on ice for 4 h in serum-free RPMI/0.2% BSA. The inventors washed the cells in PBS/0.2% BSA then incubated them at 37° C. for 0-15 min in RPMI/0.2% BSA before washing in 0.2% BSA-PBS (pH 3) and PBS (pH 7.4) and lysing with 1 M KOH. The inventors counted the acid wash as surface-bound, non-internalised insulin and KOH-solubilised cells as internalised cell-associated ligand. The inventors calculated internalised insulin as percent cell-associated per specifically-bound ligand (the sum of surface-bound plus cell-associated ligand).

Analysis of Insulin Signaling.

The inventors cultured primary hepatocytes for 20 h prior to incubation in serum free RPMI 1640 for 6 h. The inventors stimulated cells with 10 nM insulin and immunoblotted lysates for phosphorylated and total levels of insulin signaling components.

Statistical Analysis.

The inventors analysed results by Student's t-test or ANOVA using Statview 4.5 for Macintosh (Abacus Concepts). Results are expressed±standard error, and differences were considered to be statistically significant at P<0.05.

Results

Figure 9:
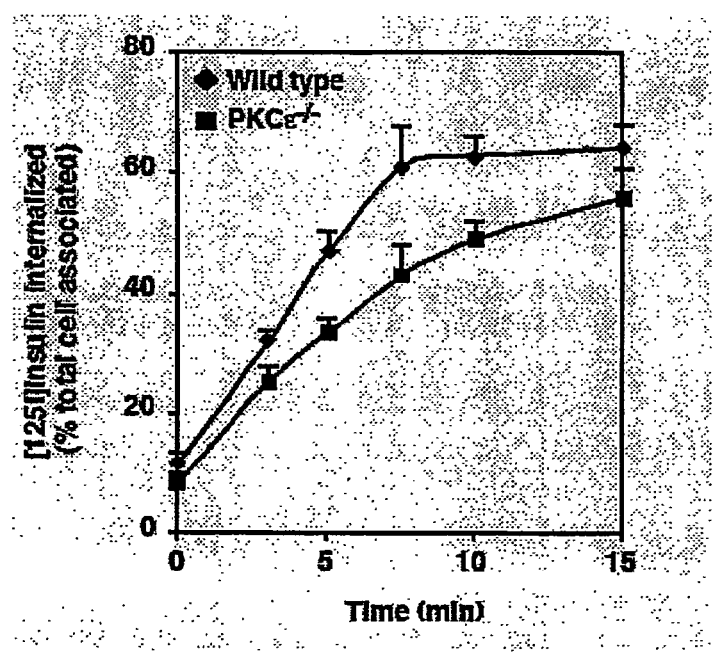
FIG. 9 is a graphical representation showing [$^{125}$I]insulin uptake by isolated primary hepatocytes from wild type (♦) and PKCε$^{-/-}$ (■) mice (n=8). ANOVA: P<0.001 for effect of genotype. Insulin uptake is measured as a percentage of total cell associated insulin (i.e., membrane-bound and internalized). The rate of insulin uptake into primary hepatocytes was shown to be lower (about 0.4×-0.6×) for PKCε null mutant mice than for wild-type mice expressing a functional PKCε allele, confirming the reduced insulin clearance when PKCε is inactivated or reduced. Insulin uptake into primary hepatocytes under these conditions was approximately linear for at least about 5 mins.
Figure 11B:
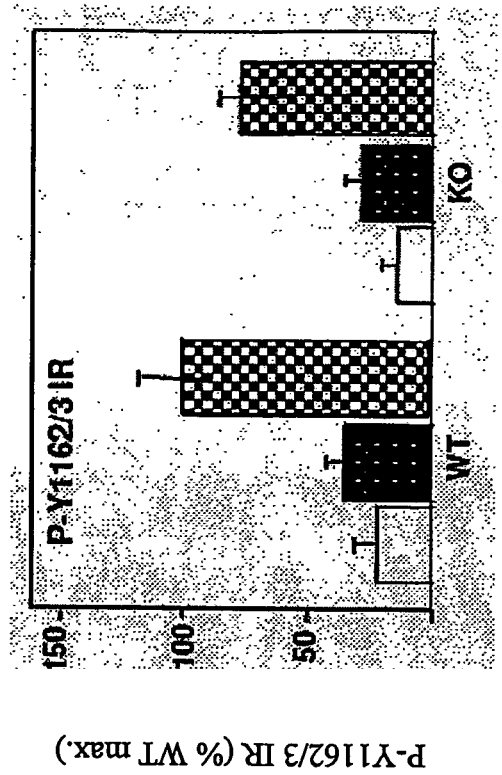
FIG. 11b is a graphical representation showing quantification of tyrosine phosphorylation of the insulin receptor (P-Y1162/3 IR) in primary hepatocytes from FIG. 10b following insulin stimulation. The immunoblot shown in row 1 of FIG. 10b was subjected to densitometry, and data corrected for total protein loading. Data show no inability of the insulin receptor from PKCε$^{-/-}$ mice (KO) to be phosphorylated in response to insulin compared to wild-type (WT) mice. ANOVA: P<0.001 for effect of insulin.
Figure 11A:
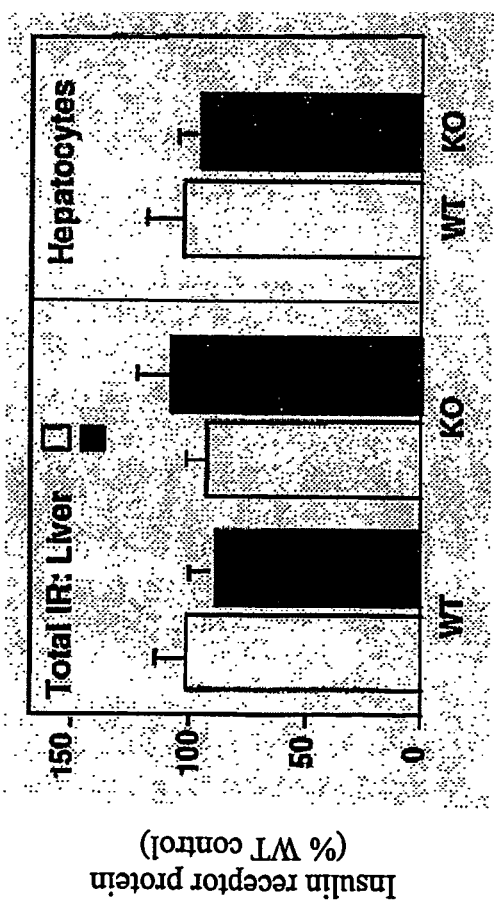
FIG. 11a is a graphical representation showing quantification of data on insulin receptor (IR) levels in liver and hepatocytes from FIG. 10a. The immunoblot shown in FIG. 10a was subjected to densitometry, and data corrected for total protein loading. Data show no significant differences in IR levels between wild-type (WT) and PKCε$^{-/-}$ (KO) mice receiving a chow diet (open bars) or a diet high in unsaturated fats (filled bars), or between primary hepatocytes of PKCε$^{-/-}$ mice fed and wild-type mice fed a chow diet.

Because of the surprising indications that specific alterations in liver and pancreatic β-cells, rather than skeletal muscle, appeared to account for the improved glucose tolerance seen in PKCε$^{-/-}$ mice, the inventors therefore examined these tissues in more detail. Firstly the inventors measured insulin internalisation by primary hepatocytes and observed a 30% reduction in the initial rate of insulin uptake by cells from PKCε$^{-/-}$ versus wild type mice (FIG. 9). These differences could not be explained by alterations in insulin receptor (IR) levels, measured either in liver extracts or in lysates from primary cultured hepatocytes (FIGS. 10a and 11a). In addition, the inventors found no change in the affinity of the IR for insulin measured by insulin binding to intact hepatocytes at 4° C. (insulin IC$_{50}$=1.23±0.3 nM (wild type) and 1.33±0.3 nM (PKCε$^{-/-}$) in 3 experiments). Furthermore, the inventors also found no significant difference between wild type and PKCε$^{-/-}$ cells in the activation of insulin signaling components over a range of insulin doses and time points (FIG. 10b and FIGS. 11b-11d).

These data suggest that while reduced insulin uptake by PKCε$^{-/-}$ hepatocytes could explain the elevated insulin levels of chow-fed PKCε$^{-/-}$ mice, the this was not accompanied by diminished insulin signaling.

Data presented in FIG. 9 also indicate that insulin uptake into primary hepatocytes was approximately linear for at least about 5-7.5 mins.

Example 7

Insulin Secretion in Isolated Pancreatic Islets

Methods
Measurement of Glucose-Stimulated Insulin Secretion in Pancreatic Islets.

The inventors isolated mouse islets by ductal perfusion of pancreata with collagenase and separation on a Ficoll gradient. The inventors cultured islets for 48 h in RPMI 1640 supplemented with either BSA alone or BSA coupled to palmitate. The inventors picked islets in groups of 15 for batch incubations, firstly preincubating them for 30 min in 2.8 mM glucose KRB, and then in KRB containing 2.8 mM or 16.7 mM glucose for 1 h. The inventors then determined insulin secreted into the KRB by RIA (Linco).

Statistical Analysis.

The inventors analysed results by Student's t-test or ANOVA using Statview 4.5 for Macintosh (Abacus Concepts). Results are expressed±standard error, and differences were considered to be statistically significant at P<0.05.

Results

Because the additional elevation of serum insulin levels observed in fat-fed PKCε$^{-/-}$ mice correlated with increased C-peptide concentrations, it was likely that this involved enhanced insulin secretion from pancreatic β-cells. To investigate this further, the inventors examined glucose-stimulated insulin secretion from pancreatic islets, isolated from wild type and PKCε$^{-/-}$ mice and then cultured for 48 h in absence or presence of the saturated fatty acid palmitate. As well-documented, chronic exposure of wild type islets to fatty acid resulted in both an enhanced basal secretion and a diminished response to high glucose, such that a statistically significant difference between the two acute treatment conditions was no longer observed (FIG. 12). In contrast, glucose-stimulated insulin secretion was essentially normal in palmitate-cultured islets isolated from PKCε$^{-/-}$ mice. These in vitro results are entirely consistent with the C-peptide data from mice fed the saturated fat diet, in which deletion of PKCε resulted in a decrease in fasting levels, and enhanced response during the glucose tolerance test (FIG. 6d). The data from isolated hepatocytes and islets (FIGS. 9 and 12) therefore confirm that loss of PKCε activity exerts two distinct effects on liver and pancreas which, together, enhance insulin levels in the peripheral circulation and thus help maintain glucose tolerance.

Example 8

Inhibition of PKCε in Pancreatic β-Islet Cells by Expression of the Dominant Negative Mutant PKCε K437R MIN6 cells were passaged in 75 cm$^2$ flasks with 20 ml of DMEM containing 25 mM glucose, 24 mM NaHCO$_3$, 10 mM Hepes, 10% (v/v) fetal calf serum, 50 IU/ml penicillin and 50 μg/ml streptomycin. Cells were seeded at 3×10$^5$/well in 0.5 ml in a 24 well dish for secretory experiments. At 48 h prior to the experiment (24 h after seeding), the medium was replaced with DMEM (as above but with 6 mM glucose) and supplemented with either bovine serum albumin (BSA) alone or BSA coupled to palmitate or oleate. Included in this medium was 100 plaque-forming units recombinant adenovirus expressing either green fluorescent protein alone (control) or green fluorescent protein as well as either PKCε wild-type (SEQ ID NO: 2 or 4) or a kinase-dead PKCε (SEQ ID NO: 15). The latter was generated by the K437R mutation in the ATP-binding site of PKCε. All recombinant adenovirus were generated using the pAdEasy system.

For FA coupling, 18.4% BSA was dissolved in DMEM (25 mM glucose) by gentle agitation at room temperature for 3 h. Palmitate or oleate (8 mM) were then added as Na$^+$ salts, and the mixture agitated overnight at 37° C. The pH was then adjusted to 7.4, and after sterile filtering. FA concentrations were verified using a commercial kit and aliquots were stored at −20° C.

Similar couplings were made using glucose-free modified Krebs-Ringer bicarbonate (KRB) buffer containing 5 mM NaHCO$_3$, 1 mM CaCl$_2$, 0.5% (w/v) BSA, and 10 mM Hepes (pH 7.4) instead of DMEM.

This procedure generated BSA-coupled FA in molar ratio of 3:1 (generally 0.4 mM:0.92% BSA final).

Cultured cells were washed once in modified KRB buffer containing 2.8 mM glucose, and then preincubated for a further 30 min in 0.5 ml of the same medium at 37° C. This was then replaced with 0.5 ml of prewarmed KRB containing other additions as indicated, for a further 60 min at 37° C. An aliquot was then removed for analysis of insulin content by radioimmunoassay. The cell monolayers were washed twice in PBS, and then extracted for measurement of total insulin content by lysis in 0.5 ml H₂O/well followed by sonication.

Results axe confirmed in whole animals expressing the K437R mutant in the islet cells, in a variety of genetic backgrounds. Transgenic animals expressing the K437R mutant are produced as described herein above, using the insulin or pdx-1 promoter to confer islet-cell expression, and introduced into a variety of diabetic model backgrounds as described in Examples 1-4.

Example 9

Inhibition of PKCε by Peptide Antagonists

The peptide EAVSLKPT (εV1-2) (SEQ ID NO: 7) corresponding to residues in the variable region of PKC is conjugated to the penetratin heptapeptide to form the bioactive peptide RRMKWKKEAVSLKPT for delivery to intact cells e.g., in screening assays or for treatment.

Another inhibitory peptide that the inventors have employed is that corresponding to pseudo substrate region (149-164) of PKCε namely ERMRPRKRQGAVRRRV (SEQ ID NO: 13) which was myristolylated at the N-terminus to facilitate cell entry (myrPSPε).

For determining liver-specific effects the human hepatoma cell line Huh7, or primary mouse or rat hepatocytes is used. Control cells and those preheated with PKCε inhibitory peptides are stimulated with insulin or an analogue thereof and activity of the insulin receptor monitored.

For β-cell effects the murine cell line MIN6, or isolated mouse or rat pancreatic islets, are used. Experiments are conducted using cells pretreated with 0.4 mM oleate coupled to BSA, or BSA alone as negative control. The chronic effect of the PKC inhibitory peptides to overcome the ablation of glucose-stimulated insulin secretion due to oleate pre-treatment is determined.

Example 10

Effects of Conditional Knockout of PKCε Expression

Reduced PKCε expression in the liver and/or pancreatic islet cells in one or more of the lines produced as described in Examples 1-4 restores insulin sensitivity and protects pancreatic β-islet cells against the effects of a high fat diet.

We claim:

1. A method of treatment of an abnormality of glucose metabolism in an animal subject in need of treatment thereof comprising administering to the subject an amount of an antagonist of a protein kinase C epsilon (PKCE) to reduce the level and/or activity of the enzyme in the liver of the subject thereby reducing insulin clearance by the liver or administering said antagonist to enhance insulin secretion by the pancreas.

2. The method of claim 1 wherein the subject is a human in need of treatment thereof.

3. The method of claim 2 wherein the subject suffers from a condition selected from the group consisting of Type 2 diabetes, hyperglycaemia, hyperinsulinemia, insulin resistance, glucose intolerance and combinations thereof.

4. The method according to claim 1 wherein the antagonist comprises nucleic acid comprising a nucleotide sequence selected from the group consisting of SEQ ID Nos: 16-27 and mixtures thereof.

5. The method of claim 4 wherein the antagonist is targeted to the liver of the subject.

6. The method of claim 5 wherein targeting is achieved by expressing the antagonist in an expression vector capable of binding to a receptor on a liver cell that mediates endocytosis of the vector.

7. The method of claim 6 wherein the expression vector is a replication-defective hepadnavirus or an adenovirus vector.

8. The method of claim 6 wherein the antagonist is expressed in a liver cell operably under the control of a promoter selected from the group consisting of human phenylalanine hydroxylase gene promoter, transthyretin promoter, serum albumin gene promoter, cytochrome P450 2B gene promoter, apolipoprotein A-1 gene promoter, phosphoenolpyruvate carboxykinase gene promoter, ornithine transcarbamylase gene promoter, UDP-glucuronosyltransferase gene promoter and hepatocyte nuclear factor 4 gene promoter.

9. The method of claim 1 wherein the antagonist comprises a peptide.

10. The method of claim 1 wherein the antagonist is a peptide.

11. The method according to claim 9 wherein the antagonist comprises a peptide comprising a sequence SEQ ID NO: 7.

12. The method of claim 9 wherein the antagonist comprises one or more peptides comprising a sequence set forth in SEQ ID NO: 7 conjugated to a targeting moiety set forth in SEQ ID NO:13 for delivery to intact cells.

13. A method of treatment of an abnormality of glucose metabolism in a human subject comprising administering to the subject an amount of an antagonist of a protein kinase C epsilon (PKCE) comprising a peptide comprising a sequence set forth in SEQ ID NO: 7 to reduce the level and/or activity of the enzyme in the liver of the subject thereby reducing insulin clearance by the liver or administering said antagonist to enhance insulin secretion by the pancreas.

14. A method of treating type II diabetes in a human subject comprising administering to the subject an amount of an antagonist of a protein kinase C epsilon (PKCE) comprising a peptide comprising a sequence set forth in SEQ ID NO: 7 to reduce the level and/or activity of the enzyme in the liver of the subject thereby reducing insulin clearance by the liver or administering said antagonist to enhance insulin secretion by the pancreas.

15. A method of treatment of an abnormality of glucose metabolism in a human subject comprising administering to the subject an amount of an antagonist of a protein kinase C epsilon (PKCE) comprising a peptide comprising a sequence set forth in SEQ ID NO: 7 conjugated to a targeting moiety set forth in SEQ ID NO:13 for delivery to intact cells to reduce the level and/or activity of the enzyme in the liver of the subject thereby reducing insulin clearance by the liver or administering said antagonist to enhance insulin secretion by the pancreas.

16. A method of treatment of an abnormality of glucose metabolism in a human subject comprising administering to the subject an amount of an antagonist of a protein kinase C epsilon (PKCE) comprising a peptide comprising a sequence set forth in SEQ ID NO: 7 conjugated to a targeting moiety set forth in SEQ ID NO:13 for delivery to intact cells to enhance insulin secretion by the pancreas.

17. A method of treating type II diabetes in a human subject comprising administering to the subject an amount of an antagonist of a protein kinase C epsilon (PKCE) comprising a peptide comprising a sequence set forth in SEQ ID NO: 7 conjugated to a targeting moiety set forth in SEQ ID NO:13 for delivery to intact cells for a time and under conditions sufficient to reduce the level and/or activity of the enzyme in the liver of the subject thereby reducing insulin clearance by the liver or administering said antagonist for a time and under conditions sufficient to enhance insulin secretion by the pancreas.

18. A method of treating type II diabetes in a human subject comprising administering to the subject an amount of an antagonist of a protein kinase C epsilon (PKCE) comprising a peptide comprising a sequence set forth in SEQ ID NO: 7 conjugated to a targeting moiety set forth in SEQ ID NO:13 for delivery to intact cells to enhance insulin secretion by the pancreas.

19. The method according to claim 9 wherein the antagonist comprises a polypeptide comprising a sequence set forth in SEQ ID NO: 7.

20. The method of claim 9 wherein the polypeptide is myristoylated at the N-terminus to facilitate cell entry.

21. The method of claim 1, wherein the abnormality of glucose metabolism is type II diabetes in a human subject.

22. The method of claim 21, wherein the antagonist of a protein kinase C epsilon (PKCε) comprises a peptide comprising a sequence set forth in SEQ ID NO: 7.

23. The method of claim 22 wherein the antagonist of a protein kinase C epsilon (PKCE) comprises a peptide comprising a sequence set forth in SEQ ID NO: 7 conjugated to a targeting moiety set forth in SEQ ID NO:13 for delivery to intact cells.

24. The method of claim 19 wherein the antagonist additionally comprises a targeting moiety set forth in SEQ ID NO:13 for delivery to intact cells conjugated to the peptide.

25. The method of claim 2 wherein the subject suffers from type 2 diabetes.

26. The method of claim 11, wherein the antagonist is administered at a dose of 1 µg/kg body weight to about 100 mg/kg of body weight of the subject.

27. The method of claim 1 comprising administering to the subject an amount of the antagonist of PKCE to enhance insulin secretion by the pancreas.

28. The method of claim 1 comprising administering to the subject an amount of the antagonist of PKCE to reduce the level and/or activity of the enzyme in the liver of the subject thereby reducing insulin clearance by the liver.

* * * * *

SEQUENCE LISTING

```
<160> NUMBER OF SEQ ID NOS: 27

<210> SEQ ID NO 1
<211> LENGTH: 2235
<212> TYPE: DNA
<213> ORGANISM: Mus musculus

<400> SEQUENCE: 1
gaattcacca tggtagtgtt caatggcctt cttaagatca aaatctgcga ggcggtgagc      60
ttgaagccca cagcctggtc gctgcgccat gcggtgggac cccggccaca gacgttcctt    120
ttggacccct acattgccct taacgtggac gactcgcgca tcggccaaac agccaccaag    180
caaaagacca cagcccggc ctggcacgat gagttcgtca ccgatgtgtg caatgggcgc     240
aagatcgagc tggctgtctt tcacgacgct cctatcggct acgacgactt cgtggccaac    300
tgcaccatcc agttcgagga gctgctgcag aatgggagcc gtcacttcga ggactggatt    360
gacctggagc cagaaggaaa agtgtacgtg atcatcgatc tctcgggatc atcgggtgaa    420
gcccctaaag acaatgaaga acgagtgttc agggagcgta tgcggccaag gaagcggcaa    480
ggggctgtca ggcgcagggt ccaccaggtc aatgccaca agttcatggc cacctacttg     540
cggcaaccca cctactgctc ccactgcaga gatttcatct ggggtgtcat aggaaaacag    600
ggatatcaat gtcaagtttg cacttgcgtt gtccacaagc gatgtcatga gctcattatt    660
acaaagtgcg ctgggctgaa gaaacaggaa acccctgacg aggtgggctc ccaacggttc    720
agcgtcaaca tgccccacaa gttcgggatc cacaactaca aggtccccac gttctgtgac    780
cactgtgggt ccctgctctg gggcctcttg cggcagggct tgcagtgtaa agtctgcaaa    840
atgaatgttc accggcgatg tgagaccaat gtggctccca actgtggggt agacgccaga    900
ggaattgcca aagtgctggc tgaccttggt gttactccag acaaaatcac caacagtggc    960
caaaggagga aaaagctcgc tgctggtgct gagtccccac agccggcttc tggaaactcc    1020
ccatctgaag acgaccgatc caagtcagcg cccacctccc cttgtgacca ggaactaaaa   1080
gaacttgaaa acaacattcg gaaggccttg tcatttgaca accgaggaga ggagcaccga   1140
```

```
gcgtcgtcgg ccaccgatgg ccagctggca agccccggag agaacgggga agtccggcca    1200
ggccaggcca agcgcttggg gctggatgag ttcaacttca tcaaggtgtt gggcaaaggc    1260
agctttggca aggtcatgtt ggcggaactc aaaggcaaag atgaagtcta cgctgtgaag    1320
gtcttgaaga aggacgttat cctacaagac gatgatgtgg actgcacaat gacagagaag    1380
aggattttgg ctctggctcg gaaacaccct tatctaaccc aactctattg ctgcttccag    1440
accaaggacc gcctcttctt cgtcatggaa tatgtaaatg gtggagacct catgttccag    1500
attcagcggt cccgaaaatt tgatgagcct cgttctcggt tctatgccgc agaggtcaca    1560
tcagccctca tgtttctcca ccagcacgga gtgatctaca gggatttgaa actggacaac    1620
atccttctag atgcagaagg ccactgcaag ctggctgact ttgggatgtg caaggaaggg    1680
attatgaatg gtgtgacaac taccaccttc tgtgggactc ctgactacat agctccagag    1740
atcctacagg agttggagta cggcccctca gtggactggt gggccctggg ggtgctgatg    1800
tacgagatga tggctgggca gccccccttt gaagctgaca cgaggacga cttgttcgaa    1860 tccatccttc atgatgatgt ctctctatcct gtctggctta gcaaggaagc tgtcagcatc    1920
ctgaaagctt tcatgaccaa gaacccgcac aagcgcctgg gctgtgtggc agcgcagaac    1980
ggggaggacg ccatcaagca acatccattc ttcaaggaga ttgactgggt actgctggag    2040
cagaagaaaa tcaagccccc cttcaagccg agaattaaaa ccaaaagaga tgtcaataac    2100
tttgaccaag actttacgcg ggaagagcca atacttacac ttgtggatga agcaatcatt    2160
aagcagatca accaggaaga atttaaaggc ttctcctact tggtgaaga cctgatgccc    2220 tgagaaactg aattc                                                     2235
```

<210> SEQ ID NO 2
<211> LENGTH: 737
<212> TYPE: PRT
<213> ORGANISM: Mus musculus

<400> SEQUENCE: 2

```
Met Val Val Phe Asn Gly Leu Leu Lys Ile Lys Ile Cys Glu Ala Val
1               5                   10                  15

Ser Leu Lys Pro Thr Ala Trp Ser Leu Arg His Ala Val Gly Pro Arg
            20                  25                  30

Pro Gln Thr Phe Leu Leu Asp Pro Tyr Ile Ala Leu Asn Val Asp Asp
        35                  40                  45

Ser Arg Ile Gly Gln Thr Ala Thr Lys Gln Lys Thr Asn Ser Pro Ala
    50                  55                  60

Trp His Asp Glu Phe Val Thr Asp Val Cys Asn Gly Arg Lys Ile Glu
65                  70                  75                  80

Leu Ala Val Phe His Asp Ala Pro Ile Gly Tyr Asp Asp Phe Val Ala
                85                  90                  95

Asn Cys Thr Ile Gln Phe Glu Glu Leu Leu Gln Asn Gly Ser Arg His
            100                 105                 110

Phe Glu Asp Trp Ile Asp Leu Glu Pro Glu Gly Lys Val Tyr Val Ile
        115                 120                 125

Ile Asp Leu Ser Gly Ser Ser Gly Glu Ala Pro Lys Asp Asn Glu Glu
    130                 135                 140

Arg Val Phe Arg Glu Arg Met Arg Pro Arg Lys Arg Gln Gly Ala Val
145                 150                 155                 160

Arg Arg Arg Val His Gln Val Asn Gly His Lys Phe Met Ala Thr Tyr
                165                 170                 175
```

```
                                    -continued

Leu Arg Gln Pro Thr Tyr Cys Ser His Cys Arg Asp Phe Ile Trp Gly
        180                 185                 190

Val Ile Gly Lys Gln Gly Tyr Gln Cys Gln Val Cys Thr Cys Val Val
    195                 200                 205

His Lys Arg Cys His Glu Leu Ile Ile Thr Lys Cys Ala Gly Leu Lys
210                 215                 220

Lys Gln Glu Thr Pro Asp Glu Val Gly Ser Gln Arg Phe Ser Val Asn
225                 230                 235                 240

Met Pro His Lys Phe Gly Ile His Asn Tyr Lys Val Pro Thr Phe Cys
                245                 250                 255

Asp His Cys Gly Ser Leu Leu Trp Gly Leu Arg Gln Gly Leu Gln
                260                 265                 270

Cys Lys Val Cys Lys Met Asn Val His Arg Arg Cys Glu Thr Asn Val
            275                 280                 285

Ala Pro Asn Cys Gly Val Asp Ala Arg Gly Ile Ala Lys Val Leu Ala
        290                 295                 300

Asp Leu Gly Val Thr Pro Asp Lys Ile Thr Asn Ser Gly Gln Arg Arg
305                 310                 315                 320

Lys Lys Leu Ala Ala Gly Ala Glu Ser Pro Gln Pro Ala Ser Gly Asn
                325                 330                 335

Ser Pro Ser Glu Asp Asp Arg Ser Lys Ser Ala Pro Thr Ser Pro Cys
            340                 345                 350

Asp Gln Glu Leu Lys Glu Leu Glu Asn Asn Ile Arg Lys Ala Leu Ser
        355                 360                 365

Phe Asp Asn Arg Gly Glu Glu His Arg Ala Ser Ser Ala Thr Asp Gly
    370                 375                 380

Gln Leu Ala Ser Pro Gly Glu Asn Gly Glu Val Arg Pro Gly Gln Ala
385                 390                 395                 400

Lys Arg Leu Gly Leu Asp Glu Phe Asn Phe Ile Lys Val Leu Gly Lys
                405                 410                 415

Gly Ser Phe Gly Lys Val Met Leu Ala Glu Leu Lys Gly Lys Asp Glu
            420                 425                 430

Val Tyr Ala Val Lys Val Leu Lys Lys Asp Val Ile Leu Gln Asp Asp
        435                 440                 445

Asp Val Asp Cys Thr Met Thr Glu Lys Arg Ile Leu Ala Leu Ala Arg
    450                 455                 460

Lys His Pro Tyr Leu Thr Gln Leu Tyr Cys Cys Phe Gln Thr Lys Asp
465                 470                 475                 480

Arg Leu Phe Phe Val Met Glu Tyr Val Asn Gly Gly Asp Leu Met Phe
                485                 490                 495

Gln Ile Gln Arg Ser Arg Lys Phe Asp Glu Pro Arg Ser Arg Phe Tyr
            500                 505                 510

Ala Ala Glu Val Thr Ser Ala Leu Met Phe Leu His Gln His Gly Val
        515                 520                 525

Ile Tyr Arg Asp Leu Lys Leu Asp Asn Ile Leu Leu Asp Ala Glu Gly
    530                 535                 540

His Cys Lys Leu Ala Asp Phe Gly Met Cys Lys Glu Gly Ile Met Asn
545                 550                 555                 560

Gly Val Thr Thr Thr Thr Phe Cys Gly Thr Pro Asp Tyr Ile Ala Pro
                565                 570                 575

Glu Ile Leu Gln Glu Leu Glu Tyr Gly Pro Ser Val Asp Trp Trp Ala
            580                 585                 590

Leu Gly Val Leu Met Tyr Glu Met Met Ala Gly Gln Pro Pro Phe Glu
        595                 600                 605
```

```
Ala Asp Asn Glu Asp Asp Leu Phe Glu Ser Ile Leu His Asp Val
    610                 615                 620

Leu Tyr Pro Val Trp Leu Ser Lys Glu Ala Val Ser Ile Leu Lys Ala
625                 630                 635                 640

Phe Met Thr Lys Asn Pro His Lys Arg Leu Gly Cys Val Ala Ala Gln
                645                 650                 655

Asn Gly Glu Asp Ala Ile Lys Gln His Pro Phe Phe Lys Glu Ile Asp
            660                 665                 670

Trp Val Leu Leu Glu Gln Lys Lys Ile Lys Pro Pro Phe Lys Pro Arg
        675                 680                 685

Ile Lys Thr Lys Arg Asp Val Asn Asn Phe Asp Gln Asp Phe Thr Arg
690                 695                 700

Glu Glu Pro Ile Leu Thr Leu Val Asp Glu Ala Ile Ile Lys Gln Ile
705                 710                 715                 720

Asn Gln Glu Glu Phe Lys Gly Phe Ser Tyr Phe Gly Glu Asp Leu Met
                725                 730                 735

Pro

<210> SEQ ID NO 3
<211> LENGTH: 2244
<212> TYPE: DNA
<213> ORGANISM: Homo sapiens

<400> SEQUENCE: 3
ctccccgccc cgaccatggt agtgttcaat ggccttctta agatcaaaat ctgcgaggcc      60
gtgagcttga agcccacagc ctggtcgctg cgccatgcgg tgggaccccg ccgcagact     120
ttccttctcg accctacat tgccctcaat gtggacgact cgcgcatcgg ccaaacggcc     180
accaagcaga agaccaacag cccggcctgg cacgacgagt tcgtcaccga tgtgtgcaac     240
ggacgcaaga tcgagctggc tgtctttcac gatgccccca taggctacga cgacttcgtg     300
gccaactgca ccatccagtt tgaggagctg ctgcagaacg ggagccgcca cttcgaggac     360
tggattgatc tggagccaga aggaagagtg tatgtgatca tcgatctctc agggtcgtcg     420
ggtgaagccc ctaaagacaa tgaagagcgt gtgttcaggg aacgcatgcg gccgaggaag     480
cggcagggg ccgtcaggcg cagggtccat caggtcaacg ccacaagtt catggccacc     540
tatcttcggc agcccaccta ctgctcccat gcagagact tcatctgggg tgtcatagga     600
aagcagggat accagtgtca agtctgcacc tgcgtggtcc acaagcggtg ccacgagctc     660
ataatcacaa agtgtgctgg gttaaagaag caggagaccc ccgaccaggt gggctcccag     720
cggttcagcg tcaacatgcc ccacaagttc ggtatccaca actacaaggt ccctaccttc     780
tgcgatcact gtgggtccct gctctgggga ctcttgcggc agggtttgca gtgtaaagtc     840
tgcaaaatga atgttcaccg tcgatgtgag accaacgtgg ctcccaactg tggagtggat     900
gccagaggaa tcgccaaagt actggccgac ctgggcgtta cccagacaa aatcaccaac     960
agcggccaga gaaggaaaaa gctcattgct ggtgccgagt ccccgcagcc tgcttctgga    1020
agctcaccat ctgaggaaga tcgatccaag tcagcaccca cctcccttg tgaccaggaa    1080
ataaaagaac ttgagaacaa cattcggaaa gccttgtcat ttgacaaccg aggagaggag    1140
caccgggcag catcgtctcc tgatggccag ctgatgagcc ccgtgagaa tggcgaagtc    1200
cggcaaggcc aggccaagcg cctgggcctg atgagttca acttcatcaa ggtgttgggc    1260
aaaggcagct ttggcaaggt catgttggca gaactcaagg gcaaagatga agtatatgct    1320
gtgaaggtct taaagaagga cgtcatcctt caggatgatg acgtggactg cacaatgaca    1380
```

```
gagaagagga ttttggctct ggcacggaaa cacccgtacc ttacccaact ctactgctgc   1440
ttccagacca aggaccgcct cttttttcgtc atggaatatg taaatggtgg agacctcatg   1500
tttcagattc agcgctcccg aaaattcgac gagcctcgtt cacggttcta tgctgcagag   1560
gtcacatcgg ccctcatgtt cctccatcag catggagtca tctacaggga tttgaaactg   1620
gacaacatcc ttctggatgc agaaggtcac tgcaagctgg ctgacttcgg gatgtgcaag   1680
gaagggattc tgaatggtgt gacgaccacc acgttctgtg ggactcctga ctacatagct   1740
cctgagatcc tgcaggagtt ggagtatggc ccctccgtgg actggtgggc ctgggggtg   1800 ctgatgtacg agatgatggc tggacagcct cccttttgagg ccgacaatga ggacgaccta   1860
tttgagtcca tcctccatga cgacgtgctg tacccagtct ggctcagcaa ggaggctgtc   1920
agcatcttga aagctttcat gacgaagaat ccccacaagc gcctgggctg tgtggcatcg   1980
cagaatggcg aggacgccat caagcagcac ccattcttca agagattga ctgggtgctc   2040 ctggagcaga agaagatcaa gccacccttc aaaccacgca ttaaaaccaa agagacgtc   2100 aataattttg accaagactt tacccgggaa gagccggtac tcacccttgt ggacgaagca   2160
attgtaaagc agatcaacca ggaggaattc aaaggttttct cctactttgg tgaagacctg   2220
atgccctgag agcccactgc agtt                                          2244

<210> SEQ ID NO 4
<211> LENGTH: 737
<212> TYPE: PRT
<213> ORGANISM: Homo sapiens

<400> SEQUENCE: 4

Met Val Val Phe Asn Gly Leu Leu Lys Ile Lys Ile Cys Glu Ala Val
1               5                   10                  15

Ser Leu Lys Pro Thr Ala Trp Ser Leu Arg His Ala Val Gly Pro Arg
            20                  25                  30

Pro Gln Thr Phe Leu Leu Asp Pro Tyr Ile Ala Leu Asn Val Asp Asp
        35                  40                  45

Ser Arg Ile Gly Gln Thr Ala Thr Lys Gln Lys Thr Asn Ser Pro Ala
    50                  55                  60

Trp His Asp Glu Phe Val Thr Asp Val Cys Asn Gly Arg Lys Ile Glu
65                  70                  75                  80

Leu Ala Val Phe His Asp Ala Pro Ile Gly Tyr Asp Asp Phe Val Ala
                85                  90                  95

Asn Cys Thr Ile Gln Phe Glu Glu Leu Leu Gln Asn Gly Ser Arg His
            100                 105                 110

Phe Glu Asp Trp Ile Asp Leu Glu Pro Glu Gly Arg Val Tyr Val Ile
        115                 120                 125

Ile Asp Leu Ser Gly Ser Ser Gly Glu Ala Pro Lys Asp Asn Glu Glu
    130                 135                 140

Arg Val Phe Arg Glu Arg Met Arg Pro Arg Lys Arg Gln Gly Ala Val
145                 150                 155                 160

Arg Arg Arg Val His Gln Val Asn Gly His Lys Phe Met Ala Thr Tyr
                165                 170                 175

Leu Arg Gln Pro Thr Tyr Cys Ser His Cys Arg Asp Phe Ile Trp Gly
            180                 185                 190

Val Ile Gly Lys Gln Gly Tyr Gln Cys Gln Val Cys Thr Cys Val Val
        195                 200                 205

His Lys Arg Cys His Glu Leu Ile Ile Thr Lys Cys Ala Gly Leu Lys
    210                 215                 220
```

-continued

```
Lys Gln Glu Thr Pro Asp Gln Val Gly Ser Gln Arg Phe Ser Val Asn
225                 230                 235                 240

Met Pro His Lys Phe Gly Ile His Asn Tyr Lys Val Pro Thr Phe Cys
            245                 250                 255

Asp His Cys Gly Ser Leu Leu Trp Gly Leu Leu Arg Gln Gly Leu Gln
                260                 265                 270

Cys Lys Val Cys Lys Met Asn Val His Arg Arg Cys Glu Thr Asn Val
            275                 280                 285

Ala Pro Asn Cys Gly Val Asp Ala Arg Gly Ile Ala Lys Val Leu Ala
290                 295                 300

Asp Leu Gly Val Thr Pro Asp Lys Ile Thr Asn Ser Gly Gln Arg Arg
305                 310                 315                 320

Lys Lys Leu Ile Ala Gly Ala Glu Ser Pro Gln Pro Ala Ser Gly Ser
                325                 330                 335

Ser Pro Ser Glu Glu Asp Arg Ser Lys Ser Ala Pro Thr Ser Pro Cys
                340                 345                 350

Asp Gln Glu Ile Lys Glu Leu Glu Asn Asn Ile Arg Lys Ala Leu Ser
                355                 360                 365

Phe Asp Asn Arg Gly Glu Glu His Arg Ala Ala Ser Ser Pro Asp Gly
                370                 375                 380

Gln Leu Met Ser Pro Gly Glu Asn Gly Glu Val Arg Gln Gly Gln Ala
385                 390                 395                 400

Lys Arg Leu Gly Leu Asp Glu Phe Asn Phe Ile Lys Val Leu Gly Lys
                405                 410                 415

Gly Ser Phe Gly Lys Val Met Leu Ala Glu Leu Lys Gly Lys Asp Glu
                420                 425                 430

Val Tyr Ala Val Lys Val Leu Lys Lys Asp Val Ile Leu Gln Asp Asp
                435                 440                 445

Asp Val Asp Cys Thr Met Thr Glu Lys Arg Ile Leu Ala Leu Ala Arg
450                 455                 460

Lys His Pro Tyr Leu Thr Gln Leu Tyr Cys Cys Phe Gln Thr Lys Asp
465                 470                 475                 480

Arg Leu Phe Phe Val Met Glu Tyr Val Asn Gly Gly Asp Leu Met Phe
                485                 490                 495

Gln Ile Gln Arg Ser Arg Lys Phe Asp Glu Pro Arg Ser Arg Phe Tyr
                500                 505                 510

Ala Ala Glu Val Thr Ser Ala Leu Met Phe Leu His Gln His Gly Val
                515                 520                 525

Ile Tyr Arg Asp Leu Lys Leu Asp Asn Ile Leu Leu Asp Ala Glu Gly
                530                 535                 540

His Cys Lys Leu Ala Asp Phe Gly Met Cys Lys Glu Gly Ile Leu Asn
545                 550                 555                 560

Gly Val Thr Thr Thr Thr Phe Cys Gly Thr Pro Asp Tyr Ile Ala Pro
                565                 570                 575

Glu Ile Leu Gln Glu Leu Glu Tyr Gly Pro Ser Val Asp Trp Trp Ala
                580                 585                 590

Leu Gly Val Leu Met Tyr Glu Met Met Ala Gly Gln Pro Pro Phe Glu
                595                 600                 605

Ala Asp Asn Glu Asp Asp Leu Phe Glu Ser Ile Leu His Asp Asp Val
                610                 615                 620

Leu Tyr Pro Val Trp Leu Ser Lys Glu Ala Val Ser Ile Leu Lys Ala
625                 630                 635                 640

Phe Met Thr Lys Asn Pro His Lys Arg Leu Gly Cys Val Ala Ser Gln
```

```
                    645                 650                 655
Asn Gly Glu Asp Ala Ile Lys Gln His Pro Phe Phe Lys Glu Ile Asp
            660                 665                 670

Trp Val Leu Leu Glu Gln Lys Lys Ile Lys Pro Pro Phe Lys Pro Arg
            675                 680                 685

Ile Lys Thr Lys Arg Asp Val Asn Asn Phe Asp Gln Asp Phe Thr Arg
            690                 695                 700

Glu Glu Pro Val Leu Thr Leu Val Asp Glu Ala Ile Val Lys Gln Ile
705                 710                 715                 720

Asn Gln Glu Glu Phe Lys Gly Phe Ser Tyr Phe Gly Glu Asp Leu Met
                725                 730                 735

Pro

<210> SEQ ID NO 5
<211> LENGTH: 16
<212> TYPE: PRT
<213> ORGANISM: artificial
<220> FEATURE:
<223> OTHER INFORMATION: PKC.epsilon substrate peptide

<400> SEQUENCE: 5

Glu Arg Met Arg Pro Arg Lys Arg Gln Gly Ser Val Arg Arg Arg Val
1               5                   10                  15

<210> SEQ ID NO 6
<211> LENGTH: 7
<212> TYPE: PRT
<213> ORGANISM: artificial
<220> FEATURE:
<223> OTHER INFORMATION: PKC.epsilon V1-1 inhibitory peptide

<400> SEQUENCE: 6

Asn Gly Leu Leu Lys Ile Lys
1               5

<210> SEQ ID NO 7
<211> LENGTH: 8
<212> TYPE: PRT
<213> ORGANISM: artificial
<220> FEATURE:
<223> OTHER INFORMATION: PKC.epsilon V1-2 inhibitory peptide

<400> SEQUENCE: 7

Glu Ala Val Ser Leu Lys Pro Thr
1               5

<210> SEQ ID NO 8
<211> LENGTH: 11
<212> TYPE: PRT
<213> ORGANISM: artificial
<220> FEATURE:
<223> OTHER INFORMATION: PKC.epsilon V1-3 inhibitory peptide

<400> SEQUENCE: 8

Leu Ala Val Phe His Asp Ala Pro Ile Gly Tyr
1               5                   10

<210> SEQ ID NO 9
<211> LENGTH: 9
<212> TYPE: PRT
<213> ORGANISM: artificial
<220> FEATURE:
<223> OTHER INFORMATION: PKC.epsilon V1-4 inhibitory peptide

<400> SEQUENCE: 9
```

```
Asp Asp Phe Val Ala Asn Cys Thr Ile
1               5

<210> SEQ ID NO 10
<211> LENGTH: 10
<212> TYPE: PRT
<213> ORGANISM: artificial
<220> FEATURE:
<223> OTHER INFORMATION: PKC.epsilon V1-5 inhibitory peptide

<400> SEQUENCE: 10

Trp Ile Asp Leu Glu Pro Glu Gly Arg Val
1               5                   10

<210> SEQ ID NO 11
<211> LENGTH: 10
<212> TYPE: PRT
<213> ORGANISM: artificial
<220> FEATURE:
<223> OTHER INFORMATION: PKC.epsilon V1-6 inhibitory peptide

<400> SEQUENCE: 11

His Ala Val Gly Pro Arg Pro Gln Thr Phe
1               5                   10

<210> SEQ ID NO 12
<211> LENGTH: 16
<212> TYPE: PRT
<213> ORGANISM: artificial
<220> FEATURE:
<223> OTHER INFORMATION: PKC.epsilon pseudosubstrate region (149-164)
      peptide

<400> SEQUENCE: 12

Glu Arg Met Arg Pro Arg Lys Arg Gln Gly Ala Val Arg Arg Arg Val
1               5                   10                  15

<210> SEQ ID NO 13
<211> LENGTH: 7
<212> TYPE: PRT
<213> ORGANISM: Drosophila melanogaster

<400> SEQUENCE: 13

Arg Arg Met Lys Trp Lys Lys
1               5

<210> SEQ ID NO 14
<211> LENGTH: 737
<212> TYPE: PRT
<213> ORGANISM: Homo sapiens

<400> SEQUENCE: 14

Met Val Val Phe Asn Gly Leu Leu Lys Ile Lys Ile Cys Glu Ala Val
1               5                   10                  15

Ser Leu Lys Pro Thr Ala Trp Ser Leu Arg His Ala Val Gly Pro Arg
                20                  25                  30

Pro Gln Thr Phe Leu Leu Asp Pro Tyr Ile Ala Leu Asn Val Asp Asp
            35                  40                  45

Ser Arg Ile Gly Gln Thr Ala Thr Lys Gln Lys Thr Asn Ser Pro Ala
        50                  55                  60

Trp His Asp Glu Phe Val Thr Asp Val Cys Asn Gly Arg Lys Ile Glu
65                  70                  75                  80

Leu Ala Val Phe His Asp Ala Pro Ile Gly Tyr Asp Asp Phe Val Ala
                85                  90                  95
```

```
Asn Cys Thr Ile Gln Phe Glu Glu Leu Leu Gln Asn Gly Ser Arg His
                100                 105                 110
Phe Glu Asp Trp Ile Asp Leu Glu Pro Glu Gly Arg Val Tyr Val Ile
            115                 120                 125
Ile Asp Leu Ser Gly Ser Ser Gly Glu Ala Pro Lys Asp Asn Glu Glu
        130                 135                 140
Arg Val Phe Arg Glu Arg Met Arg Pro Arg Lys Arg Gln Gly Ala Val
145                 150                 155                 160
Arg Arg Arg Val His Gln Val Asn Gly His Lys Phe Met Ala Thr Tyr
                165                 170                 175
Leu Arg Gln Pro Thr Tyr Cys Ser His Cys Arg Asp Phe Ile Trp Gly
            180                 185                 190
Val Ile Gly Lys Gln Gly Tyr Gln Cys Gln Val Cys Thr Cys Val Val
        195                 200                 205
His Lys Arg Cys His Glu Leu Ile Ile Thr Lys Cys Ala Gly Leu Lys
    210                 215                 220
Lys Gln Glu Thr Pro Asp Gln Val Gly Ser Gln Arg Phe Ser Val Asn
225                 230                 235                 240
Met Pro His Lys Phe Gly Ile His Asn Tyr Lys Val Pro Thr Phe Cys
                245                 250                 255
Asp His Cys Gly Ser Leu Leu Trp Gly Leu Leu Arg Gln Gly Leu Gln
            260                 265                 270
Cys Lys Val Cys Lys Met Asn Val His Arg Arg Cys Glu Thr Asn Val
        275                 280                 285
Ala Pro Asn Cys Gly Val Asp Ala Arg Gly Ile Ala Lys Val Leu Ala
    290                 295                 300
Asp Leu Gly Val Thr Pro Asp Lys Ile Thr Asn Ser Gly Gln Arg Arg
305                 310                 315                 320
Lys Lys Leu Ile Ala Gly Ala Glu Ser Pro Gln Pro Ala Ser Gly Ser
                325                 330                 335
Ser Pro Ser Glu Glu Asp Arg Ser Lys Ser Ala Pro Thr Ser Pro Cys
            340                 345                 350
Asp Gln Glu Ile Lys Glu Leu Glu Asn Asn Ile Arg Lys Ala Leu Ser
        355                 360                 365
Phe Asp Asn Arg Gly Glu Glu His Arg Ala Ala Ser Ser Pro Asp Gly
    370                 375                 380
Gln Leu Met Ser Pro Gly Glu Asn Gly Glu Val Arg Gln Gly Gln Ala
385                 390                 395                 400
Lys Arg Leu Gly Leu Asp Glu Phe Asn Phe Ile Lys Val Leu Gly Lys
                405                 410                 415
Gly Ser Phe Gly Lys Val Met Leu Ala Glu Leu Lys Gly Lys Asp Glu
            420                 425                 430
Val Tyr Ala Val Arg Val Leu Lys Lys Asp Val Ile Leu Gln Asp Asp
        435                 440                 445
Asp Val Asp Cys Thr Met Thr Glu Lys Arg Ile Leu Ala Leu Ala Arg
    450                 455                 460
Lys His Pro Tyr Leu Thr Gln Leu Tyr Cys Cys Phe Gln Thr Lys Asp
465                 470                 475                 480
Arg Leu Phe Phe Val Met Glu Tyr Val Asn Gly Gly Asp Leu Met Phe
                485                 490                 495
Gln Ile Gln Arg Ser Arg Lys Phe Asp Glu Pro Arg Ser Arg Phe Tyr
            500                 505                 510
Ala Ala Glu Val Thr Ser Ala Leu Met Phe Leu His Gln His Gly Val
```

```
                    515                 520                 525
Ile Tyr Arg Asp Leu Lys Leu Asp Asn Ile Leu Leu Asp Ala Glu Gly
        530                 535                 540

His Cys Lys Leu Ala Asp Phe Gly Met Cys Lys Glu Gly Ile Leu Asn
545                 550                 555                 560

Gly Val Thr Thr Thr Thr Phe Cys Gly Thr Pro Asp Tyr Ile Ala Pro
                565                 570                 575

Glu Ile Leu Gln Glu Leu Glu Tyr Gly Pro Ser Val Asp Trp Trp Ala
                580                 585                 590

Leu Gly Val Leu Met Tyr Glu Met Met Ala Gly Gln Pro Pro Phe Glu
            595                 600                 605

Ala Asp Asn Glu Asp Asp Leu Phe Glu Ser Ile Leu His Asp Asp Val
        610                 615                 620

Leu Tyr Pro Val Trp Leu Ser Lys Glu Ala Val Ser Ile Leu Lys Ala
625                 630                 635                 640

Phe Met Thr Lys Asn Pro His Lys Arg Leu Gly Cys Val Ala Ser Gln
                645                 650                 655

Asn Gly Glu Asp Ala Ile Lys Gln His Pro Phe Phe Lys Glu Ile Asp
            660                 665                 670

Trp Val Leu Leu Glu Gln Lys Lys Ile Lys Pro Pro Phe Lys Pro Arg
        675                 680                 685

Ile Lys Thr Lys Arg Asp Val Asn Asn Phe Asp Gln Asp Phe Thr Arg
690                 695                 700

Glu Glu Pro Val Leu Thr Leu Val Asp Glu Ala Ile Val Lys Gln Ile
705                 710                 715                 720

Asn Gln Glu Glu Phe Lys Gly Phe Ser Tyr Phe Gly Glu Asp Leu Met
                725                 730                 735

Pro

<210> SEQ ID NO 15
<211> LENGTH: 737
<212> TYPE: PRT
<213> ORGANISM: Mus musculus

<400> SEQUENCE: 15

Met Val Val Phe Asn Gly Leu Leu Lys Ile Lys Ile Cys Glu Ala Val
1               5                   10                  15

Ser Leu Lys Pro Thr Ala Trp Ser Leu Arg His Ala Val Gly Pro Arg
            20                  25                  30

Pro Gln Thr Phe Leu Leu Asp Pro Tyr Ile Ala Leu Asn Val Asp Asp
        35                  40                  45

Ser Arg Ile Gly Gln Thr Ala Thr Lys Gln Lys Thr Asn Ser Pro Ala
    50                  55                  60

Trp His Asp Glu Phe Val Thr Asp Val Cys Asn Gly Arg Lys Ile Glu
65              70                  75                  80

Leu Ala Val Phe His Asp Ala Pro Ile Gly Tyr Asp Asp Phe Val Ala
                85                  90                  95

Asn Cys Thr Ile Gln Phe Glu Glu Leu Leu Gln Asn Gly Ser Arg His
            100                 105                 110

Phe Glu Asp Trp Ile Asp Leu Glu Pro Glu Gly Lys Val Tyr Val Ile
        115                 120                 125

Ile Asp Leu Ser Gly Ser Ser Gly Glu Ala Pro Lys Asp Asn Glu Glu
    130                 135                 140

Arg Val Phe Arg Glu Arg Met Arg Pro Arg Lys Arg Gln Gly Ala Val
145                 150                 155                 160
```

```
Arg Arg Arg Val His Gln Val Asn Gly His Lys Phe Met Ala Thr Tyr
            165                 170                 175

Leu Arg Gln Pro Thr Tyr Cys Ser His Cys Arg Asp Phe Ile Trp Gly
            180                 185                 190

Val Ile Gly Lys Gln Gly Tyr Gln Cys Gln Val Cys Thr Cys Val Val
            195                 200                 205

His Lys Arg Cys His Glu Leu Ile Ile Thr Lys Cys Ala Gly Leu Lys
    210                 215                 220

Lys Gln Glu Thr Pro Asp Glu Val Gly Ser Gln Arg Phe Ser Val Asn
225                 230                 235                 240

Met Pro His Lys Phe Gly Ile His Asn Tyr Lys Val Pro Thr Phe Cys
            245                 250                 255

Asp His Cys Gly Ser Leu Leu Trp Gly Leu Leu Arg Gln Gly Leu Gln
            260                 265                 270

Cys Lys Val Cys Lys Met Asn Val His Arg Arg Cys Glu Thr Asn Val
            275                 280                 285

Ala Pro Asn Cys Gly Val Asp Ala Arg Gly Ile Ala Lys Val Leu Ala
    290                 295                 300

Asp Leu Gly Val Thr Pro Asp Lys Ile Thr Asn Ser Gly Gln Arg Arg
305                 310                 315                 320

Lys Lys Leu Ala Ala Gly Ala Glu Ser Pro Gln Pro Ala Ser Gly Asn
            325                 330                 335

Ser Pro Ser Glu Asp Asp Arg Ser Lys Ser Ala Pro Thr Ser Pro Cys
            340                 345                 350

Asp Gln Glu Leu Lys Glu Leu Glu Asn Asn Ile Arg Lys Ala Leu Ser
            355                 360                 365

Phe Asp Asn Arg Gly Glu Glu His Arg Ala Ser Ser Ala Thr Asp Gly
    370                 375                 380

Gln Leu Ala Ser Pro Gly Glu Asn Gly Glu Val Arg Pro Gly Gln Ala
385                 390                 395                 400

Lys Arg Leu Gly Leu Asp Glu Phe Asn Phe Ile Lys Val Leu Gly Lys
            405                 410                 415

Gly Ser Phe Gly Lys Val Met Leu Ala Glu Leu Lys Gly Lys Asp Glu
            420                 425                 430

Val Tyr Ala Val Arg Val Leu Lys Lys Asp Val Ile Leu Gln Asp Asp
    435                 440                 445

Asp Val Asp Cys Thr Met Thr Glu Lys Arg Ile Leu Ala Leu Ala Arg
450                 455                 460

Lys His Pro Tyr Leu Thr Gln Leu Tyr Cys Cys Phe Gln Thr Lys Asp
465                 470                 475                 480

Arg Leu Phe Phe Val Met Glu Tyr Val Asn Gly Gly Asp Leu Met Phe
            485                 490                 495

Gln Ile Gln Arg Ser Arg Lys Phe Asp Glu Pro Arg Ser Arg Phe Tyr
            500                 505                 510

Ala Ala Glu Val Thr Ser Ala Leu Met Phe Leu His Gln His Gly Val
            515                 520                 525

Ile Tyr Arg Asp Leu Lys Leu Asp Asn Ile Leu Leu Asp Ala Glu Gly
    530                 535                 540

His Cys Lys Leu Ala Asp Phe Gly Met Cys Lys Glu Gly Ile Met Asn
545                 550                 555                 560

Gly Val Thr Thr Thr Phe Cys Gly Thr Pro Asp Tyr Ile Ala Pro
            565                 570                 575

Glu Ile Leu Gln Glu Leu Glu Tyr Gly Pro Ser Val Asp Trp Trp Ala
```

```
                580             585             590
Leu Gly Val Leu Met Tyr Glu Met Met Ala Gly Gln Pro Pro Phe Glu
        595                 600                 605
Ala Asp Asn Glu Asp Leu Phe Glu Ser Ile Leu His Asp Asp Val
    610                 615                 620
Leu Tyr Pro Val Trp Leu Ser Lys Glu Ala Val Ser Ile Leu Lys Ala
625                 630                 635                 640
Phe Met Thr Lys Asn Pro His Lys Arg Leu Gly Cys Val Ala Ala Gln
                645                 650                 655
Asn Gly Glu Asp Ala Ile Lys Gln His Pro Phe Phe Lys Glu Ile Asp
            660                 665                 670
Trp Val Leu Leu Glu Gln Lys Lys Ile Lys Pro Pro Phe Lys Pro Arg
        675                 680                 685
Ile Lys Thr Lys Arg Asp Val Asn Asn Phe Asp Gln Asp Phe Thr Arg
    690                 695                 700
Glu Glu Pro Ile Leu Thr Leu Val Asp Glu Ala Ile Ile Lys Gln Ile
705                 710                 715                 720
Asn Gln Glu Glu Phe Lys Gly Phe Ser Tyr Phe Gly Glu Asp Leu Met
                725                 730                 735
Pro

<210> SEQ ID NO 16
<211> LENGTH: 20
<212> TYPE: DNA
<213> ORGANISM: artificial
<220> FEATURE:
<223> OTHER INFORMATION: PKC.epsilon oligonucleotide inhibitor

<400> SEQUENCE: 16
catgagggcc gatgtgacct                                              20

<210> SEQ ID NO 17
<211> LENGTH: 20
<212> TYPE: DNA
<213> ORGANISM: artificial
<220> FEATURE:
<223> OTHER INFORMATION: PKC.epsilon oligonucleotide inhibitor

<400> SEQUENCE: 17
tgccacacag cccaggcgca                                              20

<210> SEQ ID NO 18
<211> LENGTH: 20
<212> TYPE: DNA
<213> ORGANISM: artificial
<220> FEATURE:
<223> OTHER INFORMATION: PKC.epsilon oligonucleotide inhibitor

<400> SEQUENCE: 18
aaggaaagtc tgcggccggg                                              20

<210> SEQ ID NO 19
<211> LENGTH: 20
<212> TYPE: DNA
<213> ORGANISM: artificial
<220> FEATURE:
<223> OTHER INFORMATION: PKC.epsilon oligonucleotide inhibitor

<400> SEQUENCE: 19
tggcggctcc cgttctgcag                                              20
```

```
<210> SEQ ID NO 20
<211> LENGTH: 20
<212> TYPE: DNA
<213> ORGANISM: artificial
<220> FEATURE:
<223> OTHER INFORMATION: PKC.epsilon oligonucleotide inhibitor

<400> SEQUENCE: 20
gcttcctcgg ccgcatgcgt                                          20

<210> SEQ ID NO 21
<211> LENGTH: 20
<212> TYPE: DNA
<213> ORGANISM: artificial
<220> FEATURE:
<223> OTHER INFORMATION: PKC.epsilon oligonucleotide inhibitor

<400> SEQUENCE: 21
ttgacgctga accgctggga                                          20

<210> SEQ ID NO 22
<211> LENGTH: 20
<212> TYPE: DNA
<213> ORGANISM: artificial
<220> FEATURE:
<223> OTHER INFORMATION: PKC.epsilon oligonucleotide inhibitor

<400> SEQUENCE: 22
gcccggtgct cctctcctcg                                          20

<210> SEQ ID NO 23
<211> LENGTH: 20
<212> TYPE: DNA
<213> ORGANISM: artificial
<220> FEATURE:
<223> OTHER INFORMATION: PKC.epsilon oligonucleotide inhibitor

<400> SEQUENCE: 23
gggccgatgt gacctctgca                                          20

<210> SEQ ID NO 24
<211> LENGTH: 20
<212> TYPE: DNA
<213> ORGANISM: artificial
<220> FEATURE:
<223> OTHER INFORMATION: PKC.epsilon oligonucleotide inhibitor

<400> SEQUENCE: 24
tggaggaaca tgagggccga                                          20

<210> SEQ ID NO 25
<211> LENGTH: 20
<212> TYPE: DNA
<213> ORGANISM: artificial
<220> FEATURE:
<223> OTHER INFORMATION: PKC.epsilon oligonucleotide inhibitor

<400> SEQUENCE: 25
cccccagggc ccaccagtcc                                          20

<210> SEQ ID NO 26
<211> LENGTH: 20
<212> TYPE: DNA
<213> ORGANISM: artificial
<220> FEATURE:
<223> OTHER INFORMATION: PKC.epsilon oligonucleotide inhibitor

<400> SEQUENCE: 26
```

```
tgcgatgcca cacagcccag                                                    20

<210> SEQ ID NO 27
<211> LENGTH: 20
<212> TYPE: DNA
<213> ORGANISM: artificial
<220> FEATURE:
<223> OTHER INFORMATION: PKC.epsilon oligonucleotide inhibitor

<400> SEQUENCE: 27
tgggctctca gggcatcagg                                                    20
```